(12) United States Patent
Combs et al.

(10) Patent No.: US 9,957,268 B2
(45) Date of Patent: *May 1, 2018

(54) 1H-PYRROLO[2,3,C]PYRIDIN-7(6H)-ONES AND PYRAZOLO[3,4-C]PYRIDIN-7(6H)-ONES AS INHIBITORS OF BET PROTEINS

(71) Applicant: Incyte Corporation, Wilmington, DE (US)

(72) Inventors: Andrew P. Combs, Kennett Square, PA (US); Thomas P. Maduskuie, Jr., Wilmington, DE (US); Nikoo Falahatpisheh, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/354,223

(22) Filed: Nov. 17, 2016

(65) Prior Publication Data

US 2017/0158689 A1 Jun. 8, 2017

Related U.S. Application Data

(63) Continuation of application No. 14/693,424, filed on Apr. 22, 2015, now Pat. No. 9,540,368.

(60) Provisional application No. 61/983,289, filed on Apr. 23, 2014.

(51) Int. Cl.
C07D 471/04 (2006.01)
A61K 31/546 (2006.01)

(52) U.S. Cl.
CPC .......... *C07D 471/04* (2013.01); *A61K 31/546* (2013.01)

(58) Field of Classification Search
CPC .......................... C07D 471/04; A61K 31/546
USPC ........................................ 544/105; 514/230.5
See application file for complete search history.

(56) References Cited

U.S. PATENT DOCUMENTS

| | | | |
|---|---|---|---|
| 5,589,476 A | 12/1996 | Jegham et al. | |
| 8,633,186 B2 | 1/2014 | Tachdjian et al. | |
| 8,669,249 B2 | 3/2014 | Brown et al. | |
| 9,012,642 B2 | 4/2015 | Haydar et al. | |
| 9,227,985 B2 | 1/2016 | Combs et al. | |
| 9,290,514 B2 | 3/2016 | Combs et al. | |
| 9,309,246 B2 | 4/2016 | Rodgers et al. | |
| 9,315,501 B2 | 4/2016 | Yue et al. | |
| 9,399,640 B2 | 7/2016 | Yue et al. | |
| 9,527,864 B2 | 12/2016 | Combs et al. | |
| 9,533,997 B2 | 1/2017 | Combs et al. | |
| 9,540,368 B2 * | 1/2017 | Combs ................. | C07D 471/04 |
| 9,624,241 B2 | 4/2017 | Combs et al. | |
| 9,737,516 B2 | 8/2017 | Yue et al. | |
| 9,777,003 B2 | 10/2017 | Shepard et al. | |
| 2002/0004510 A1 | 1/2002 | McCall et al. | |
| 2007/0191447 A1 | 8/2007 | Kodo et al. | |
| 2007/0244096 A1 | 10/2007 | Fox et al. | |
| 2008/0306093 A1 | 12/2008 | Servant et al. | |
| 2009/0306122 A1 | 12/2009 | Staehle et al. | |
| 2013/0045229 A1 | 2/2013 | Iadonato et al. | |
| 2013/0261109 A1 | 10/2013 | Miyoshi et al. | |
| 2013/0281396 A1 | 10/2013 | McLure et al. | |
| 2013/0281397 A1 | 10/2013 | McLure et al. | |
| 2013/0281398 A1 | 10/2013 | McLure et al. | |
| 2013/0281399 A1 | 10/2013 | McLure et al. | |
| 2014/0135316 A1 | 5/2014 | Albrecht et al. | |
| 2014/0275030 A1 | 9/2014 | Combs et al. | |
| 2015/0011540 A1 | 1/2015 | Combs et al. | |
| 2015/0148342 A1 | 5/2015 | Yue et al. | |
| 2015/0148372 A1 | 5/2015 | Yue et al. | |
| 2015/0148375 A1 | 5/2015 | Yue et al. | |
| 2015/0175604 A1 | 6/2015 | Rodgers et al. | |
| 2015/0307493 A1 | 10/2015 | Combs et al. | |
| 2016/0046650 A1 | 2/2016 | Combs et al. | |
| 2016/0075721 A1 | 3/2016 | Combs et al. | |
| 2016/0159817 A1 | 6/2016 | Combs et al. | |
| 2016/0168148 A1 | 6/2016 | Shepard | |
| 2016/0213654 A1 | 7/2016 | Yue et al. | |
| 2016/0331749 A1 | 11/2016 | Bogdan et al. | |
| 2017/0014418 A1 | 1/2017 | Yue et al. | |
| 2017/0121347 A1 | 5/2017 | Chen et al. | |
| 2017/0158710 A1 | 6/2017 | Combs et al. | |
| 2017/0210754 A1 | 7/2017 | Combs et al. | |
| 2017/0127985 A1 | 8/2017 | Combs et al. | |

FOREIGN PATENT DOCUMENTS

| | | |
|---|---|---|
| CA | 2171579 | 9/1996 |
| EP | 0646583 | 4/1995 |
| EP | 0 732 334 | 9/1996 |
| EP | 1462103 | 9/2004 |
| EP | 2 239 264 | 10/2010 |
| EP | 2415767 | 2/2012 |

(Continued)

OTHER PUBLICATIONS

Bauer, "Pharmaceutical Solids—The Amorphous Phase," Journal of Validation Technology, Jan. 2009, 15(3): 63-68.

Byrn et al., "Pharmaceutical Solids: A Strategic Approach to Regulatory Considerations," Pharmaceutical Research, Jul. 1995, 12(7): 945-954.

Cheng et al., "Inhibition of BET Bromodomain Targets Genetically Diverse Glioblastoma," Clin Cancer Res 19:1748-1759, Feb. 2013.

Chilean Office Action in Chilean Application No. 201502734, dated Jan. 18, 2017, 8 pages (English Translation).

(Continued)

*Primary Examiner* — Kahsay Habte

(74) *Attorney, Agent, or Firm* — Fish & Richardson P.C.

(57) ABSTRACT

The present invention relates to substituted pyrrolopyridinones and substituted pyrazolopyridinones which are inhibitors of BET proteins such as BRD2, BRD3, BRD4, and BRD-t and are useful in the treatment of diseases such as cancer.

12 Claims, No Drawings

(56) References Cited

FOREIGN PATENT DOCUMENTS

| | | |
|---|---|---|
| EP | 2568287 | 3/2013 |
| EP | 2573559 | 3/2013 |
| FR | 2747678 | 10/1997 |
| JP | H03014566 | 1/1991 |
| JP | H05-097849 | 4/1993 |
| JP | 08-269058 | 10/1996 |
| JP | 2004-502650 | 1/2004 |
| JP | 2006-509764 | 3/2006 |
| JP | 2008-532954 | 8/2008 |
| JP | 2009-503069 | 1/2009 |
| JP | 2012-529536 | 11/2012 |
| JP | 2012-530053 | 11/2012 |
| JP | 2013/010719 | 1/2013 |
| KR | 20150037711 | 4/2015 |
| WO | WO 2002/000196 | 1/2002 |
| WO | WO 2004/024736 | 3/2004 |
| WO | WO 2005/080334 | 9/2005 |
| WO | WO 2005/099688 | 10/2005 |
| WO | WO 2006/124874 | 11/2006 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/024987 | 3/2011 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/107465 | 8/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |
| WO | WO 2015/013635 | 1/2015 |
| WO | WO 2015/081203 | 6/2015 |
| WO | WO 2015/095445 | 6/2015 |
| WO | WO 2015/164480 | 10/2015 |
| WO | WO 2015/168555 | 11/2015 |
| WO | WO 2015/168621 | 11/2015 |
| WO | WO 2015/169951 | 11/2015 |
| WO | WO 2015/169953 | 11/2015 |
| WO | WO 2015/184257 | 12/2015 |
| WO | WO 2016/044130 | 3/2016 |
| WO | WO 2016/077378 | 5/2016 |
| WO | WO 2016/186453 | 11/2016 |
| WO | WO 2016/194806 | 12/2016 |
| WO | WO 2017/127930 | 8/2017 |
| WO | WO 2017/133681 | 8/2017 |

OTHER PUBLICATIONS

Chinese Office Action in Chinese Application No. 201480025137, dated Feb. 16, 2017, 21 pages (w/ English Translation).

Eurasian Office Action in Eurasian Application No. 201692134, dated Jun. 6, 2017, 4 pages (English Translation).

Greenwald et al., "Eµ-BRD2 transgenic mice develop B-cell lymphoma and leukemia," Blood 103(4):1475-1484, Feb. 2004.

International Search Report and Written Opinion in International Application No. PCT/US2016/059360, dated Feb. 13, 2017, 20 pages.

Puissant et al., "Targeting MYCN in Neuroblastoma by BET Bromodomain Inhibition," Cancer Discovery, 16 pages, Mar. 2013.

(56) References Cited

OTHER PUBLICATIONS

Segura et al., "BRD4 Sustains Melanoma Proliferation and Represents a New Target for Epigenetic Therapy," Cancer Res 73:6264-6276, Aug. 2013.
Shimamura et al., "Efficacy of BET Bromodomain Inhibition in Kras-Mutant Non-Small Cell Lung Cancer," Clin Cancer Res, 10 pages, 2013.
Wyce et al., "Inhibition of BET bromodomain proteins as a therapeutic appraoch in prostate cancer," Oncotarget, 13 pages, Nov. 2013.
Ai et al., "Signal-induced Brd4 release from chromatin is essential for its role transition from chromatin targeting to transcriptional regulation," Nucleic Acids Res., 2011, 1-13.
Bamborough et al., "Fragment-Based Discovery of Bromodomain Inhibitors Part 2: Optimization of Phenylisoxazole Sulfonamides," J Med Chem., 2012, 55:587-596.
Bartholomeeusen et al., "BET bromodomain inhibition activates transcription via a transient release of P-TEFb from 7SK snRNP," JBC, 2012, 16 pages.
Belkina and Denis, "BET domain co-regulators in obesity inflammation and cancer," Nat Rev Cancer, Jul. 2012, U:465-477.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Chiang, "Brd4 engagement from chromatin targeting to transcriptional regulation: selective contact with acetylated histone H3 and H4," Biology Reports, Dec. 2009, 1:98, 7 pages.
Chinese Office Action in Chinese Application No. 201480025137, dated May 17, 2016, 14 pages (English Translation).
Chung et al., "Discovery and Characterization of Small Molecule Inhibitors of the BET Family Bromodomains," J Med Chem., 2011, 54:3827-3838.
Chung et al., "Fragment-Based Discovery of Bromodomain Inhibitors Part 1: Inhibitor Binding Modes and Implications for Lead Discovery," J Med Chem., 2011, 11 pages.
Chung et al., "Fragment-based discovery of bromodomain inhibitors part 1: inhibitor binding modes and implications for lead discovery," Supporting Information, 2011, 6 pages.
Dawson et al., "Inhibition of BET recruitment to chromatin as an effective treatment for MLL-fusion leukaemia," Nature, 2011, 5 pages.
Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphotylates serine2 of the RNA polymerase II carboxy-terminal domain," Proc. Nat. Acad. Sci. USA., 2012, 109(18):6927-6932.
Draker et al., "A Combination of H2A.Z and H4 Acetylation Recruits Brd2 to Chromatin during Transcriptional Activation," PLoS Genet., Nov. 2012, 8(11):e1003047, 17 pages.
Dorwald, F. Zaragoza. Side Reactions in Organic Synthesis: A Guide to Successful Synthesis Design, Weinheim: WILEY-VCH Verlag GmbH & Co. KGaA, 2005, Preface.
Filippakopoulos and Knapp, "Targeting bromodomains: epigenetic readers of lysine acetylation," Nature Rev Drug Disc., May 2014, 13:337-356.
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.
French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "Nut midline carcinoma," Cancer Genet Cytogenetics, 2010, 203:16-20.
Frizzo et al., "Structural and thermodynamic properties of new pyrazolo [3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Hackam et al., JAMA, 296(14), 2006, 1731-1732.
Hewings et al., "3,5-Dimethylisoxazoles Act as Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscript).
Hewings et al., "Progress in the Development and Applciation of Small Molecule Inhibitors of Bromodomain-Acetyl-lysine Interactions," J Med Chem., Nov. 2012, 55(22):9393-9413.
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
International Preliminary Report on Patentability in International Application No. PCT/US2014/045543, dated Jan. 21, 2016, 7 pages.
International Search Report and Written Opinion in International Application No. PCT/US2014/027872, dated Jun. 30, 2014, 12 pages.
International Search Report and Written Opinion in International Application No. PCT/US2014/045543, dated Sep. 10, 2014, 11 pages.
International Search Report and Written Opinion in International Application No. PCT/US2014/067598, dated Feb. 13, 2015, 9 pages.
International Search Report and Written Opinion in International Application No. PCT/US2014/067629, dated Feb. 16, 2015, 11 pages.
International Search Report and Written Opinion in International Application No. PCT/US2014/067691, dated Feb. 2, 2015, 10 pages.
International Search Report and Written Opinion in International Application No. PCT/US2014/071102, dated Feb. 13, 2015, 9 pages.

(56) References Cited

OTHER PUBLICATIONS

International Preliminary Report on Patentability in International Application No. PCT/US2014/027872, dated Sep. 24, 2015, 8 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Preliminary Report on Patentability in International Application No. PCT/US2014/067691, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067598, dated May 31, 2016, 7 pages.
International Preliminary Report on Patentability in International Application No. PCT/US2014/071102, dated Jun. 21, 2016, 7 pages.
International Preliminary Report on Patentability in International Application No. PCT/US2015/027047, dated Oct. 25, 2016, 10 pages.
Jang et al., "The bromodomain protein Brd4 is a positive regulatory component of P-TEFb and stimulates RNA polymerase II-dependent transcription," Mol. Cell, Aug. 2005, 19(4):523-534.
Japanese Office Action in Japanese Application No. 2016-502650, dated Jan. 10, 2017, 3 pages (English translation only).
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, is a BET Bromodomain Antagonist," PLOS ONE, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.
Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of Nut Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy number alterations of MYB in human cancer," Cell Cyle, Aug. 2010, 9(15):2986-2955.
Vidler et al.. "Druggability Analysis and Structural Classification of Bromodomain Acetyl-lysine Binding Sites," J Med Chem., 2012, 14 pages.
Wang et al., "Brd2 disruption in mice causes severe obesity without Type 2 diabetes," Biochem. J., 2010, 425(1):71-83.
Wang et al., "The Bromodomain Protein Brd4 Associated with Acetylated Chromatin is Important for Maintenance of Higher-Order Chromatin Structure," JBC, 2012, 22 pages.
Weidner-Glunde et al., "WHAT do viruses BET on?" Frontiers Biosci., Jan 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Interaction of the bovine papillomavirus E2 protein with Brd4 tethers the viral DNA to host mitotic chromosomes," Cell, 2004, 117(3):349-60.

(56) References Cited

OTHER PUBLICATIONS

You et al., "Regulation of Aurora B Expression by the Bromodomain Protein Brd4," Mol Cell Biol., Sep. 2009, 29(18):5094-5103.

Zhang et al., "Bromodomain-Containing-Protein 4 (BRD4) Regulates RNA Polymerase II Serine 2 Phosphorylation in Human CD4+ T Cells," JBC, 2012, 30 pages.

Zhu et al., "Reactivation of latent HIV-1 by inhibition of BRD4," Cell Reports, 2012, 2(4):807-816.

Zuber et al., "An integrated approach to dissecting oncogene addiction implicates a Myb-coordinated self-renewal program as essential for leukemia maintenance," Genes Dev., 2011, 25:1628-1640.

Zuber et al., "RNAi screen identifies Brd4 as a therapeutic target in acute myeloid leukaemia," Nature, 2011, 478(7370):524-528.

Zuber et al., "Supplemental Information: RNAi screen identifies Brd4 as a therapeutic target in acute myeloid leukaemia," Nature, 2011, 33 pages.

Caira, "Crystalline Polymorphism of Organic Compounds," Topics in Current Chemistry, 1998, 198: 163-208.

Chinese Office Action in Chinese Application No. 201480025137, dated Oct. 13, 2017, 7 pages (English Translation).

Colombian Office Action in Colombian Application No. 15-227.987, dated May 23, 2017, 5 pages.

International Search Report and Written Opinion in International Application No. PCT/US2017/038121, dated Oct. 20, 2017, 20 pages.

* cited by examiner

1H-PYRROLO[2,3,C]PYRIDIN-7(6H)-ONES AND PYRAZOLO[3,4-C]PYRIDIN-7(6H)-ONES AS INHIBITORS OF BET PROTEINS

FIELD OF THE INVENTION

The present invention relates to substituted pyrrolopyridinones and substituted pyrazolopyridinones which are inhibitors of BET proteins such as BRD2, BRD3, BRD4, and BRD-t and are useful in the treatment of diseases such as cancer.

BACKGROUND OF THE INVENTION

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitiously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146: 904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY OF THE INVENTION

The present invention relates to, inter alia, an inhibitor of a BET protein, wherein the inhibitor is a compound of Formula I:

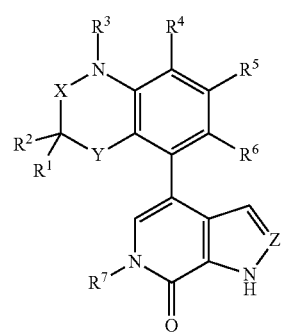

or a pharmaceutically acceptable salt thereof, wherein the variables are defined herein.

The present invention further relates to a pharmaceutical composition comprising a compound of Formula I, or a pharmaceutically acceptable salt thereof, and at least one pharmaceutically acceptable carrier.

The present invention further relates to a method of treating a disease or condition that is associated with a BET protein, comprising administering to a patient in need of such treatment a therapeutically effective amount of a compound of Formula I, or a pharmaceutically acceptable salt thereof.

DETAILED DESCRIPTION

The present invention relates to, inter alia, an inhibitor of a BET protein, wherein the inhibitor is a compound of Formula I:

or a pharmaceutically acceptable salt thereof, wherein:

X is C=O or $CR^8R^9$;

Y is O, S, or $NR^{10}$;

Z is CH or N;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from $R^A$;

or $R^1$ and $R^2$ together with the carbon atom to which they are attached form a $C_{3-10}$ cycloalkyl group or a 4-10 membered heterocycloalkyl group, each optionally substituted with 1, 2, or 3 substituents independently selected from $R^A$;

$R^3$ is H or $C_{1-6}$ alkyl optionally substituted with 1, 2, or 3 substituents independently selected from halo, Cy, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$ $NR^{c2}C(=NR^{e2})NR^{c2}R^{d2}$ $NR^{c2}R^{d2}$ $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^4$ is H, halo, $C_{1-4}$ alkyl, $C_{2-4}$ alkenyl, $C_{2-4}$ alkynyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NRC^3R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$;

$R^5$ is H, halo, $C_{1-6}$ alkyl, $C_{2-6}$ alkenyl, $C_{2-6}$ alkynyl, $C_{1-6}$ haloalkyl, $Cy^2$, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, or $S(O)_2NR^{c4}R^{d4}$; wherein said $C_{1-6}$ alkyl, $C_{2-6}$ alkenyl, and $C_{2-6}$ alkynyl are each optionally substituted with 1, 2, 3, 4, or 5 substituents independently selected from $R^B$;

$R^6$ is H, halo, $C_{1-4}$ alkyl, $C_{1-4}$ haloalkyl, $C_{1-4}$ alkoxy, CN, or OH;

$R^7$ is H or $C_{1-4}$ alkyl;

$R^8$ and $R^9$ are each independently selected from H, halo, $C_{1-4}$ alkyl, and $C_{1-4}$ haloalkyl;

$R^{10}$ is H or $C_{1-4}$ alkyl;

each $R^A$ is independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^B$ is independently selected from $Cy^2$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each Cy is independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from $R^C$;

each $R^C$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-4}$ alkyl, $C_{1-4}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from $R^D$;

each $R^D$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)$ $NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-4}$ alkyl, $C_{1-4}$ haloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $R^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^2$ is independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from $R^E$;

each $R^E$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-4}$ alkyl, $C_{1-4}$ haloalkyl, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, $C_{1-4}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)R^{b5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, $C_{1-4}$ haloalkyl, halo, CN, $OR^{a5}SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a3}$, $R^{b3}$, $R^{c3}$, and $R^{d3}$ is independently selected from H and $C_{1-4}$ alkyl; each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, $C_{1-4}$ haloalkyl, halo, CN, $OR^{a5}SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e1}$, $R^{e2}$, $R^{e3}$, $R^{e4}$, and $R^{e5}$ is independently selected from H, $C_{1-4}$ alkyl, and CN.

In some embodiments, X is C=O.
In some embodiments, X is $CR^8R^9$.
In some embodiments, Y is O.
In some embodiments, Y is $NR^{10}$.
In some embodiments, Z is CH.
In some embodiments, Z is N.
In some embodiments, $R^1$ and $R^2$ are each independently selected from H, $C_{1-6}$ alkyl, and $Cy^1$, wherein said $C_{1-6}$ alkyl is optionally substituted with 1, 2, 3, 4, or 5 substituents independently selected from $R^A$;

or $R^1$ and $R^2$ together with the carbon atom to which they are attached form a $C_{3-10}$ cycloalkyl group optionally substituted with 1, 2, or 3 substituents independently selected from $R^A$.

In some embodiments, $R^1$ and $R^2$ are each independently selected from H, $C_{1-3}$ alkyl, $C_{6-10}$ aryl, $C_{3-10}$ cycloalkyl, 5-10 membered heteroaryl, and 4-10 membered heterocycloalkyl, wherein said $C_{6-10}$ aryl is optionally substituted with 1 or 2 halo, and wherein said $C_{1-3}$ alkyl is optionally substituted by OH;

or $R^1$ and $R^2$ together with the carbon atom to which they are attached form a $C_{3-6}$ cycloalkyl group.

In some embodiments, $R^1$ and $R^2$ are each independently selected from H, methyl, ethyl, propyl, cyclopropyl, cyclopentyl, pyran-4-yl, phenyl, pyridin-2-yl, 2-chloro-4-phenyl, and 2-hydroxyethyl.

In some embodiments, $R^1$ and $R^2$ together with the carbon atom to which they are attached form cyclopropyl, cyclobutyl, cyclopentyl, or cyclohexyl.

In some embodiments, one of $R^1$ and $R^2$ is H and the other is not H.

In some embodiments, $R^1$ and $R^2$ are each $C_{1-6}$ alkyl.
In some embodiments, $R^1$ and $R^2$ are each methyl.

In some embodiments, $R^3$ is H or $C_{1-6}$ alkyl optionally substituted with 1, 2, or 3 substituents independently selected from Cy, $C(=O)NR^{c2}R^{d2}$, and $C(=O)OR^{a2}$.

In some embodiments, $R^3$ is H, methyl, ethyl, or propyl, wherein said methyl is optionally substituted with cyclopropyl, pyridinyl, —C(=O)NHCH_3, —C(=O)NH(4-methyl-piperazin-1-yl), or —C(=O)OH.

In some embodiments, $R^3$ is methyl.

In some embodiments, $R^4$ is H, halo, $C_{1-4}$ alkyl, $C_{1-4}$ haloalkyl, $C_{1-4}$ alkoxy, CN, or OH.

In some embodiments, $R^4$ is H.

In some embodiments, $R^5$ is H, $C_{1-6}$ alkyl, $Cy^2$, CN, $NO_2$, $OR^{a4}$, $C(O)R^{b4}$, $C(O)NR^{c4}R^{d4}$, $S(O)_2R^{b4}$, or $S(O)_2NR^{c4}R^{d4}$; wherein said $C_{1-6}$ alkyl is optionally substituted with 1, 2, 3, 4, or 5 substituents independently selected from $R^B$.

In some embodiments, $R^5$ is H, 1-methyl-1H-pyrazol-4-yl, 2-furyl, CN, $NO_2$, methoxy, —C(=O)NH_2, —C(=O)NH(CH_3), —C(=O)N(CH_3)_2, —C(=O)-(morpholin-4-yl), —C(=O)CH_3, —CH_2OH, —CH_2OCH_3, —CH_2NH_2, —CH_2NHSO_2(CH_2CH_3), —CH_2NHC(=O)CH_3, —CH(OH)CH_3, —SO_2CH_3, —SO_2CH_2CH_3, —SO_2-(isopropyl), —SO_2N(CH_3)_2, —SO_2NH(CH_3), —SO_2—NH(isopropyl), or —SO_2-(piperidin-1-yl).

In some embodiments, $R^5$ is $S(O)_2R^{b4}$.
In some embodiments, $R^6$ is H.
In some embodiments, $R^7$ is $C_{1-4}$ alkyl.
In some embodiments, $R^7$ is methyl.
In some embodiments, $R^8$ and $R^9$ are each H.
In some embodiments, $R^{10}$ is H.

In some embodiments, the compound of the invention has Formula IIa:

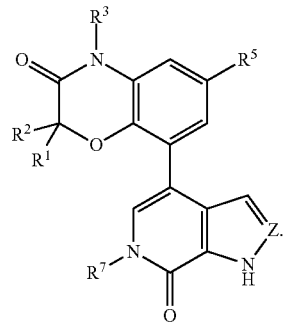

IIa

In some embodiments, where the compound of the invention has Formula IIa, Z is CH.

In some embodiments, where the compound of the invention has Formula IIa, Z is N.

In some embodiments, where the compound of the invention has Formula IIa, $R^1$ and $R^2$ are each independently selected from H, $C_{1-6}$ alkyl, and $Cy^1$, wherein said $C_{1-6}$ alkyl is optionally substituted with 1, 2, 3, 4, or 5 substituents independently selected from $R^A$;

or $R^1$ and $R^2$ together with the carbon atom to which they are attached form a $C_{3-6}$ cycloalkyl group optionally substituted with 1, 2, or 3 substituents independently selected from $R^A$.

In some embodiments, where the compound of the invention has Formula IIa, $R^1$ and $R^2$ are each independently selected from H, $C_{1-3}$ alkyl, $C_{6-10}$ aryl, $C_{3-10}$ cycloalkyl, 5-10 membered heteroaryl, and 4-10 membered heterocycloalkyl, wherein said $C_{6-10}$ aryl is optionally substituted with 1 or 2 halo, and wherein said $C_{1-3}$ alkyl is optionally substituted by OH;

or $R^1$ and $R^2$ together with the carbon atom to which they are attached form a $C_{3-6}$ cycloalkyl group.

In some embodiments, where the compound of the invention has Formula IIa, and $R^2$ are each independently selected from H, methyl, ethyl, propyl, cyclopropyl, cyclopentyl, pyran-4-yl, phenyl, pyridin-2-yl, 2-chloro-4-phenyl, and 2-hydroxyethyl.

In some embodiments, where the compound of the invention has Formula IIa, $R^1$ and $R^2$ together with the carbon atom to which they are attached form cyclopropyl, cyclobutyl, cyclopentyl, or cyclohexyl.

In some embodiments, where the compound of the invention has Formula IIa, $R^1$ and $R^2$ together with the carbon atom to which they are attached form cyclopropyl.

In some embodiments, where the compound of the invention has Formula IIa, one of $R^1$ and $R^2$ is H and the other is not H.

In some embodiments, where the compound of the invention has Formula IIa, $R^1$ and $R^2$ are each $C_{1-6}$ alkyl.

In some embodiments, where the compound of the invention has Formula IIa, $R^1$ and $R^2$ are each methyl.

In some embodiments, where the compound of the invention has Formula IIa, $R^3$ is H or $C_{1-6}$ alkyl optionally substituted with 1, 2, or 3 substituents independently selected from Cy, $C(=O)NR^{c2}R^{d2}$, and $C(=O)OR^{a2}$.

In some embodiments, where the compound of the invention has Formula IIa, $R^3$ is H, methyl, ethyl, or propyl, wherein said methyl is optionally substituted with cyclopropyl, pyridinyl, —C(=O)NHCH$_3$, —C(=O)NH(4-methylpiperazin-1-yl), or —C(=O)OH.

In some embodiments, where the compound of the invention has Formula IIa, $R^3$ is methyl.

In some embodiments, where the compound of the invention has Formula IIa, $R^3$ is ethyl.

In some embodiments, where the compound of the invention has Formula IIa, $R^5$ is H, $C_{1-6}$ alkyl, $Cy^2$, CN, NO$_2$, OR$^{a4}$, C(O)R$^{b4}$, C(O)NR$^{c4}$R$^{d4}$, S(O)$_2$R$^{b4}$, or S(O)$_2$NR$^{c4}$R$^{d4}$; wherein said $C_{1-6}$ alkyl is optionally substituted with 1, 2, 3, 4, or 5 substituents independently selected from $R^B$.

In some embodiments, where the compound of the invention has Formula IIa, $R^5$ is H, 1-methyl-1H-pyrazol-4-yl, 2-furyl, CN, NO$_2$, methoxy, —C(=O)NH$_2$, —C(=O)NH(CH$_3$), —C(=O)N(CH$_3$)$_2$, —C(=O)-(morpholin-4-yl), —C(=O)CH$_3$, —CH$_2$OH, —CH$_2$OCH$_3$, —CH$_2$NH$_2$, —CH$_2$NHSO$_2$(CH$_2$CH$_3$), —CH$_2$NHC(=O)CH$_3$, —CH(OH)CH$_3$, —SO$_2$CH$_3$, —SO$_2$CH$_2$CH$_3$, —SO$_2$-(isopropyl), —SO$_2$N(CH$_3$)$_2$, —SO$_2$NH(CH$_3$), —SO$_2$—NH(isopropyl), or —SO$_2$-(piperidin-1-yl).

In some embodiments, where the compound of the invention has Formula IIa, $R^5$ is S(O)$_2$R$^{b4}$.

In some embodiments, where the compound of the invention has Formula IIa, $R^5$ is S(O)$_2$CH$_3$.

In some embodiments, where the compound of the invention has Formula IIa, $R^5$ is S(O)$_2$CH$_2$CH$_3$.

In some embodiments, where the compound of the invention has Formula IIa, $R^5$ is —C(=O)NH$_2$.

In some embodiments, where the compound of the invention has Formula IIa, $R^5$ is —CH$_2$OCH$_3$.

In some embodiments, where the compound of the invention has Formula IIa, $R^7$ is methyl.

In some embodiments, the compound of the invention has Formula IIb:

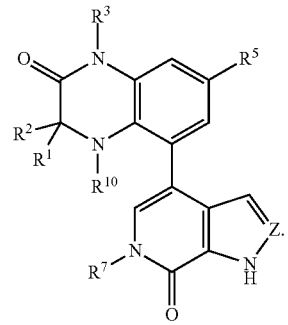

In some embodiments, where the compound of the invention has Formula IIb, Z is CH.

In some embodiments, where the compound of the invention has Formula IIb, Z is N.

In some embodiments, where the compound of the invention has Formula IIb, $R^1$ and $R^2$ are each independently selected from H, $C_{1-6}$ alkyl, and Cy$^1$, wherein said $C_{1-6}$ alkyl is optionally substituted with 1, 2, 3, 4, or 5 substituents independently selected from $R^A$;

or $R^1$ and $R^2$ together with the carbon atom to which they are attached form a $C_{3-10}$ cycloalkyl group optionally substituted with 1, 2, or 3 substituents independently selected from $R^A$.

In some embodiments, where the compound of the invention has Formula IIb, $R^1$ and $R^2$ are each independently selected from H, $C_{1-3}$ alkyl, $C_{6-10}$ aryl, $C_{3-10}$ cycloalkyl, 5-10 membered heteroaryl, and 4-10 membered heterocycloalkyl, wherein said $C_{6-10}$ aryl is optionally substituted with 1 or 2 halo, and wherein said $C_{1-3}$ alkyl is optionally substituted by OH;

or $R^1$ and $R^2$ together with the carbon atom to which they are attached form a $C_{3-6}$ cycloalkyl group.

In some embodiments, where the compound of the invention has Formula IIb, $R^1$ and $R^2$ are each independently selected from H, methyl, ethyl, propyl, cyclopropyl, cyclopentyl, pyran-4-yl, phenyl, pyridin-2-yl, 2-chloro-4-phenyl, and 2-hydroxyethyl.

In some embodiments, where the compound of the invention has Formula IIb, $R^1$ and $R^2$ together with the carbon atom to which they are attached form cyclopropyl, cyclobutyl, cyclopentyl, or cyclohexyl.

In some embodiments, where the compound of the invention has Formula IIb, $R^1$ and $R^2$ together with the carbon atom to which they are attached form cyclopropyl.

In some embodiments, where the compound of the invention has Formula IIb, one of $R^1$ and $R^2$ is H and the other is not H.

In some embodiments, where the compound of the invention has Formula IIb, $R^1$ and $R^2$ are each $C_{1-6}$ alkyl.

In some embodiments, where the compound of the invention has Formula IIb, $R^1$ and $R^2$ are each methyl.

In some embodiments, where the compound of the invention has Formula IIb, $R^3$ is H or $C_{1-6}$ alkyl.

In some embodiments, where the compound of the invention has Formula IIb, $R^3$ is H or methyl.

In some embodiments, where the compound of the invention has Formula IIb, $R^5$ is H or S(O)$_2$R$^{b4}$.

In some embodiments, where the compound of the invention has Formula IIb, $R^5$ is H or —SO$_2$CH$_3$.

In some embodiments, where the compound of the invention has Formula IIb, $R^5$ is H or —SO$_2$CH$_2$CH$_3$.

In some embodiments, where the compound of the invention has Formula IIb, R⁷ is methyl.

In some embodiments, where the compound of the invention has Formula IIb, R¹⁰ is H.

In some embodiments, the compound of the invention has Formula IIIa or IIIb:

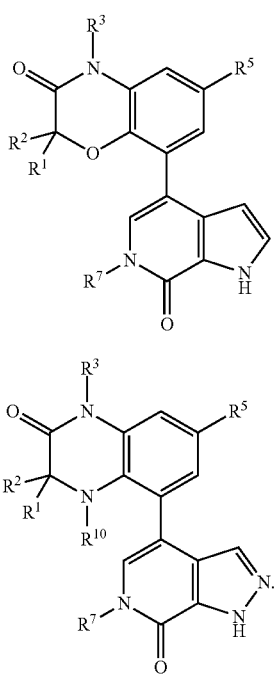

IIIa

IIIb

In some embodiments, where the compound of the invention has Formula IIIa or IIIb, R¹ and R² are each independently selected from H, $C_{1-6}$ alkyl, and $Cy^1$, wherein said $C_{1-6}$ alkyl is optionally substituted with 1, 2, 3, 4, or 5 substituents independently selected from $R^4$;

or R¹ and R² together with the carbon atom to which they are attached form a $C_{3-10}$ cycloalkyl group optionally substituted with 1, 2, or 3 substituents independently selected from $R^4$.

In some embodiments, where the compound of the invention has Formula IIIa or IIIb, R¹ and R² are each independently selected from H, $C_{1-3}$ alkyl, $C_{6-10}$ aryl, $C_{3-10}$ cycloalkyl, 5-10 membered heteroaryl, and 4-10 membered heterocycloalkyl, wherein said $C_{6-10}$ aryl is optionally substituted with 1 or 2 halo, and wherein said $C_{1-3}$ alkyl is optionally substituted by OH;

or R¹ and R² together with the carbon atom to which they are attached form a $C_{3-6}$ cycloalkyl group.

In some embodiments, where the compound of the invention has Formula IIIa or IIIb, R¹ and R² are each independently selected from H, methyl, ethyl, propyl, cyclopropyl, cyclopentyl, pyran-4-yl, phenyl, pyridin-2-yl, 2-chloro-4-phenyl, and 2-hydroxyethyl.

In some embodiments, where the compound of the invention has Formula IIIa or IIIb, R¹ and R² together with the carbon atom to which they are attached form cyclopropyl, cyclobutyl, cyclopentyl, or cyclohexyl.

In some embodiments, where the compound of the invention has Formula IIIa or IIIb, R¹ and R² together with the carbon atom to which they are attached form cyclopropyl.

In some embodiments, where the compound of the invention has Formula IIIa or IIIb, one of R¹ and R² is H and the other is not H.

In some embodiments, where the compound of the invention has Formula IIIa or IIIb, R¹ and R² are each $C_{1-6}$ alkyl.

In some embodiments, where the compound of the invention has Formula IIIa or IIIb, R¹ and R² are each methyl.

In some embodiments, where the compound of the invention has Formula IIIa or IIIb, R³ is H or $C_{1-6}$ alkyl optionally substituted with 1, 2, or 3 substituents independently selected from Cy, C(=O)NR$^{c2}$R$^{d2}$, and C(=O)OR$^{a2}$.

In some embodiments, where the compound of the invention has Formula IIIa or IIIb, R³ is H, methyl, ethyl, or propyl, wherein said methyl is optionally substituted with cyclopropyl, pyridinyl, —C(=O)NHCH₃, —C(=O)NH(4-methylpiperazin-1-yl), or —C(=O)OH.

In some embodiments, where the compound of the invention has Formula IIIa or IIIb, R³ is methyl.

In some embodiments, where the compound of the invention has Formula IIIa or IIIb, R⁵ is H, $C_{1-6}$ alkyl, $Cy^2$, CN, NO₂, OR$^{a4}$, C(O)R$^{b4}$, C(O)NR$^{c4}$R$^{d4}$, S(O)₂R$^{b4}$, or S(O)₂NR$^{c4}$R$^{d4}$; wherein said $C_{1-6}$ alkyl is optionally substituted with 1, 2, 3, 4, or 5 substituents independently selected from $R^B$.

In some embodiments, where the compound of the invention has Formula IIIa or IIIb, R⁵ is H, 1-methyl-1H-pyrazol-4-yl, 2-furyl, CN, NO₂, methoxy, —C(=O)NH₂, —C(=O)NH(CH₃), —C(=O)N(CH₃)₂, —C(=O)-(morpholin-4-yl), —C(=O)CH₃, —CH₂OH, —CH₂OCH₃, —CH₂NH₂, —CH₂NHSO₂(CH₂CH₃), —CH₂NHC(=O)CH₃, —CH(OH)CH₃, —SO₂CH₃, —SO₂CH₂CH₃, —SO₂-(isopropyl), —SO₂N(CH₃)₂, —SO₂NH(CH₃), —SO₂—NH(isopropyl), or —SO₂-(piperidin-1-yl).

In some embodiments, where the compound of the invention has Formula IIIa or IIIb, R⁵ is S(O)₂R$^{b4}$.

In some embodiments, where the compound of the invention has Formula IIIa or IIIb, R⁵ is S(O)₂CH₃.

In some embodiments, where the compound of the invention has Formula IIIa or IIIb, R⁵ is S(O)₂CH₂CH₃.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{i-j}$" indicates a range which includes the endpoints, wherein i and j are integers and indicate the number of carbons. Examples include $C_{1-4}$, $C_{1-6}$, and the like.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

The term "carbon" refers to one or more carbon atoms.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i\text{-}j}$ alkoxy," employed alone or in combination with other terms, refers to a group of formula —O-alkyl, wherein the alkyl group has i to j carbons. In some embodiments, the alkyl group of the alkoxy group has 1 to 3 carbon atoms. Example alkoxy groups include methoxy, ethoxy, and propoxy (e.g., n-propoxy and isopropoxy).

As used herein, "$C_{i\text{-}j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i\text{-}j}$ alkynyl," employed alone or in combination with other terms, refers to an unsaturated hydrocarbon group having one or more triple carbon-carbon bonds and having i to j carbons. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, the term "$C_{i\text{-}j}$ alkylamino," employed alone or in combination with other terms, refers to a group of formula —NH(alkyl), wherein the alkyl group has i to j carbon atoms. In some embodiments, the alkyl group has 1 to 6, 1 to 4, or 1 to 3 carbon atoms. Example alkylamino groups include, but are not limited to, methylamino, ethylamino, and propylamino.

As used herein, the term "di-$C_{i\text{-}j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6, 1 to 4, or 1 to 3 carbon atoms. In some embodiments, the dialkylamino group is —N($C_{1\text{-}4}$ alkyl)$_2$ such as, for example, dimethylamino, diethylamino, N-methyl-N-ethylamino, or N-methyl-N-propylamino.

As used herein, the term "$C_{i\text{-}j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1\text{-}4}$ alkylthio such as, for example, methylthio or ethylthio.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2 or more fused rings) aromatic hydrocarbon, such as, but not limited to, phenyl, 1-naphthyl, 2-naphthyl, and the like. In some embodiments, aryl is $C_{6\text{-}10}$ aryl. In some embodiments, the aryl group is a naphthalene ring or phenyl ring. In some embodiments, the aryl group is phenyl.

As used herein, the term "$C_{i\text{-}j}$ cycloalkyl," employed alone or in combination with other terms, refers to a non-aromatic cyclic hydrocarbon moiety having i to j ring-forming carbon atoms, which may optionally contain one or more alkenylene groups (—C=C—) as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3\text{-}10}$ cycloalkyl, $C_{3\text{-}7}$ cycloalkyl, $C_{3\text{-}6}$ cycloalkyl, or $C_{5\text{-}6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, and the like. Further exemplary cycloalkyl groups include cyclopropyl, cyclobutyl, cyclopentyl, and cyclohexyl. Further exemplary cycloalkyl groups include cyclopropyl.

As used herein, "$C_{i\text{-}j}$ haloalkoxy," employed alone or in combination with other terms, refers to a group of formula —O-haloalkyl having i to j carbon atoms. In some embodiments, the haloalkoxy group is fluorinated only. In some embodiments, the alkyl group has 1 to 6, 1 to 4, or 1 to 3 carbon atoms. In some embodiments, the haloalkoxy group is $C_{1\text{-}4}$ haloalkoxy. An example haloalkoxy group is $OCF_3$. An additional example haloalkoxy group is $OCHF_2$.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i\text{-}j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the alkyl group has 1 to 6 or 1 to 4 carbon atoms. In some embodiments, the haloalkyl group is fluoromethyl, difluoromethyl, or trifluoromethyl. In some embodiments, the haloalkyl group is trifluoromethyl.

As used herein, the term "heteroaryl," employed alone or in combination with other terms, refers to a monocyclic or polycyclic (e.g., having 2 or more fused rings) aromatic heterocylic moiety, comprising carbon atoms and one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered.

When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1, 2-b]thiazole, purine, triazine, and the like.

A 5-membered heteroaryl is a heteroaryl group having five ring-forming atoms comprising wherein one or more of the ring-forming atoms are independently selected from N, O, and S. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1, 2, 4-triazolyl, 1, 2, 4-thiadiazolyl, 1, 2, 4-oxadiazolyl, 1, 3, 4-triazolyl, 1, 3, 4-thiadiazolyl, and 1, 3, 4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heterocycloalkyl," employed alone or in combination with other terms, refers to non-aromatic heterocyclic ring system, which may optionally contain one or more unsaturations as part of the ring structure, and which comprises carbon atoms and at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered, 4- to 10-membered, 4- to 7-membered, 4-membered, 5-membered, 6-membered, or 7-membered. Examples of heterocycloalkyl groups include 1, 2, 3, 4-tetrahydro-quinoline, dihydrobenzofuran, azetidine, azepane, pyrrolidine, piperidine, piperazine, morpholine, thiomorpholine, and pyran.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

The following abbreviations may be used herein: AcOH (acetic acid); Ac$_2$O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA (N,N-diisopropylethylamine); DIBAL (diisobutylaluminium hydride); DMF (N,N-dimethylformamide); Et (ethyl); EtOAc (ethyl acetate); FCC (flash column chromatography); g (gram(s)); h (hour(s)); HATU (N,N,N',N'-tetramethyl-O-(7-azabenzotriazol-1-yl) uronium hexafluorophosphate); HCl (hydrochloric acid); HPLC (high performance liquid chromatography); Hz (hertz); J (coupling constant); LCMS (liquid chromatography—mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); s (singlet); t (triplet or tertiary); TBS (tert-butyldimethylsilyl); tert (tertiary); tt (triplet of triplets); TFA (trifluoroacetic acid); THF (tetrahydrofuran); µg (microgram(s)); µL (microliter(s)); µM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety.

Compounds of the invention can be prepared as shown in Scheme I. The intermediate (i), where $X^1$ is halo, can be coupled with (ii), where M is a boronic acid, boronic ester, or an appropriately substituted metal such as Sn(Bu)$_4$ or Zn, under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a protected derivative (iii). The protecting group (e.g., P is tosyl or SEM) can be removed under standard conditions (e.g., NaOH for tosyl deprotection and TFA for SEM deprotection) to give compounds of the invention.

Alternatively, the $X^1$ halo group of (i) can be converted to an appropriate substituted metal (iv) (e.g., M is B(OH)$_2$, Sn(Bu)$_4$, or Zn) and then coupled to a heterocyclic halide (v) ($X^1$ is halo) under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give protected derivative (iii) which can be deprotected to yield compounds of the invention.

tions or standard Stille conditions as mentioned above to give a protected derivative (vi). Alternatively, introduction of $R^3$ via alkylation can be carried out after the formation of derivative (vi). For example, pyridone (vi) can be alkylated

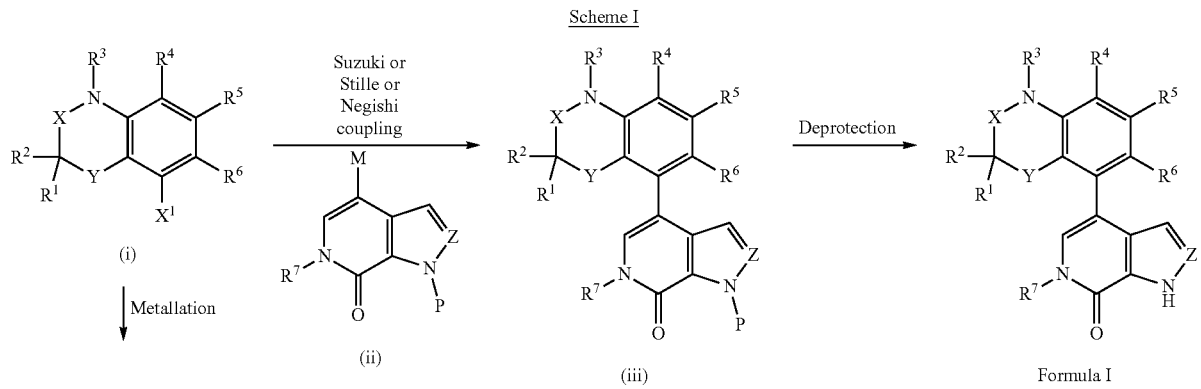

Scheme I

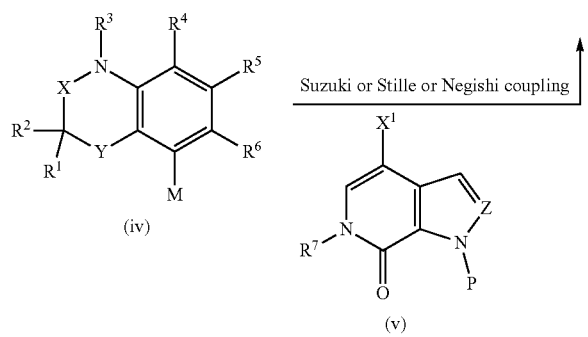

Compounds of the invention can be prepared as shown in Scheme II. The nitro-phenol (i) can be halogenated with suitable reagents, such as N-chlorosuccinimide, N-bromosuccinimide, $Br_2$ or N-iodosuccinimide to give a halide where $X^1$=Cl, Br or I, and subsequent reduction of the nitro group under standard conditions (e.g., Fe or Zn) can give the amino intermediate (ii). Alkylation of (ii) with $X^2C(=O)C(R^1R^2)$—Br (iii), where $X^2$ is $C_{1-4}$ alkoxy such as ethoxy, using standard alkylating conditions can give an ether which can cyclize in situ or upon heating to afford the bicyclic derivative (iv). Alternatively, acylation of the amine of (ii) with $BrC=OCR^1R^2$—Br (iii) under standard acylating conditions can give an amide which can cyclize in situ or upon heating to afford the bicyclic derivative (iv). After an optional N-akylation step to introduce $R^3$, the compounds (iv) can be coupled with intermediates (v), where M is a boronic acid, boronic ester, or an appropriately substituted metal such as $Sn(Bu)_4$ or Zn, under standard Suzuki condiby reacting with $R^3$—$X^1$, where $X^1$=halo (Br, Cl, or I), and a base, such as triethylamine, NaH or $Na_2CO_3$, and subsequently deprotecting under standard conditions conditions (e.g., NaOH for tosyl deprotection and TFA for SEM deprotection) to afford compounds of the invention (vii).

Optionally, reduction of the carbonyl of (iv) with a reducing agent, such as borane, followed by alkylation with $R^3$—$X^1$ and a base can give compounds of the invention (ix). These compounds can be coupled with (v) under standard Suzuki conditions or standard Stille conditions to give a protected derivative which can be subsequently deprotected under standard conditions to afford compounds of the invention (viii).

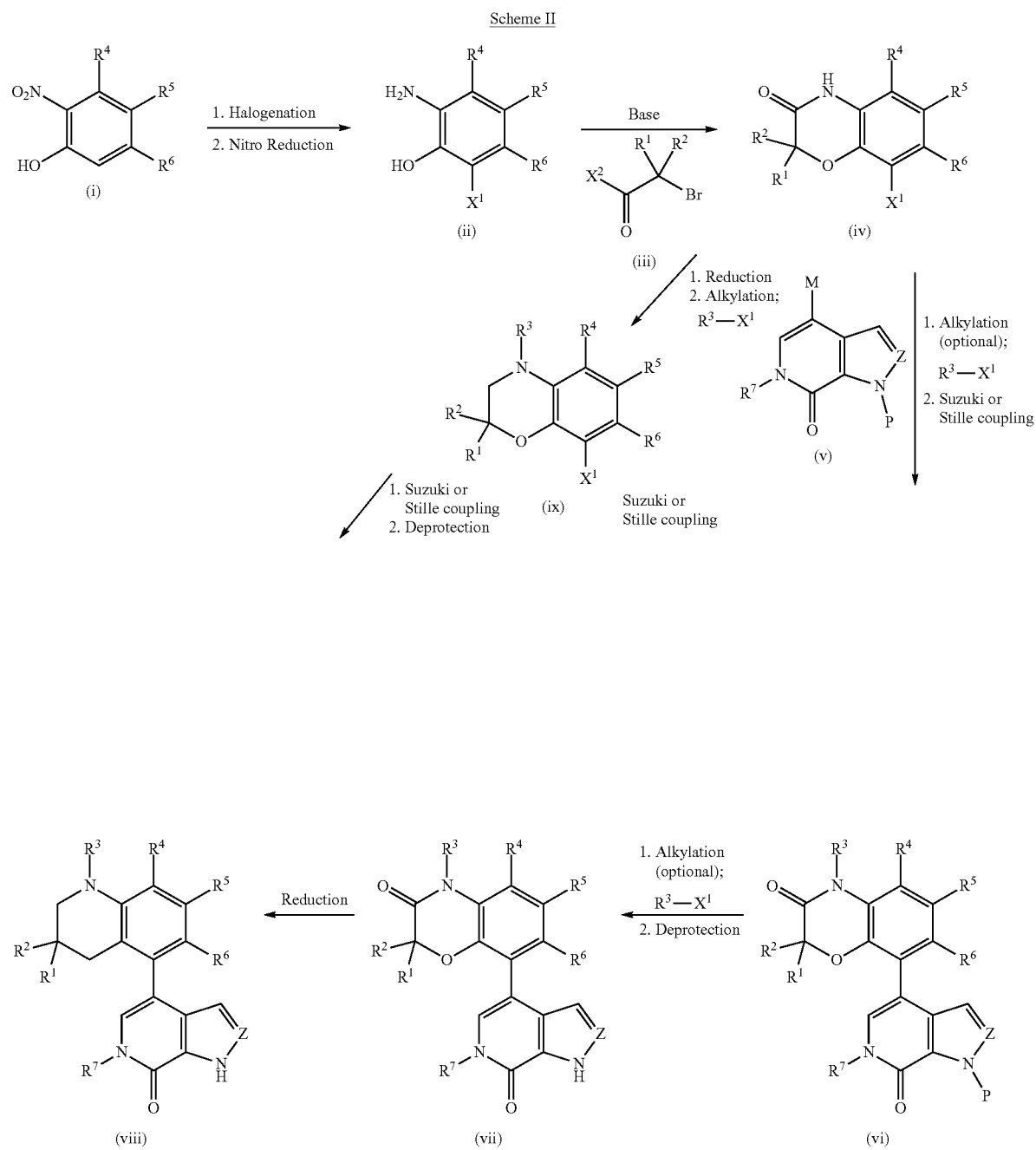

Scheme II

Compounds of the invention can be formed as shown in Scheme III. The nitro compound (i) can be halogenated with suitable reagents, such as N-chlorosuccinimide, N-bromosuccinimide or $Br_2$ or N-iodosuccinimide to give a halide where $X^1$=Cl, Br or I. Reaction of the nitro-halide (ii) with an ester (iii), such as $RO_2CCR^1R^2$—$Y^1$ (where R is $C_{1-4}$ alkyl and $Y^1$ is OH or $NR^{10}$), can give a nitro-intermediate derivative which upon reduction of the nitro group under standard conditions (e.g., Fe or Zn) can give the corresponding amine which can then cyclize in situ or upon heating to afford bicyclic derivative (iv). The intermediate (iv) can be coupled to (v), where M is a boronic acid, boronic ester or an appropriately substituted metal such as $Sn(Bu)_4$ or Zn, under standard Suzuki conditions or standard Stille condi- tions to give protected derivative (vi). Pyridone (vi) can be alkylated by reactiong with $R^3$—$X^1$ where $X^1$=Br, Cl, or I and a base, such as triethylamine, NaH or $Na_2CO_3$. Then deprotection can be carried out under standard conditions to afford compounds of the invention (vii).

Optionally, compound (iv) can be first alkylated with $R^3$—$X^1$, then coupled to (v), under standard Suzuki conditions or standard Stille conditions to give a protected derivative (vi). Then deprotection can be carried out under standard conditions to afford compounds of the invention (vii). Reduction of the carbonyl of (vii) with a reducing agent, such as borane, can give compounds of the invention (viii).

Scheme III

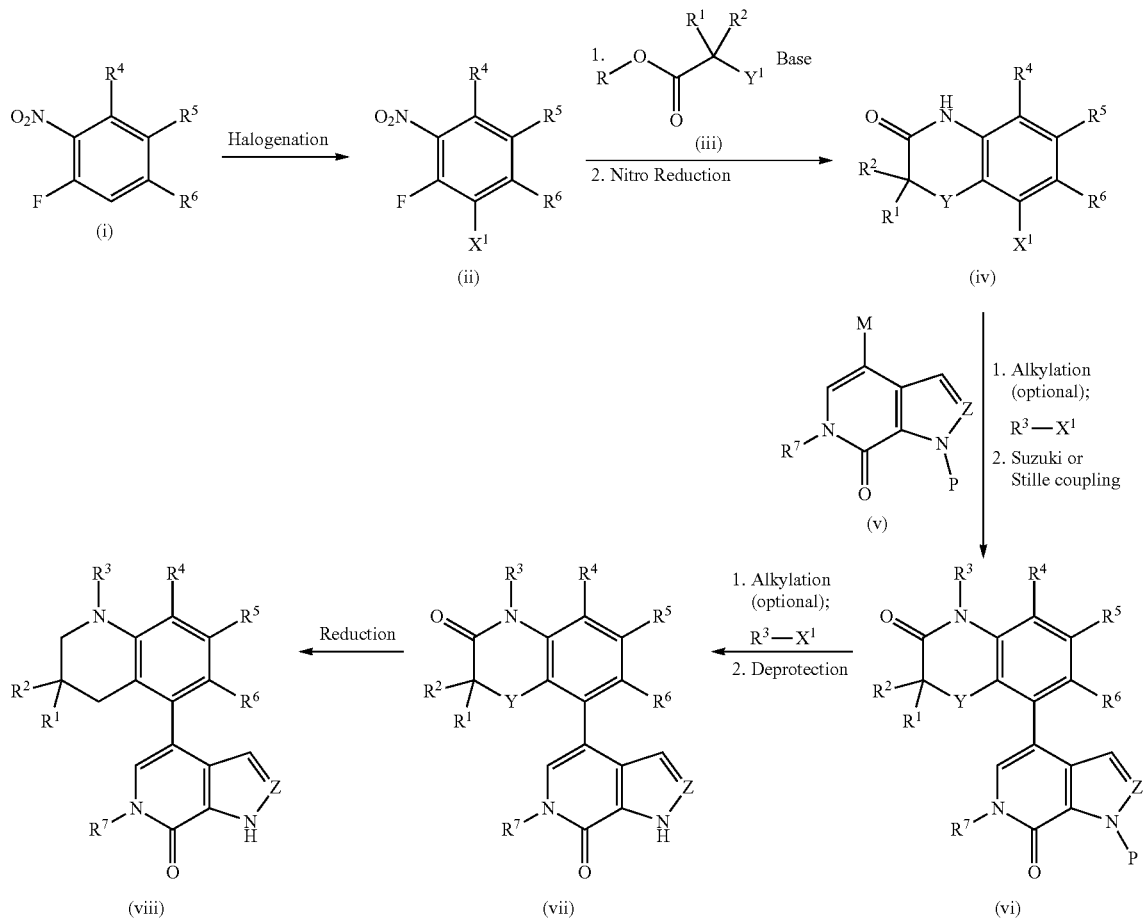

Intermediates for making compounds of the invention can be prepared as shown in Scheme IV. A thiophenol (i) can be alkylated with $R^{b4}X^1$ (where $X^1$=Br, Cl, or I) and a base, such as triethylamine, NaH or $Na_2CO_3$) to afford a thioether which can be oxidized with a suitable reagent, such as mCPBA or $H_2O_2$ or dioxirane, to give the sulfoxide which can be further oxidized with an oxidant, such as mCPBA or $H_2O_2$ or dioxirane, to give a sulfone (ii). The sulfone (ii) can be nitrated under standard conditions (e.g., $HNO_3$ with or without Fe or $H_2SO_4$ catalyst) to give a nitro-phenol (iii). Compounds of the invention can be synthesized from intermediates (iii) using the methods described in Scheme II.

Scheme IV

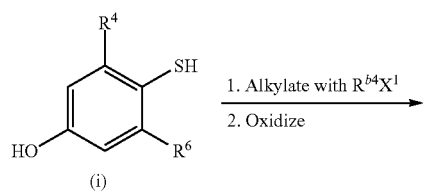

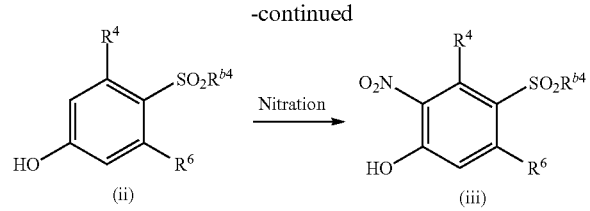

Compounds of the invention can be prepared as shown in Scheme V. A cyanophenol (i) can be reduced with suitable reagents (e.g., $LiBH_4$ or borane) to give amines (ii) which can be acylated, arylated or alkylated under standard conditions. Alternatively, cyanophenol (i) can be reduced to an aldehyde (v) with a reducing agent, such as DIBAL, and then reductively aminated under standard conditions (e.g., $NaCNBH_4$, HNRR where each R is independently, e.g., $C_{1-6}$ alkyl, $-C(=O)(C_{1-6}$ alkyl), cycloalkyl, heterocycloalkyl, aryl, heteroaryl, or substituted derivatives thereof and the like) to give an amino derivative (iii). The aldehyde (v) can also be alkylated under standard conditions (e.g., Grignard reagent of formula $R-MgX^1$ ($X^1$=halo)) to give an alcohol (vi) which can be converted to a leaving group, such as a mesylate, and displaced with an amine, HNRR, to give a derivative (iii). In addition, cyanophenol (i) can be hydrolyzed to its carboxylic acid (iv) and then coupled to an amine, HNRR, using standard amide coupling agents (e.g., HBTU, HATU or EDC) to give an amide (vii). Compounds of the invention can be synthesized from these nitrophenol derivatives (i-vii) using the methods described in Scheme II.

Scheme V

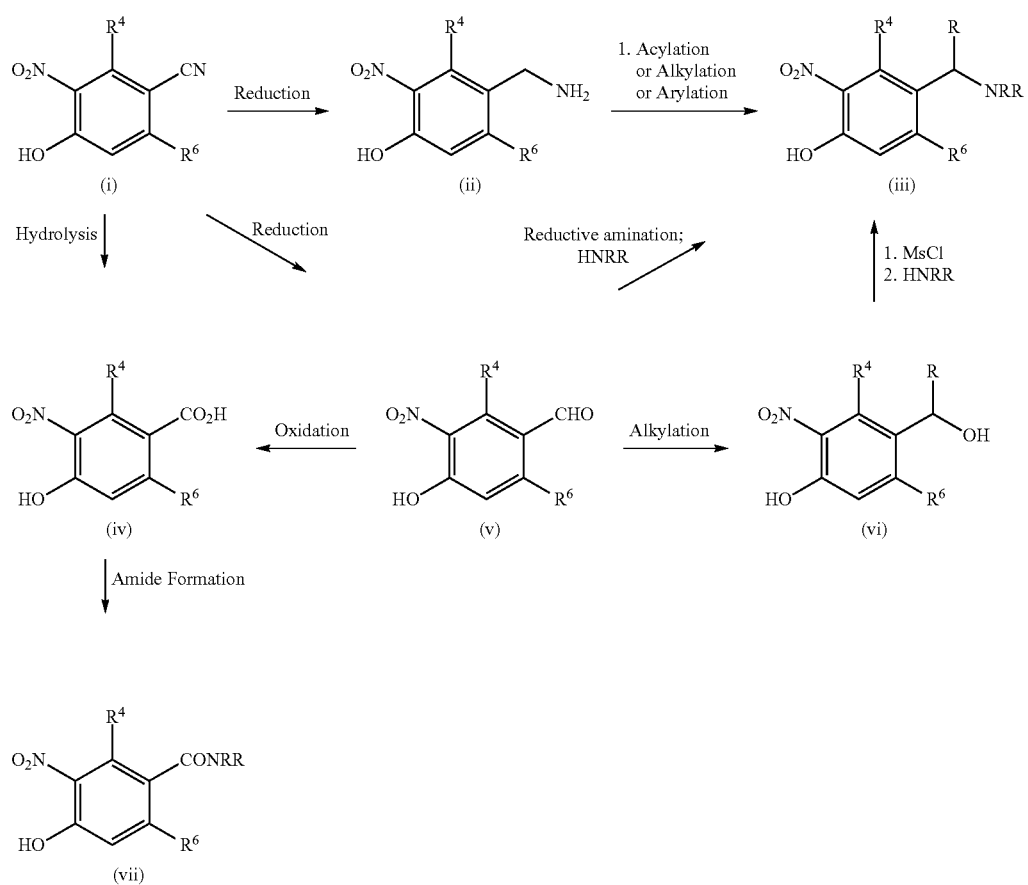

Compounds of the invention can be prepared as shown in Scheme VI. The halide derivative (i) can be coupled to M-$R^5$, where M is a boronic acid, boronic ester or an appropriately substituted metal $Sn(Bu)_4$ or Zn—$R^5$ under standard Suzuki conditions or standard Stille conditions to give a derivative (ii). M-$R^5$ can also be an amine containing heterocycle (where M is H and is attached to the amine nitrogen of heterocycle $R^5$) with coupling to the halide of (i) being performed by heating with a base or under Buchwald/Hartwig conditions (e.g., in the presence of a palladium(0) catalyst, such as tetrakis(triphenylphosphine)palladium(0) and a base (e.g., an alkoxide base)) to give derivative (ii). Compounds of the invention can be synthesized from (ii) using the methods described in Scheme II.

Scheme VI

Suzuki or Heck or Stille or Negishi or Buchwald/Hartwig Coupling

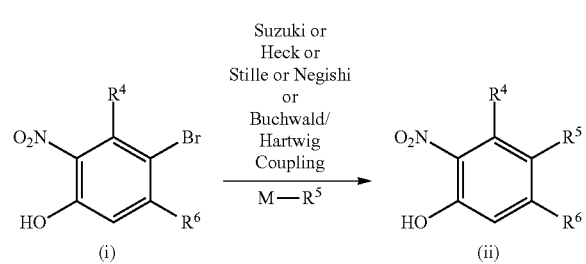

Intermediates for preparing compounds of the invention can be made as shown in Scheme VII. Pyridyl derivative (i) can be reacted with 1,1-dimethoxy-N,N-dimethylmethanamine to give olefin (ii). Reduction of the nitro group under standard conditions (e.g., Fe or Zn) gives an amino compound which may cyclize in situ or upon heating to afford a bicyclic derivative (iii). The amino group of (iii) can be protected with a suitable protecting group P, where for example P is tosyl or SEM, under standard conditions (e.g., tosyl-Cl or SEM-Cl) to give the protected heterocycle (iv). Acid hydrolysis of the ether and alkylation of the amide with $R^7$—$X^1$ under standard conditions (where $X^1$=halo) and a base, such as triethylamine, NaH or $Na_2CO_3$) can afford pyridone (v). Conversion of the bromide of (v) to a metal (e.g., M is $B(OR)_2$, $SnR_3$, Zn) under standard conditions can give intermediates (vi). Compounds of the invention can be synthesized from (vi) using methods described in Scheme I-III. (See also, WO 2013/097601, p. 92), Scheme VII

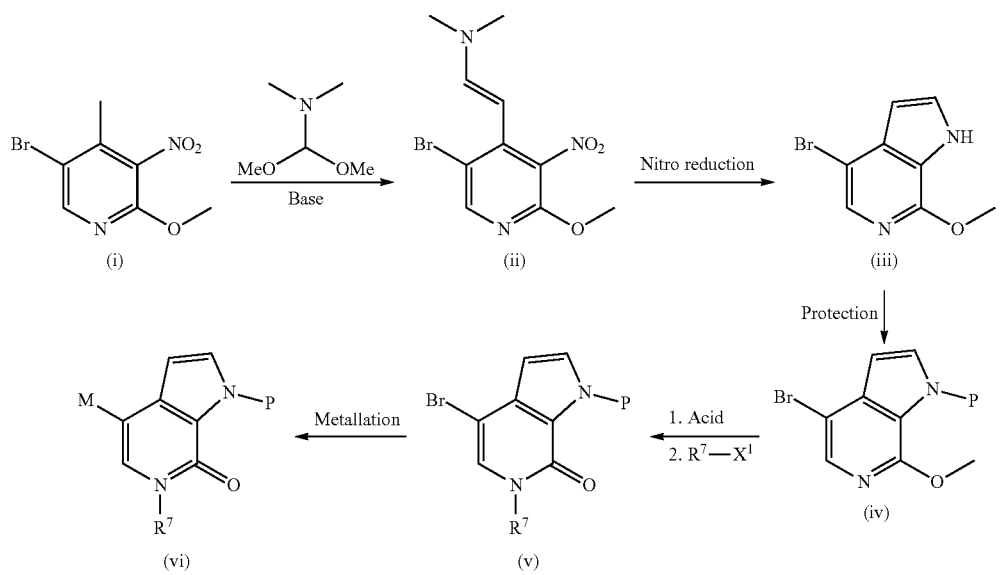

Intermediates for the preparation of compounds of the invention can be made as shown in Scheme VIII. Pyridyl derivative (i) can be alkylated with R—$X^1$ under standard conditions (where $X^1$=Br, Cl, or I) and a base, such as triethylamine, NaH or $Na_2CO_3$) to give a pyridone (ii). Reduction of the nitro of (ii) under standard conditions (e.g., Fe or Zn) can give an amino compound which upon reaction with amyl nitrite can cyclize in situ or upon heating to afford a bicyclic derivative (iv). The heterocyclic amine (iv) can be protected with a suitable protecting group under standard conditions (e.g., tosyl-Cl or SEM-Cl) to give the protected heterocycle (v). Conversion of the bromide (v) to a metal M (e.g., M is $B(OR)_2$, $SnR_3$, Zn) under standard conditions can give intermediates (vi). Compounds of the invention can be synthesized from intermediate (vi) using methods described in Scheme I-III. (See also, WO 2013/097601, p. 92).

Scheme VIII

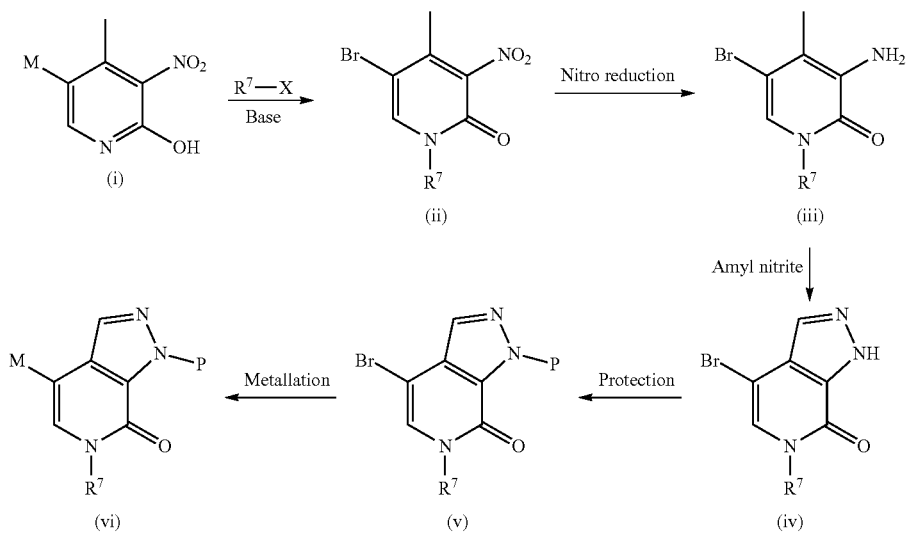

For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry, Vols.* 1-107 (Elsevier, 1963-2012); *Journal of Heterocyclic Chemistry Vols.* 1-49 (Journal of Heterocyclic Chemistry, 1964-2012); Carreira, et al. (Ed.) Science of Synthesis, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

Methods of Use

Compounds of the invention are BET protein inhibitors and, thus, are useful in treating diseases and disorders associated with activity of BET proteins. For the uses described herein, any of the compounds of the invention, including any of the embodiments thereof, may be used.

The compounds of the invention can inhibit one or more of BET proteins BRD2, BRD3, BRD4, and BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

The compounds of the invention are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of the invention include, but are not limited to, cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a BET-mediated disease or disorder. Also provided is the use of a compound of the invention, or any of the embodiments thereof, or a pharmaceutical composition thereof, in the manufacture of a medicament for treating a BET-mediated disease or disorder.

Diseases that can be treated with the compounds of the invention include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, acute myeloid leukemia (AML), diffuse large B-cell lymphoma (DLBCL), ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

In some embodiments, the cancer is a hematological cancer.

In some embodiments, the cancer is multiple myeloma, acute myeloid leukemia (AML), or diffuse large B-cell lymphoma (DLBCL).

The diseases treatable using the compounds of the invention also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of the invention also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of the invention also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of the invention also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with the compounds of the invention include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, the compounds of the invention are indicated for the treatment of human papilloma virus infections of skin or cervical epithelia.

The diseases and conditions that can be treated with the compounds of the invention also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of the invention are also useful in the treatment of disorders of lipid metabolism via the regulation of APO-A1 such as hypercholesterolemia, atherosclerosis and Alzheimer's disease.

The compounds of the invention are also useful in the treatment of fibrotic conditions such as idiopathic pulmonary fibrosis, renal fibrosis, post-operative stricture, keloid formation, scleroderma and cardiac fibrosis.

The compounds of the invention can also be used to treat ophthamological indications such as dry eye.

The compounds of the invention can also be used to treat heart disease such as heart failure.

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially. In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paromomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

In some embodiments, the compounds of the invention are administered in combination with a JAK kinase inhibitor (e.g., ruxolitinib, tofacitinib, baricitinib, CYT387, GLPG0634, lestaurtinib, pacritinib, TG101348, or a JAK1-selective inhibitor), a Pim kinase inhibitor (including inhibitors of one or more of PIM1, PIM2, and PIM3), a PI3 kinase inhibitor including PI3K-delta selective and broad spectrum PI3K inhibitors, an MEK inhibitor, a cyclin dependent kinase inhibitor, a b-RAF inhibitor, an mTOR inhibitor, a proteasome inhibitor (e.g., bortezomib, carfilzomib), an HDAC-inhibitor (e.g., panobinostat, vorinostat), a DNA methyl transferase inhibitor, dexamethasone, melphalan, or an immunomodulator (e.g., lenolidomide, pomalidomide).

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated.

Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate. The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating BET proteins in tissue samples, including human, and for identifying BET protein ligands by inhibition binding of a labeled compound. Accordingly, the present invention includes BET protein assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro BET protein labeling and competition assays, compounds that incorporate $^3H$, $^{14}C$, $^{82}Br$, $^{125}I$, $^{131}I$, or $^{35}S$ will generally be most useful.

For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled.

Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J Combi. Chem., 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1. 8-(6-methyl-7-oxo-6,7-dihydro-1H-pyrrolo[2,3-c]pyridin-4-yl)-2-phenyl-2H-1,4-benzoxazin-3(4H)-one

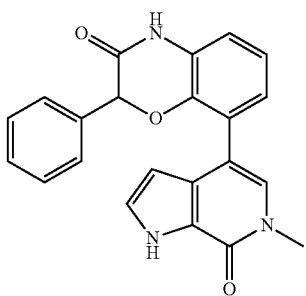 [SMILES: Cn1cc(-c2cccc3c2OC(c2ccccc2)C(=O)N3)c2cc[nH]c2c1=O]

Step 1.
8-bromo-2-phenyl-2H-1,4-benzoxazin-3(4H)-one

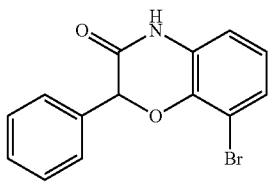 [SMILES: O=C1Nc2cccc(Br)c2OC1c1ccccc1]

2-Amino-6-bromophenol (0.10 g, 0.53 mmol) (Frinton cat# FR-2404) and α-bromo-benzeneacetic acid methyl ester (0.084 mL, 0.53 mmol) (Aldrich cat#365270) were combined with N-methylpyrrolidinone (2.0 mL) and 1,8-diazabicyclo[5.4.0]undec-7-ene (0.080 mL, 0.53 mmol) in a sealed tube. The mixture was heated to 140° C. in the microwave for 5 minutes. The reaction mixture was then cooled, dissolved in ethyl acetate, and washed with 1 N HCl, brine, dried over magnesium sulfate, and concentrated to give a dark oil. The product was purified by FCC on silica gel eluting a hexane: ethyl acetate gradient to afford 8-bromo-2-phenyl-2H-1,4-benzoxazin-3(4H)-one as a semisolid (0.1 g, 60%). LCMS calculated for $C_{14}H_{11}BrNO_2$ (M+H)$^+$: m/z=304.0, 306.0; found: 303.8, 305.8.

Step 2. 8-{6-methyl-1-[(4-methylphenyl)sulfonyl]-7-oxo-6,7-dihydro-1H-pyrrolo[2,3-c]pyridin-4-yl}-2-phenyl-2H-1,4-benzoxazin-3(4H)-one

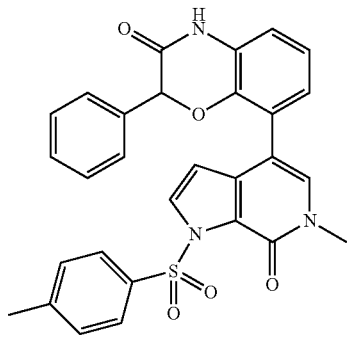

8-Bromo-2-phenyl-2H-1,4-benzoxazin-3(4H)-one (0.02 g, 0.06 mmol) was combined with 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (0.028 g, 0.066 mmol) (WO2013097601, p. 92) in a mixture of 1,4-dioxane (1.5 mL) and potassium carbonate (0.018 g, 0.13 mmol) in water (0.50 mL). The reaction was degassed with nitrogen and the catalyst [1,1'-bis(diphenylphosphino)ferrocene]dichloropalladium(II) complex with dichloromethane (1:1) (0.005 g, 0.006 mmol) was added. The reaction was heated in a sealed tube to 100° C. for 2 h. The mixture was cooled to room temperature and was partitioned between ethyl acetate and water. The organic layer was washed with brine, dried over magnesium sulfate, and concentrated to afford 8-{6-methyl-1-[(4-methylphenyl)sulfonyl]-7-oxo-6,7-dihydro-1H-pyrrolo[2,3-c]pyridin-4-yl}-2-phenyl-2H-1,4-benzoxazin-3(4H)-one (0.025 g, 83%) as a dark oil. LCMS calculated for $C_{29}H_{24}N_3O_5S$ (M+H)$^+$: m/z=526.1; found: 526.1.

Step 3. 8-(6-methyl-7-oxo-6,7-dihydro-1H-pyrrolo[2,3-c]pyridin-4-yl)-2-phenyl-2H-1,4-benzoxazin-3(4H)-one 8-{6-Methyl-1-[(4-methylphenyl) sulfonyl]-7-oxo-6,7-dihydro-1H-pyrrolo[2,3-c]pyridin-4-yl}-2-phenyl-2H-1,4-benzoxazin-3(4H)-one was dissolved in a mixture of ethanol (3.0 mL) and 1.0 M sodium hydroxide in water (1.0 mL) and heated to 80° C. in an oil bath for 1 h. The mixture was then cooled to room temperature and acidified with trifluoroacetic acid (TFA). The product was purified by prep HPLC on a C-18 column eluting a water:acetonitrile gradient buffered at pH 2 with TFA, to afford the title product as an off white amorphous solid (25 mg). LCMS calculated for $C_{22}H_{18}N_3O_3$ (M+H)$^+$: m/z=372.1; found: 372.1. $^1$H NMR (400 MHz, DMSO-d$_6$) δ 11.98 (s, 1H), 11.03 (s, 1H), 7.28 (ddd, J=8.5, 6.4, 3.9 Hz, 5H), 7.17 (t, J=2.8 Hz, 1H), 7.06 (s, 1H), 7.05-6.89 (m, 3H), 6.02-5.95 (m, 1H), 5.73 (s, 1H), 3.47 (s, 3H).

Examples 2-4

The compounds of Example 2-4 and the experimental procedures used to prepare them are set out in Table 1 below.

TABLE 1

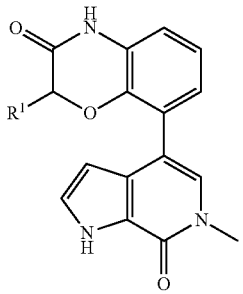

| Ex. No. | Name | R¹ | Synthetic Procedure |
|---|---|---|---|
| 2 | 2-isopropyl-8-(6-methyl-7-oxo-6,7-dihydro-1H-pyrrolo[2,3-c]pyridin-4-yl)-2H-1,4-benzoxazin-3(4H)-one | i-Prop | Ex. No. 1 |
| 3 | 2-methyl-8-(6-methyl-7-oxo-6,7-dihydro-1H-pyrrolo[2,3-c]pyridin-4-yl)-2H-1,4-benzoxazin-3(4H)-one | Me | Ex. No. 1 |
| 4 | 2-ethyl-8-(6-methyl-7-oxo-6,7-dihydro-1H-pyrrolo[2,3-c]pyridin-4-yl)-2H-1,4-benzoxazin-3(4H)-one | Et | Ex. No. 1 |

Example 5. 8-(6-methyl-7-oxo-6,7-dihydro-1H-pyrrolo[2,3-c]pyridin-4-yl)-2-pyridin-2-yl-2H-1,4-benzoxazin-3(4H)-one 2,2,2-trifluoroacetate

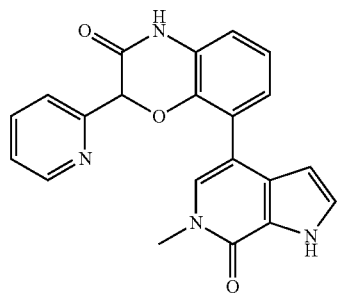 [SMILES: Cn1cc(-c2cccc3c2OC(c2ccccn2)C(=O)N3)c2cc[nH]c2c1=O]

Step 1. Methyl bromo(pyridin-2-yl)acetate

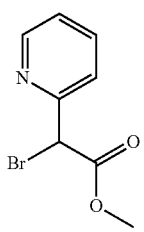

Benzoyl peroxide (80 mg, 0.3 mmol) was added in one portion to a solution of methyl 2-pyridylacetate (500 mg, 3 mmol) (Aldrich cat#M78305) and N-bromosuccinimide (600 mg, 3 mmol) in carbon tetrachloride (5 mL). The reaction was heated to 100° C. for 1 h, cooled to room temperature, and filtered to remove the solids. The solvent was evaporated to afford methyl bromo(pyridin-2-yl)acetate as dark yellow semi-solid. LCMS calculated for $C_8H_9BrNO_2$ $(M+H)^+$: m/z=229.9, 231.9; found=229.9, 231.8.

Step 2. 8-bromo-2-pyridin-2-yl-2H-1,4-benzoxazin-3(4H)-one

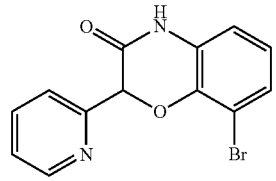 [SMILES: O=C1Nc2cccc(Br)c2OC1c1ccccn1]

A mixture of 2-amino-6-bromophenol (100 mg, 0.5 mmol), methyl bromo(pyridin-2-yl)acetate (100 mg, 0.5 mmol) and 1,8-diazabicyclo[5.4.0]undec-7-ene (80 μL, 0.5 mmol) in N-methylpyrrolidinone (3 mL) was heated in microwave at 140° C. for 10 min. The reaction was allowed to cool, was diluted with ethyl acetate and washed with water. The combined organic layers were washed with brine, dried over $MgSO_4$, filtered, and concentrated to afford 8-bromo-2-pyridin-2-yl-2H-1,4-benzoxazin-3(4H)-one (0.15 g, 90%) as a crude product. LCMS calculated for $C_{13}H_{10}BrN_2O_2(M+H)^+$: m/z=304.9 306.9; found=305.0, 307.0.

Step 3. 8-{6-methyl-1-[(4-methylphenyl)sulfonyl]-7-oxo-6,7-dihydro-H-pyrrolo[2,3-c]pyridin-4-yl}-2-pyridin-2-yl-2H-1,4-benzoxazin-3(4H)-one 2,2,2-trifluoroacetate

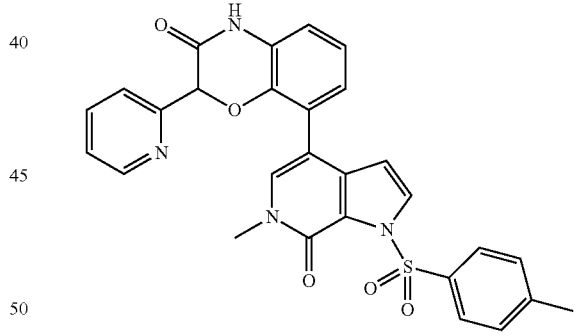

8-Bromo-2-pyridin-2-yl-2H-1,4-benzoxazin-3(4H)-one (15 mg, 0.049 mmol) and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (25 mg, 0.059 mmol) were dissolved in a mixture of 1,4-dioxane (2 mL) and potassium carbonate (10 mg, 0.07 mmol) in water (0.8 mL). The reaction was degassed with nitrogen and the catalyst [1,1'-bis(diphenylphosphino)ferrocene]dichloropalladium(II) complex with dichloromethane (1:1) (5 mg, 0.006 mmol) was added. The reaction was heated at 100° C. for 4 h, allowed to cool, and was partitioned between water and EtOAc. The combined organic layers were washed with brine, dried over magnesium sulfate, and concentrated. The product was purified on prep HPLC on a C-18 column eluting with a water:acetonitrile gradient buffered at pH 2 with TFA to afford 8-{6-methyl-1-[(4-methylphenyl)sulfonyl]-7-oxo-6,7-dihydro-1H-pyrrolo[2,3-c]pyridin-4-yl}-2-pyridin-2-yl-2H-1,4-benzoxazin-3(4H)-one 2,2,2-trifluoroacetate as a white solid (0.015 g, 58%). LCMS calculated for $C_{28}H_{23}N_4O_5S$ (M+H)$^+$: m/z=527.1; found 527.1.

Step 4. 8-(6-methyl-7-oxo-6,7-dihydro-1H-pyrrolo[2,3-c]pyridin-4-yl)-2-pyridin-2-yl-2H-1,4-benzoxazin-3(4H)-one 2,2,2 trifluoroacetate 8-{6-Methyl-1-[(4-methylphenyl)sulfonyl]-7-oxo-6,7-dihydro-1H-pyrrolo[2,3-c]pyridin-4-yl}-2-pyridin-2-yl-2H-1,4-benzoxazin-3(4H)-one 2,2,2 trifluoroacetate 0.015 g, 0.028 mmol) was dissolved in a mixture of ethanol (2 mL,) and 1.0 M sodium hydroxide in water (1 mL) and was stirred at 80° C. for 2 h. The reaction mixture was purified without work-up by prep HPLC on a C-18 column eluting with a water:acetonitrile gradient buffered at pH 2 with TFA to afford the title product as a white solid (0.004 g, 30%). LCMS calculated for $C_{21}H_{17}N_4O_3$ (M+H)$^+$: m/z=373.1; found=373.0.

Example 6. 2-cyclopropyl-8-(6-methyl-7-oxo-6,7-dihydro-1H-pyrrolo[2,3-c]pyridin-4-yl)-2H-1,4-benzoxazin-3(4H)-one

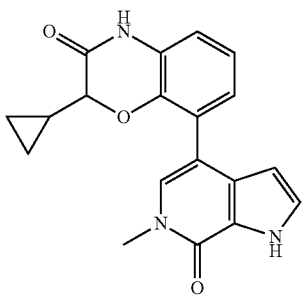 [SMILES: Cn1cc(-c2cccc3c2OC(C2CC2)C(=O)N3)c2cc[nH]c2c1=O]

Step 1. ethyl bromo(cyclopropyl)acetate

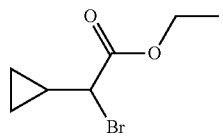

Thionyl chloride (0.46 mL, 6.3 mmol) was added dropwise to a solution of cyclopropylacetic acid (0.5 g, 5 mmol) (Oakwood cat#003710) in 1,2-dichloroethane (5.2 mL) at room temperature. The reaction was heated to reflux for 2 h then allowed to cool to room temperature, at which time N-bromosuccinimide (1.12 g, 6.27 mmol) and hydrogen bromide (2 L, 0.04 mmol) (48% aqueous solution) were added successively. The resulting mixture was heated to reflux for 2 days. The reaction mixture was then cooled to room temperature, ethanol (4 mL) was added, and the reaction was stirred at room temperature for an additional 2 h. The reaction mixture was then concentrated to afford the crude product. The crude product was dissolved in carbon tetrachloride and was passed through a short column of silica gel and concentrated to afford ethyl bromo(cyclopropyl)acetate (0.70 g, 70%) as an oil.

Step 2. 2-cyclopropyl-8-(6-methyl-7-oxo-6,7-dihydro-1H-pyrrolo[2,3-c]pyridin-4-yl)-2H-1,4-benzoxazin-3(4H)-one Using methods similar to Example 5, but using ethyl bromo(cyclopropyl)acetate, the title compound was prepared and purified by prep HPLC on a C-18 column eluting with a water: acetonitrile gradient buffered at pH 2 with TFA to afford 2-cyclopropyl-8-(6-methyl-7-oxo-6,7-dihydro-1H-pyrrolo[2,3-c]pyridin-4-yl)-2H-1,4-benzoxazin-3(4H)-one as a white amorphous solid (0.007 g, 40%). LCMS calculated for $C_{19}H_{18}N_3O_3$ (M+H)$^+$: m/z=336.1; found=336.1. $^1$H NMR (300 MHz, DMSO-d$_6$) δ 11.68 (s, 1H), 10.36 (s, 1H), 6.92 (d, J=3.5 Hz, 2H), 6.66 (d, J=4.6 Hz, 2H), 6.55 (q, J=4.7, 4.1 Hz, 1H), 5.83 (t, J=2.3 Hz, 1H), 3.72 (d, J=8.3 Hz, 1H), 3.20 (s, 3H), 0.82 (ddt, J=13.0, 8.2, 4.3 Hz, 1H), 0.21 (t, J=9.2 Hz, 1H), 0.14--0.05 (m, 3H).

Example 7. 8-(6-methyl-7-oxo-6,7-dihydro-1H-pyrrolo[2,3-c]pyridin-4-yl)-2-(tetrahydro-2H-pyran-4-yl)-2H-1,4-benzoxazin-3(4H)-one

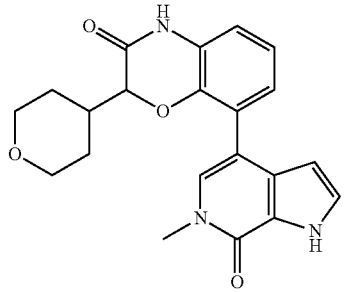 [SMILES: Cn1cc(-c2cccc3c2OC(C2CCOCC2)C(=O)N3)c2cc[nH]c2c1=O]

Step 1. methyl tetrahydro-2H-pyran-4-ylacetate

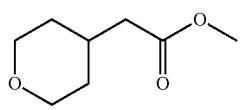

A mixture of tetrahydro-2H-pyran-4-ylacetic acid (500 mg, 3 mmol) (Combi Blocks cat#AM-1005) and sulfuric acid (20 μL, 0.4 mmol) in methanol (10 μL) was heated to reflux for 12 h. The mixture was then cooled and concentrated to remove the methanol. The resulting residue was dissolved in EtOAc, washed with saturated NaHCO$_3$, dried, and concentrated to afford methyl tetrahydro-2H-pyran-4-ylacetate (510 mg, 100%) as a crude product.

Step 2. methyl bromo(tetrahydro-2H-pyran-4-yl)acetate

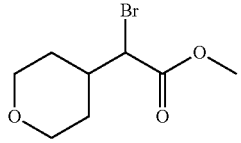

n-Butyllithium in hexanes 1.6 M (2 mL, 3 mmol) was added dropwise to a solution of N,N-diisopropylethylamine (0.6 mL, 3 mmol) in tetrahydrofuran (5 mL) at −78° C. The reaction mixture was stirred for 30 min and then added to a cold solution of methyl tetrahydro-2H-pyran-4-ylacetate (500 mg, 3 mmol) in tetrahydrofuran (5 mL). The mixture was stirred for 1 h, followed by addition of chlorotrimethylsilane (0.4 mL, 3 mmol). The resulting mixture was warmed to room temperature for 1 h, cooled to −78° C., and N-bromosuccinimide (0.6 g, 3 mmol) was added. The reaction was warmed to room temperature and stirred for an additional 2 h. The suspension was filtered through a silica gel pad, and the solids were washed with ethyl ether. The organic solution was concentrated to give crude methyl bromo(tetrahydro-2H-pyran-4-yl)acetate as an oil (0.30 g, 40%).

Step 3. 8-(6-methyl-7-oxo-6,7-dihydro-1H-pyrrolo[2,3-c]pyridin-4-yl)-2-(tetrahydro-2H-pyran-4-yl)-2H-1,4-benzoxazin-3(4H)-one Using methods similar to Example 5, but using methyl bromo(tetrahydro-2H-pyran-4-yl)acetate, the title compound was prepared as a white amorphous solid (0.008 g, 40%). LCMS calculated for $C_{21}H_{22}N_3O_4$ (M+H)$^+$: m/z=380.1; found=380.2. $^1$H NMR (500 MHz, DMSO-$d_6$) δ 12.00 (s, 1H), 10.73 (s, 1H), 7.25 (d, J=3.9 Hz, 2H), 7.03-6.97 (m, 2H), 6.88 (dd, J=6.6, 2.7 Hz, 1H), 6.21-6.11 (m, 1H), 4.45 (d, J=4.7 Hz, 1H), 3.73 (t, J=10.8 Hz, 2H), 3.54 (s, 3H), 3.24-3.12 (m, 2H), 2.18-2.08 (m, 1H), 1.46-1.26 (m, 4H).

Example 8. 2-ethyl-4-methyl-8-(6-methyl-7-oxo-6,7-dihydro-1H-pyrrolo[2,3-c]pyridin-4-yl)-2H-1,4-benzoxazin-3(4H)-one

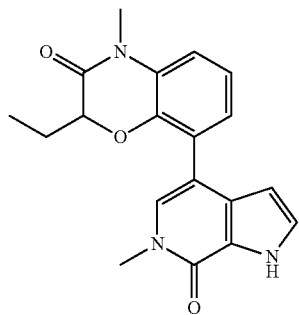 [SMILES: CCC1Oc2c(-c3cn(C)c(=O)c4[nH]ccc34)cccc2N(C)C1=O]

Step 1. 2-ethyl-4-methyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one

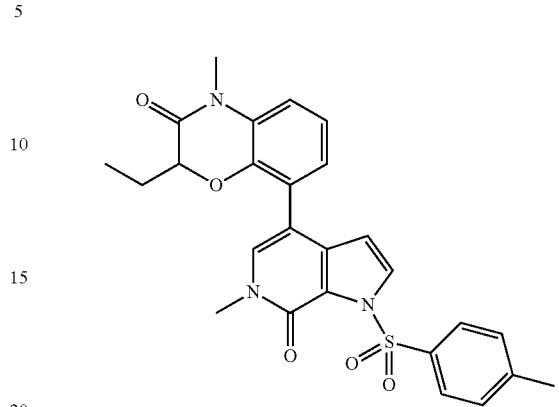

2-Ethyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one (20 mg, 0.04 mmol) of Example 4 was dissolved in N,N-dimethylformamide (1 mL), sodium hydride in mineral oil (2 mg, 0.08 mmol) was added, and the mixture was stirred for 10 min. Methyl iodide (4 μL, 0.06 mmol) was added and the mixture was stirred for an additional 30 min. The reaction mixture was then partitioned between ethyl acetate and water. The combined organic layers were washed with brine, dried over magnesium sulfate, and concentrated to afford crude 2-ethyl-4-methyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one as a glass (20 mg, 100%). LCMS calculated for $C_{26}H_{26}N_3O_5S$ (M+H)$^+$: m/z=492.1; found=491.9.

Step 2. 2-ethyl-4-methyl-8-(6-methyl-7-oxo-6,7-dihydro-1H-pyrrolo[2,3-c]pyridin-4-yl)-2H-1,4-benzoxazin-3(4H)-one Crude 2-ethyl-4-methyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one (20 mg, 0.04 mmol) was dissolved in a mixture of ethanol (2 mL) and 1.0 M sodium hydroxide in water (1 mL), and the reaction mixture was heated at 80° C. for 1 h. The reaction mixture was then purified without workup on prep LC-MS on a C-18 column eluting a water:acetonitrile gradient buffered at pH 2 with TFA to afford 2-ethyl-4-methyl-8-(6-methyl-7-oxo-6,7-dihydro-1H-pyrrolo[2,3-c]pyridin-4-yl)-2H-1,4-benzoxazin-3(4H)-one as white solid (6 mg, 40%). LCMS calculated for $C_{19}H_{20}N_3O_3$ (M+H)$^+$: m/z=338.1; found=338.1. $^1$H NMR (300 MHz, DMSO-$d_6$) δ 12.01 (s, 1H), 7.24 (d, J=5.3 Hz, 2H), 7.19-7.03 (m, 3H), 6.14 (s, 1H), 4.54 (dd, J=8.0, 4.2 Hz, 1H), 3.53 (s, 3H), 3.31 (s, 3H), 1.81 (dd, J=11.5, 7.2 Hz, 1H), 1.65 (dt, J=14.4, 7.6 Hz, 1H), 0.76 (t, J=7.3 Hz, 3H).

Example 9. 2-isopropyl-6-methoxy-8-(6-methyl-7-oxo-6,7-dihydro-1H-pyrrolo[2,3-c]pyridin-4-yl)-2H-1,4-benzoxazin-3(4H)-one

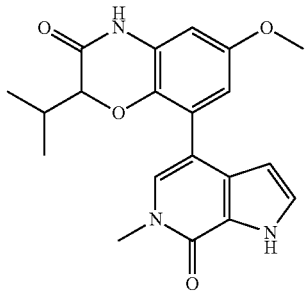 [SMILES: COc1cc2c(c(-c3cn(C)c(=O)c4[nH]ccc34)c1)OC(C(C)C)C(=O)N2]

Step 1. 8-bromo-2-isopropyl-6-methoxy-2H-1,4-benzoxazin-3(4H)-one

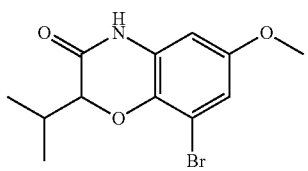 [SMILES: COc1cc(Br)c2c(c1)NC(=O)C(C(C)C)O2]

2-Amino-6-bromo-4-methoxyphenol (0.1 g, 0.4 mmol) (Aldrich cat#653705) and ethyl 2-bromo-3-methylbutanoate (0.11 mL, 0.69 mmol) (Alpha cat# B22525) were combined in N-methylpyrrolidinone (1.0 mL) with 1,8-diazabicyclo[5.4.0]undec-7-ene (0.14 mL, 0.92 mmol) in a sealed tube. The reaction mixture was heated to 140° C. in a microwave for 15 minutes. The reaction mixture was then cooled and partitioned between ethyl acetate and 1 N HCl. The combined organic layers were washed with brine, dried over magnesium sulfate, and concentrated to give a dark oil. The product was purified by FCC on silica gel eluting a hexane:ethyl acetate gradient to afford 8-bromo-2-isopropyl-6-methoxy-2H-1,4-benzoxazin-3(4H)-one as a semisolid (0.03 g, 30%). LCMS calculated for $C_{12}H_{15}BrNO_3$ (M+H)$^+$: m/z=300.1, 302.1; found=300.0, 302.0.

Step 2. 2-isopropyl-6-methoxy-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one

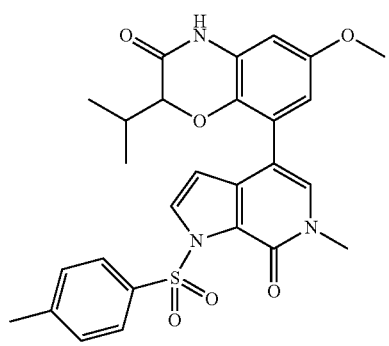

8-Bromo-2-isopropyl-6-methoxy-2H-1,4-benzoxazin-3(4H)-one (0.03 g, 0.1 mmol) was combined with 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (0.043 g, 0.10 mmol) in 1,4-dioxane (2.5 mL) and potassium carbonate (0.031 g, 0.22 mmol) in water (0.84 mL). The reaction was degassed with nitrogen and the catalyst [1,1'-bis(diphenylphosphino)ferrocene]dichloropalladium(II) complex with dichloromethane (1:1) (0.009 g, 0.01 mmol) was added. The reaction was heated in a sealed tube to 100° C. for 2 h. The mixture was then cooled to room temperature and was partitioned between ethyl acetate and water. The organic layer was washed with brine, dried over magnesium sulfate, and concentrated to afford 2-isopropyl-6-methoxy-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one as a dark oil (0.03 g, 60%). LCMS calculated for $C_{27}H_{28}N_3O_6S$ (M+H)$^+$: m/z=522.1; found=522.1.

Step 3. 2-isopropyl-6-methoxy-8-(6-methyl-7-oxo-6,7-dihydro-1H-pyrrolo[2,3-c]pyridin-4-yl)-2H-1,4-benzoxazin-3(4H)-one 2-Isopropyl-6-methoxy-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one (0.03 g, 0.06 mol) was dissolved in a mixture of ethanol (5.1 mL) and 1.0 M sodium hydroxide in water (1.7 mL) and heated to 80° C. in an oil bath for 1 h. The mixture was then cooled to room temperature and acidified with TFA. The crude product was purified by prep HPLC on a C-18 column eluting a water:acetonitrile gradient buffered at pH 2 with TFA to afford the title compound as an off white amorphous solid (0.02 g, 50%). LCMS calculated for $C_{20}H_{22}N_3O_4$ (M+H)$^+$: m/z=368.1; found=368.1. $^1$H NMR (300 MHz, DMSO-$d_6$) δ 12.01 (s, 1H), 10.61 (s, 1H), 7.35-7.20 (m, 2H), 6.57 (d, J=2.9 Hz, 1H), 6.45 (d, J=2.9 Hz, 1H), 6.20 (d, J=2.1 Hz, 1H), 4.30 (d, J=4.3 Hz, 1H), 3.70 (s, 3H), 3.53 (s, 3H), 2.28-2.09 (m, 1H), 0.80 (dd, J=11.7, 6.8 Hz, 6H).

Example 9A. 2-isopropyl-6-methoxy-8-(6-methyl-7-oxo-6,7-dihydro-1H-pyrrolo[2,3-c]pyridin-4-yl)-2H-1,4-benzoxazin-3(4H)-one (Enantiomer 1)

Example 9B. 2-isopropyl-6-methoxy-8-(6-methyl-7-oxo-6,7-dihydro-1H-pyrrolo[2,3-c]pyridin-4-yl)-2H-1,4-benzoxazin-3(4H)-one (Enantiomer 2)

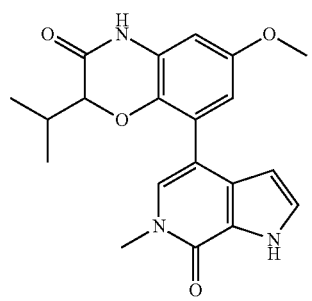 [SMILES: COc1cc2c(c(-c3cn(C)c(=O)c4[nH]ccc34)c1)OC(C(C)C)C(=O)N2]

The enantiomers of Example 9 were separated by prep chiral column chromatography using the following chiral separation conditions: Column: Chiralpak IA C-2 5 μm, 21, 2×250 mm; Mobile phase: 30% EtOH/Hexanes; gradient condition: isocratic at 14 mL/min; Loading: 1.0 mg in 900 µL; run time: 17 min; peak times: 11.0 and 14.4 min.

Example 9A, Peak 1 as a solid residue (11.0 min). LCMS calculated for C$_{20}$H$_{22}$N$_3$O$_4$ (M+H)$^+$: m/z=368.1; found=368.1. $^1$H NMR (300 MHz, DMSO-d$_6$) δ 12.01 (s, 1H), 10.61 (s, 1H), 7.35-7.20 (m, 2H), 6.57 (d, J=2.9 Hz, 1H), 6.45 (d, J=2.9 Hz, 1H), 6.20 (d, J=2.1 Hz, 1H), 4.30 (d, J=4.3 Hz, 1H), 3.70 (s, 3H), 3.53 (s, 3H), 2.28-2.09 (m, 1H), 0.80 (dd, J=11.7, 6.8 Hz, 6H).

Example 9B, Peak 2 as a solid residue (14.4). LCMS calculated for C$_{20}$H$_{22}$N$_3$O$_4$ (M+H)$^+$: m/z=368.1; found=368.1. $^1$H NMR (300 MHz, DMSO-d$_6$) δ 12.01 (s, 1H), 10.61 (s, 1H), 7.35-7.20 (m, 2H), 6.57 (d, J=2.9 Hz, 1H), 6.45 (d, J=2.9 Hz, 1H), 6.20 (d, J=2.1 Hz, 1H), 4.30 (d, J=4.3 Hz, 1H), 3.70 (s, 3H), 3.53 (s, 3H), 2.28-2.09 (m, 1H), 0.80 (dd, J=11.7, 6.8 Hz, 6H).

Example 10. 2-isopropyl-6-methoxy-4-methyl-8-(6-methyl-7-oxo-6,7-dihydro-1H-pyrrolo[2,3-c]pyridin-4-yl)-2H-1,4-benzoxazin-3(4H)-one

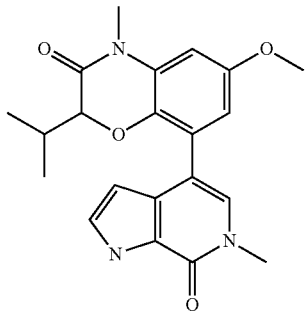 [SMILES: COc1cc(-c2cn(C)c(=O)c3[nH]ccc23)c2c(c1)N(C)C(=O)C(C(C)C)O2]

The compound of Example 10 was synthesized according to an experimental procedure analogous to that used for the synthesis of the compound of Example 8. LCMS found (M+H)$^+$: 382.1. $^1$H NMR (300 MHz, DMSO-d$_6$) δ 12.02 (s, 1H), 7.27 (d, J=4.5 Hz, 2H), 6.71 (d, J=2.7 Hz, 1H), 6.65 (d, J=2.7 Hz, 1H), 6.19 (bs, 1H), 4.32 (d, J=4.7 Hz, 1H), 3.77 (s, 3H), 3.53 (s, 3H), 3.31 (s, 3H), 2.22-2.10 (m, 1H), 0.77 (dd, J=15.1, 6.8 Hz, 6H).

Example 11. [2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]acetic acid

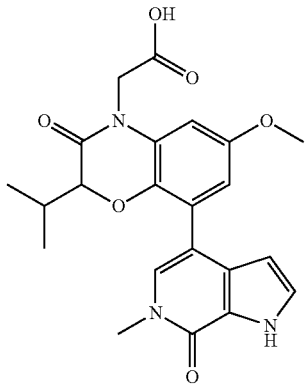 [SMILES: COc1cc(-c2cn(C)c(=O)c3[nH]ccc23)c2c(c1)N(CC(=O)O)C(=O)C(C(C)C)O2]

Step 1. tert-butyl (8-bromo-2-isopropyl-6-methoxy-3-oxo-2,3-dihydro-4H-1,4-benzoxazin-4-yl)acetate

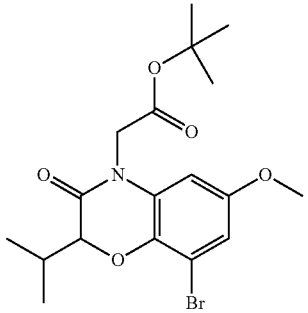 [SMILES: COc1cc(Br)c2c(c1)N(CC(=O)OC(C)(C)C)C(=O)C(C(C)C)O2]

8-Bromo-2-isopropyl-6-methoxy-2H-1,4-benzoxazin-3 (4H)-one (0.15 g, 0.50 mmol) of Example 10 was dissolved in N,N-dimethylformamide (2.0 mL, 26 mmol) at room temperature under nitrogen. Sodium hydride in mineral oil (0.024 g, 0.60 mmol) was added and the reaction was stirred for 15 minutes. Acetic acid, bromo-, 1,1-dimethylethyl ester (0.11 mL, 0.75 mmol) was then added and the resulting mixture was stirred at room temperature for 1 h. The reaction mixture was then quenched with water and extracted with ethyl acetate. The combined organic layers were washed with brine, dried over magnesium sulfate, and concentrated to afford the crude product as a semisolid. The crude product was purified by FCC on silica gel eluting a hexane: ethyl acetate gradient to afford tert-butyl (8-bromo-2-isopropyl-6-methoxy-3-oxo-2,3-dihydro-4H-1,4-benzoxazin-4-yl)acetate as a glass (0.15 g, 95%). LCMS calculated for C$_{18}$H$_{25}$BrNO$_5$ (M+H)$^+$: m/z=414.1, 416.1; found=358.1, 360.1 (M+H-tButyl).

Step 2. tert-butyl (2-isopropyl-6-methoxy-8-{6-methyl-1-[(4-methylphenyl)sulfonyl]-7-oxo-6,7-dihydro-1H-pyrrolo[2,3-c]pyridin-4-yl}-3-oxo-2,3-dihydro-4H-1,4-benzoxazin-4-yl)acetate

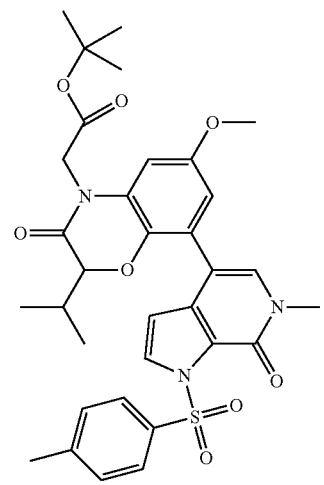 [SMILES: COc1cc(-c2cn(C)c(=O)c3c2ccn3S(=O)(=O)c2ccc(C)cc2)c2c(c1)N(CC(=O)OC(C)(C)C)C(=O)C(C(C)C)O2]

tert-Butyl (8-bromo-2-isopropyl-6-methoxy-3-oxo-2,3-dihydro-4H-1,4-benzoxazin-4-yl)acetate (0.030 g, 0.072 mmol) was combined with 6-methyl-1-[(4-methylphenyl)

sulfonyl]-4-(4,4,5,5-tetramethyl-1,3,2-dioxaborolan-2-yl)-1,6-dihydro-7H-pyrrolo[2,3-c]pyridin-7-one (0.031 g, 0.072 mmol) in 1,4-dioxane (1.8 mL) and potassium carbonate (0.022 g, 0.16 mmol) in water (0.61 mL). The mixture was degassed with nitrogen and the catalyst [1,1'-bis(diphenylphosphino)ferrocene]dichloropalladium(II) complex with dichloromethane (1:1) (0.006 g, 0.008 mmol) was added. The reaction mixture was heated in a sealed tube to 100° C. for 1 h. The reaction mixture was then cooled to room temperature and partitioned between ethyl acetate and water. The organic layer was washed with brine, dried over magnesium sulfate, and concentrated to afford tert-butyl (2-isopropyl-6-methoxy-8-{6-methyl-1-[(4-methylphenyl)sulfonyl]-7-oxo-6,7-dihydro-1H-pyrrolo[2,3-c]pyridin-4-yl}-3-oxo-2,3-dihydro-4H-1,4-benzoxazin-4-yl)acetate as a dark oil (0.04 g, 85%). LCMS calculated for $C_{33}H_{38}N_3O_8S$ $(M+H)^+$: m/z=636.2; found=636.2.

Step 3. [2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]acetic acid tert-Butyl (2-isopropyl-6-methoxy-8-{6-methyl-1-[(4-methylphenyl) sulfonyl]-7-oxo-6,7-dihydro-1H-pyrrolo[2,3-c]pyridin-4-yl}-3-oxo-2,3-dihydro-4H-1,4-benzoxazin-4-yl)acetate (0.04 g, 0.06 mmol) was dissolved in ethanol (3.7 mL) and 1.0 M sodium hydroxide in water (1.2 mL). The mixture was heated to 80° C. in an oil bath for 1 h, allowed to cool to room temperature, and acidified with TFA. The product was purified by prep HPLC on a C-18 column eluting a water:acetonitrile gradient buffered at pH 2 with TFA, to afford the title product as an off white amorphous solid (0.02 g, 65%). LCMS calculated for $C_{22}H_{24}N_3O_6$ $(M+H)^+$: m/z=426.1; found=426.2. $^1$H NMR (300 MHz, DMSO-d$_6$) δ 13.02 (s, 1H), 12.03 (s, 1H), 7.37-7.21 (m, 2H), 6.66 (d, J=2.7 Hz, 1H), 6.58 (d, J=2.7 Hz, 1H), 6.20 (bs, 1H), 4.64 (s, 2H), 4.34 (d, J=5.2 Hz, 1H), 3.74 (s, 3H), 3.54 (s, 3H), 2.13 (dd, J=12.3, 6.5 Hz, 1H), 0.81 (d, J=6.9 Hz, 3H), 0.74 (d, J 6.7 Hz, 3H).

Example 12. 2-[2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]-N-methylacetamide

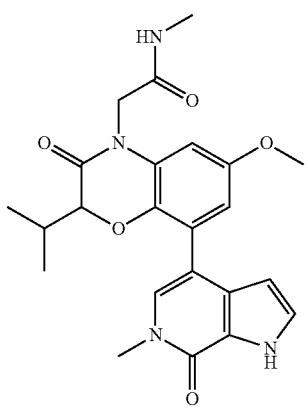 [SMILES: CNC(=O)CN1C(=O)C(C(C)C)Oc2c(-c3cn(C)c(=O)c4[nH]ccc34)cc(OC)cc21]

Step 1. 2-(8-bromo-2-isopropyl-6-methoxy-3-oxo-2,3-dihydro-4H-1,4-benzoxazin-4-yl)acetic acid

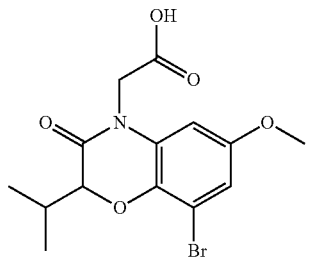 [SMILES: COc1cc(Br)c2c(c1)N(CC(=O)O)C(=O)C(C(C)C)O2]

tert-Butyl 2-(8-bromo-2-isopropyl-6-methoxy-3-oxo-2,3-dihydro-4H-1,4-benzoxazin-4-yl)acetate (0.190 g, 0.459 mmol) of Example 11 was dissolved in methylene chloride (3.0 mL) and trifluoroacetic acid (1.0 mL) at room temperature for 2 h. The reaction mixture was concentrated in vacuo to afford crude 2-(8-bromo-2-isopropyl-6-methoxy-3-oxo-2,3-dihydro-4H-1,4-benzoxazin-4-yl)acetic acid (0.163 g, 100%) as an oil. LCMS calculated for $C_{14}H_{17}BrNO_5$ $(M+H)^+$: m/z=358.1, 360.1; found=358.0, 360.0.

Step 2. 2-(8-bromo-2-isopropyl-6-methoxy-3-oxo-2,3-dihydro-4H-1,4-benzoxazin-4-yl)-N-methylacetamide

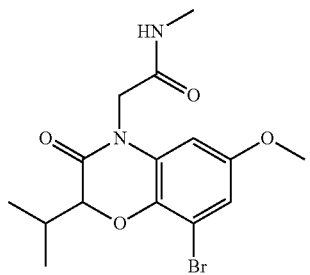 [SMILES: CNC(=O)CN1C(=O)C(C(C)C)Oc2c(Br)cc(OC)cc21]

2-(8-bromo-2-isopropyl-6-methoxy-3-oxo-2,3-dihydro-4H-1,4-benzoxazin-4-yl)acetic acid (0.05 g, 0.1 mmol) was dissolved in N,N-dimethylformamide (2.0 mL), and 2.0 M methylamine in methanol (0.35 mL, 0.70 mmol), N,N,N',N'-tetramethyl-O-(7-azabenzotriazol-1-yl)uronium hexafluorophosphate (0.064 g, 0.17 mmol) (Oakwood cat#023926) were added. The reaction mixture was stirred at room temperature for 2 h and then partitioned between ethyl acetate and water. The organic layer was washed with 1 N HCl, brine, dried over magnesium sulfate, and concentrated to afford crude 2-(8-bromo-2-isopropyl-6-methoxy-3-oxo-2,3-dihydro-4H-1,4-benzoxazin-4-yl)-N-methylacetamide as a an oil (0.05 g, 100%). LCMS calculated for $C_{15}H_{20}BrN_2O_4$ $(M+H)^+$: m/z=371.1, 373.1; found=371.0, 373.0.

Step 3. 2-(2-isopropyl-6-methoxy-8-{6-methyl-1-[(4-methylphenyl)sulfonyl]-7-oxo-6,7-dihydro-1H-pyrrolo[2,3-c]pyridin-4-yl}-3-oxo-2, 3-dihydro-4H-1,4-benzoxazin-4-yl)-N-methylacetamide

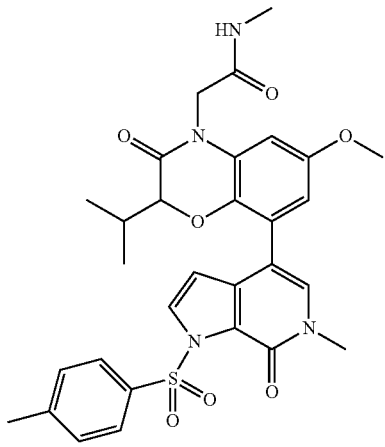

2-(8-Bromo-2-isopropyl-6-methoxy-3-oxo-2,3-dihydro-4H-1,4-benzoxazin-4-yl)-N-methylacetamide (0.027 g, 0.072 mmol) was combined with 6-methyl-1-[(4-methylphenyl)sulfonyl]-4-(4, 4,5,5-tetramethyl-1,3,2-dioxaborolan-2-yl)-1,6-dihydro-7H-pyrrolo[2,3-c]pyridin-7-one (0.031 g, 0.072 mmol) in 1,4-dioxane (1.8 mL) and potassium carbonate (0.022 g, 0.16 mmol) in water (0.61 mL). The mixture was degassed with nitrogen and the catalyst [1,1'-bis(diphenylphosphino)ferrocene]dichloropalladium (II) complex with dichloromethane (1:1) (0.006 g, 0.008 mmol) was added. The reaction mixture was then heated in a sealed tube to 100° C. for 1 h, cooled to room temperature, and partitioned between ethyl acetate and water. The organic layer was washed with brine, dried over magnesium sulfate, and concentrated to afford crude 2-(2-isopropyl-6-methoxy-8-{6-methyl-1-[(4-methylphenyl)sulfonyl]-7-oxo-6,7-dihydro-1H-pyrrolo[2,3-c]pyridin-4-yl}-3-oxo-2,3-dihydro-4H-1,4-benzoxazin-4-yl)-N-methylacetamide as a dark oil (0.035 g, 83%). LCMS calculated for $C_{30}H_{33}N_4O_7S$ $(M+H)^+$: m/z=593.1; found=593.2.

Step 4. 2-[2-isopropyl-6-methoxy-8-(6-methyl-7-oxo-6,7-dihydro-1H-pyrrolo[2,3-c]pyridin-4-yl)-3-oxo-2, 3-dihydro-4H-1,4-benzoxazin-4-yl]-N-methylacetamide 2-(2-Isopropyl-6-methoxy-8-{6-methyl-1-[(4-methylphenyl)sulfonyl]-7-oxo-6,7-dihydro-1H-pyrrolo[2,3-c]pyridin-4-yl}-3-oxo-2,3-dihydro-4H-1,4-benzoxazin-4-yl)-N-methylacetamide (0.035 g, 0.059 mmol) was dissolved in a mixture of ethanol (3.7 mL) and 1.0 M sodium hydroxide in water (1.2 mL) and heated to 80° C. in an oil bath for 1 h. The mixture was then cooled to room temperature and acidified with TFA. The product was purified by prep HPLC on a C-18 column eluting in a water:acetonitrile gradient buffered at pH 2 with TFA, to afford the title compound as an off white amorphous solid (0.015 g, 47%). LCMS calculated for $C_{23}H_{27}N_4O_5$ $(M+H)^+$: m/z=439.1; found=439.1. $^1$H NMR (300 MHz, DMSO-$d_6$) δ 12.03 (s, 1H), 8.09 (d, J=4.7 Hz, 1H), 7.27 (d, J=2.6 Hz, 2H), 6.65 (d, J=2.7 Hz, 1H), 6.44 (d, J=2.7 Hz, 1H), 6.23-6.14 (m, 1H), 4.58-4.38 (m, 2H), 4.35 (d, J=5.0 Hz, 1H), 3.72 (s, 3H), 3.54 (s, 3H), 2.63 (d, J=4.5 Hz, 3H), 2.16 (dd, J=11.9, 6.9 Hz, 1H), 0.81 (d, J=6.9 Hz, 3H), 0.75 (d, J=6.7 Hz, 3H).

Examples 13-16

The compounds of Examples 13-16 and the experimental procedures used to prepare them are set out in Table 2 below.

TABLE 2

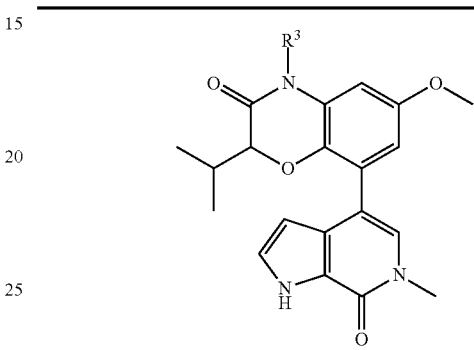

| Ex. No. | Name | $R^3$ | Synthetic Procedure |
|---|---|---|---|
| 13 | 2-[2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]acetamide | NH₂ group structure | Ex. No. 12 |
| 14 | 2-isopropyl-6-methoxy-8-(6-methyl-7-oxo-6,7-dihydro-1H-pyrrolo[2,3-c]pyridin-4-yl)-4-[2-(4-methylpiperazin-1-yl)-2-oxoethyl]-2H-1,4-benzoxazin-3(4H)-one | methylpiperazinyl-oxoethyl structure | Ex. No. 12 |
| 15 | 2-isopropyl-6-methoxy-8-(6-methyl-7-oxo-6,7-dihydro-1H-pyrrolo[2,3-c]pyridin-4-yl)-4-(pyridin-4-ylmethyl)-2H-1,4-benzoxazin-3(4H)-one | pyridin-4-ylmethyl structure | Ex. No. 8 |
| 16 | 2,4-diisopropyl-6-methoxy-8-(6-methyl-7-oxo-6,7-dhydro-1H-pyrrolo[2,3-c]pyridin-4-yl)-2H-1,4-benzoxazin-3(4H)-one | i-Prop | Ex. No. 8 |

Example 17. 2-isopropyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile

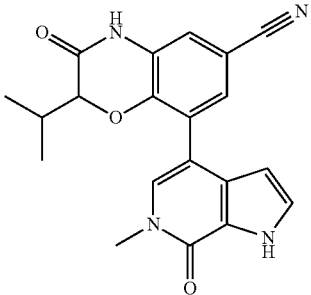 [SMILES: CC(C)C1Oc2c(cc(C#N)cc2-c2cn(C)c(=O)c3[nH]ccc23)NC1=O]

Step 1. 3-bromo-4-hydroxy-5-nitrobenzonitrile

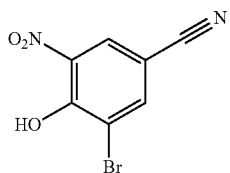 [SMILES: N#Cc1cc(N)c(O)c(Br)c1]

Bromine (500 mg, 3 mmol) was added to a mixture of 4-hydroxy-3-nitrobenzonitrile (500 mg, 3 mmol) (Aldrich cat#344575), ferric chloride (100 mg, 0.9 mmol) and acetic acid (20 mL) at room temperature. The reaction mixture was heated to 50° C. for 2 h, allowed to cool to room temperature, and water (100 mL) was added. A precipitate slowly formed, was collected, washed with water, and dried to obtain 3-bromo-4-hydroxy-5-nitrobenzonitrile (0.50 g, 70%) as a yellow solid. LCMS calculated for $C_7H_4BrN_2O_3$ (M+H)$^+$: m/z=242.9, 244.9; found=242.9, 244.9.

Step 2. 3-amino-5-bromo-4-hydroxybenzonitrile

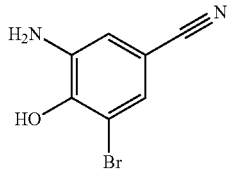

Iron filings (300 mg, 5 mmol) were added to a mixture of 3-bromo-4-hydroxy-5-nitrobenzonitrile (400 mg, 2 mmol) in acetic acid (20 mL). The mixture was then degassed with nitrogen and stirred overnight at room temperature. The reaction mixture was concentrated to remove the acetic acid, and the residue was partitioned between ethyl acetate and aqueous saturated sodium bicarbonate. The combined organic layers were washed with brine, dried over magnesium sulfate, filtered, and concentrated to afford crude 3-amino-5-bromo-4-hydroxybenzonitrile as a dark solid (250 mg, 70%). LCMS calculated for $C_7H_6BrN_2O$ (M+H)$^+$: m/z=212.9, 214.9; found=212.9, 214.9.

Step 3. 2-isopropyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile Using methods similar to conditions in Example 9, but using 3-amino-5-bromo-4-hydroxybenzonitrile, the title compound was prepared and purified by prep HPLC on a C-18 column eluting a water:acetonitrile gradient buffered at pH 2 with TFA to afford 2-isopropyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile as a white amorphous solid (0.007 g, 40%). LCMS calculated for $C_{20}H_{19}N_4O_3$ (M+H)$^+$: m/z=363.1; found=363.0. $^1$H NMR (300 MHz, DMSO-d$_6$) δ 12.06 (s, 1H), 11.01 (s, 1H), 7.46 (d, J=2.0 Hz, 1H), 7.34 (s, 1H), 7.27 (t, J=2.7 Hz, 1H), 7.18 (d, J 2.0 Hz, 1H), 6.24-6.13 (m, 1H), 4.62 (d, J=3.8 Hz, 1H), 3.53 (s, 3H), 2.29-2.16 (m, 1H), 0.78 (dd, J=6.8, 3.9 Hz, 6H).

Example 18. 2-isopropyl-4-methyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile

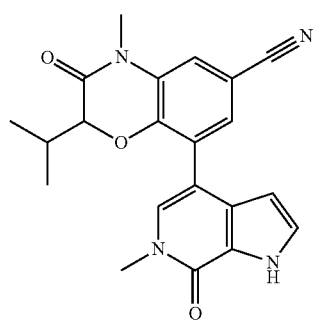 [SMILES: CC(C)C1Oc2c(-c3cn(C)c(=O)c4[nH]ccc34)cc(C#N)cc2N(C)C1=O]

Step 1. 8-bromo-2-isopropyl-4-methyl-3-oxo-3,4-dihydro-2H-1,4-benzoxazine-6-carbonitrile

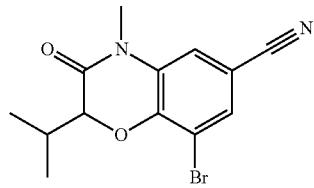 [SMILES: CC(C)C1Oc2c(Br)cc(C#N)cc2N(C)C1=O]

Sodium hydride in mineral oil (2 mg, 0.07 mmol) was added to a mixture of 8-bromo-2-isopropyl-3-oxo-3,4-dihydro-2H-1,4-benzoxazine-6-carbonitrile (20 mg, 0.07 mmol) of Example 17, in N,N-dimethylformamide (2 mL). The reaction mixture was stirred for 5 minutes, methyl iodide (5.1 µL, 0.081 mmol) was added, and the reaction mixture was stirred for an additional 1 h. The reaction was then partitioned between ethyl acetate and water. The combined organic layers were washed with brine, dried over MgSO$_4$, filtered, and concentrated to afford crude 8-bromo-2-isopropyl-4-methyl-3-oxo-3,4-dihydro-2H-1,4-benzoxazine-6-carbonitrile as a glass (0.020 g, 100%). LCMS calculated for $C_{13}H_{14}BrN_2O_2$(M+H)$^+$: m/z=309.1, 311.1; found=308.9, 310.7.

Step 2. 2-isopropyl-4-methyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazine-6-carbonitrile

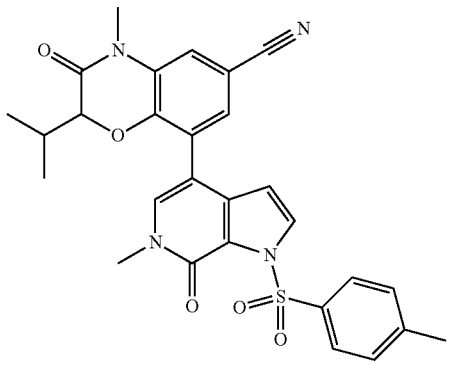 [SMILES: Cc1ccc(S(=O)(=O)n2ccc3c(-c4cc(C#N)cc5c4OC(C(C)C)C(=O)N5C)cn(C)c(=O)c32)cc1]

8-Bromo-2-isopropyl-4-methyl-3-oxo-3,4-dihydro-2H-1,4-benzoxazine-6-carbonitrile (16 mg, 0.051 mmol) and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (26 mg, 0.061 mmol) were dissolved in 1,4-dioxane (2 mL) with potassium carbonate (10 mg, 0.08 mmol) in water (0.9 mL) and the mixture was degassed with nitrogen. The catalyst [1,1'-bis(diphenylphosphino)ferrocene]dichloropalladium(II) complex with dichloromethane (1:1) (5 mg, 0.006 mmol) was added and the mixture was heated at 100° C. for 4 h. The reaction mixture was then cooled and partitioned between water and ethyl acetate. The combined organic layers were dried with MgSO$_4$ and concentrated to afford crude 2-isopropyl-4-methyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazine-6-carbonitrile as a glass (0.027 g, 100%). LCMS calculated for $C_{28}H_{27}N_4O_5S$ (M+H)$^+$: m/z=531.1; found=531.2.

Step 3. 2-isopropyl-4-methyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile 2-Isopropyl-4-methyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazine-6-carbonitrile (0.027 g, 0.051 mmol) was dissolved in a mixture of ethanol (2 mL) and 1.0 M sodium hydroxide in water (1 mL). The mixture was then heated at 80° C. for 1 h. The reaction mixture was purified without workup by prep HPLC on a C-18 column eluting water:acetonitrile gradient buffered at pH 2 with TFA to afford the title compound as a white amorphous solid (0.005 g, 26%). LCMS calculated for $C_{21}H_{21}N_4O_3$ (M+H)$^+$: m/z=377.1; found=377.1. $^1$H NMR (300 MHz, DMSO-d$_6$) δ 12.06 (s, 1H), 7.65 (d, J=1.9 Hz, 1H), 7.56 (d, 1H), 7.34 (s, 1H), 7.30-7.25 (m, 1H), 6.21-6.14 (m, 1H), 4.62 (d, J=4.2 Hz, 1H), 3.54 (s, 3H), 3.34 (s, 3H), 2.27-2.18 (m, 1H), 0.75 (d, J=6.8 Hz, 6H).

Example 19. 2-isopropyl-4-methyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide

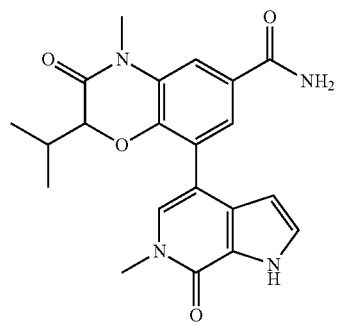 [SMILES: CC(C)C1Oc2c(-c3cn(C)c(=O)c4[nH]ccc34)cc(C(N)=O)cc2N(C)C1=O]

2-Isopropyl-4-methyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazine-6-carbonitrile of Example 18 was dissolved in a mixture of ethanol (2 mL) and 1.0 M sodium hydroxide in water (1 mL). The mixture was then heated at 80° C. for 4 h. The reaction mixture was purified without workup by prep HPLC on a C-18 column eluting a water:acetonitrile gradient buffered at pH 2 with TFA to afford the title compound as a white amorphous solid (0.007 g, 20%). LCMS calculated for $C_{21}H_{23}N_4O_4$ (M+H)$^+$: m/z=395.1; found=395.2. $^1$H NMR (300 MHz, DMSO-d$_6$) δ 12.04 (s, 1H), 8.00 (s, 1H), 7.68 (d, J=1.3 Hz, 1H), 7.61 (d, J=1.5 Hz, 1H), 7.35 (s, 1H), 7.30 (s, 1H), 7.27 (t, J=2.5 Hz, 1H), 6.15 (t, J=2.1 Hz, 1H), 4.51 (d, J=4.3 Hz, 1H), 3.55 (s, 3H), 3.36 (s, 3H), 2.21 (dd, J=11.4, 6.7 Hz, 1H), 0.77 (dd, J=6.6 Hz, 6H).

Example 20. 2-isopropyl-N-methyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide

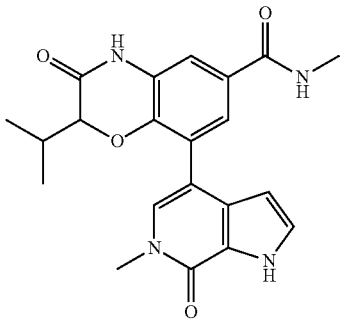 [SMILES: CNC(=O)c1cc2c(c(-c3cn(C)c(=O)c4[nH]ccc34)c1)OC(C(C)C)C(=O)N2]

Step 1. 8-bromo-2-isopropyl-3-oxo-3,4-dihydro-2H-1,4-benzoxazine-6-carboxylic acid

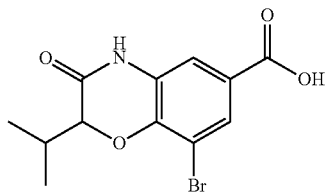 [SMILES: CC(C)C1Oc2c(Br)cc(C(=O)O)cc2NC1=O]

A solution of 8-bromo-2-isopropyl-3-oxo-3,4-dihydro-2H-1,4-benzoxazine-6-carbonitrile (from Example 18, 30 mg, 0.1 mmol) in concentrated hydrochloroic acid (1 mL, 30 mmol) was heated at 100° C. for 10 h. The reaction mixture was cooled and concentrated in vacuo, then partitioned between water and ethyl acetate. The combined organic layers were washed with brine, dried over MgSO$_4$, filtered, and concentrated to afford crude 8-bromo-2-isopropyl-3-oxo-3,4-dihydro-2H-1,4-benzoxazine-6-carboxylic acid as a solid residue (30 mg, 100%). LCMS calculated for $C_{12}H_{13}BrNO_4$ (M+H)$^+$: m/z=314.0, 316.0; found=313.9, 315.9.

Step 2. 8-bromo-2-isopropyl-N-methyl-3-oxo-3,4-dihydro-2H-1,4-benzoxazine-6-carboxamide

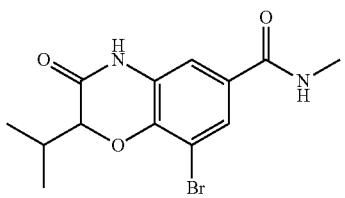 [SMILES: CNC(=O)c1cc(Br)c2c(c1)NC(=O)C(C(C)C)O2]

N,N,N',N'-Tetramethyl-O-(7-azabenzotriazol-1-yl)uronium hexafluorophosphate (54 mg, 0.14 mmol) and N,N-diisopropylethylamine (30 µL, 0.2 mmol) were added to a solution of 8-bromo-2-isopropyl-3-oxo-3,4-dihydro-2H-1,4-benzoxazine-6-carboxylic acid (30 mg, 0.1 mmol) in DMF (2 mL). Methylamine in ethanol (3 M, 48 µL, 0.14 mmol) was added and the reaction was stirred at room temperature for 1 h. The reaction mixture was then partitioned between 1 N HCl and ethyl acetate. The combined organic layers were washed with brine, dried over MgSO$_4$, filtered, and concentrated to afford crude 8-bromo-2-isopropyl-N-methyl-3-oxo-3,4-dihydro-2H-1,4-benzoxazine-6-carboxamide as a glass (30 mg, 90%). LCMS calculated for $C_{13}H_{16}BrN_2O_3$ (M+H)$^+$: m/z=327.1, 329.1; found=327.0, 329.0.

Step 3. 2-isopropyl-N-methyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide Using methods similar to conditions in Example 9, but using 8-bromo-2-isopropyl-N-methyl-3-oxo-3,4-dihydro-2H-1,4-benzoxazine-6-carboxamide from Step 2, the title compound was prepared and purified by prep HPLC on a C-18 column eluting a water:acetonitrile gradient buffered at pH 2 with TFA to afford 2-isopropyl-N-methyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide as a white amorphous solid (5 mg, 30%). LCMS calculated for $C_{21}H_{23}N_4O_4$ (M+H)$^+$: m/z=395.1; found=395.1. $^1$H NMR (300 MHz, DMSO-d$_6$) δ 12.03 (s, 1H), 10.84 (s, 1H), 8.38-8.28 (m, 1H), 7.50 (d, J=2.1 Hz, 1H), 7.37 (d, J=1.9 Hz, 1H), 7.28 (s, 1H), 7.27-7.23 (m, 1H), 6.18 (s, 1H), 4.49 (d, J=4.1 Hz, 1H), 3.55 (s, 3H), 2.73 (d, J=4.4 Hz, 3H), 2.27-2.14 (m, 1H), 0.79 (dd, J 6.9, 2.0 Hz, 6H).

Example 21. 2-isopropyl-8-(6-methyl-7-oxo-6,7-dihydro-1H-pyrrolo[2,3-c]pyridin-4-yl)-6-nitro-2H-1,4-benzoxazin-3(4H)-one

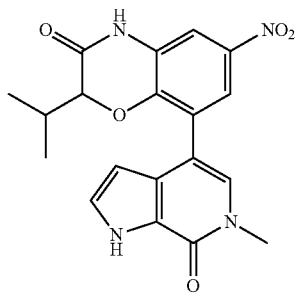 [SMILES: CC(C)C1Oc2c(cc([N+](=O)[O-])cc2-c2cn(C)c(=O)c3[nH]ccc23)NC1=O]

The compound of Example 21 was synthesized according to an experimental procedure analogous to that used for the synthesis of the compound of Example 9. LCMS found (M+H)$^+$: 383.1. $^1$H NMR (300 MHz, DMSO-d$_6$) δ 12.11 (s, 1H), 11.11 (s, 1H), 7.90 (d, J=2.8 Hz, 1H), 7.73 (d, J=2.8 Hz, 1H), 7.36-7.22 (m, 2H), 6.23 (s, 1H), 4.70 (d, J=3.6 Hz, 1H), 3.55 (s, 3H), 2.30-2.19 (m, 1H), 0.80 (d, J=6.8 Hz, 6H).

Example 22. 4-(2-isopropyl-6-methoxy-4-methyl-3,4-dihydro-2H-1,4-benzoxazin-8-yl)-6-methyl-1,6-dihydro-7H-pyrrolo[2,3-c]pyridin-7-one

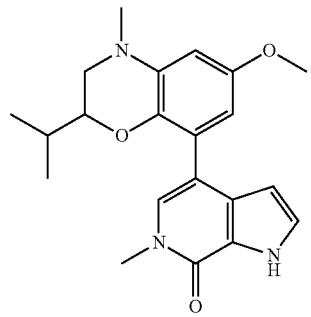 [SMILES: COc1cc(-c2cn(C)c(=O)c3[nH]ccc23)c2c(c1)N(C)CC(C(C)C)O2]

Step 1. 8-bromo-2-isopropyl-6-methoxy-3,4-dihydro-2H-1,4-benzoxazine

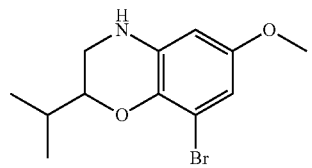 [SMILES: COc1cc(Br)c2c(c1)NCC(C(C)C)O2]

2.0 M Borane-dimethyl sulfide complex (Aldrich cat#194824) in toluene (400 μL, 0.7 mmol) was added dropwise to a mixture of 8-bromo-2-isopropyl-6-methoxy-2H-1,4-benzoxazin-3(4H)-one (100 mg, 0.4 mmol) of Example 9 at room temperature and the mixture was then heated at 60° C. overnight. The reaction mixture was cooled to room temperature, diluted with MeOH, and was heated at 60° C. for an additional 30 min. The mixture was then cooled to room temperature and concentrated to yield crude product. The crude product was purified by FCC on silica gel eluting a hexane: ethyl acetate gradient to afford 8-bromo-2-isopropyl-6-methoxy-3,4-dihydro-2H-1,4-benzoxazine as a clear oil (70 mg, 70%). LCMS calculated for $C_{12}H_{17}BrNO_2$ (M+H)$^+$: m/z=286.1, 288.1; found=286.0, 288.0.

Step 2. 4-(2-isopropyl-6-methoxy-4-methyl-3,4-dihydro-2H-1,4-benzoxazin-8-yl)-6-methyl-1,6-dihydro-7H-pyrrolo[2,3-c]pyridin-7-one Using methods similar to conditions in Example 8, but using 8-bromo-2-isopropyl-6-methoxy-3,4-dihydro-2H-1,4-benzoxazine from Step 1, the title compound was prepared and purified by prep HPLC on a C-18 column eluting a water:acetonitrile gradient buffered at pH 2 with TFA to afford 4-(2-isopropyl-6-methoxy-4-methyl-3,4-dihydro-2H-1,4-benzoxazin-8-yl)-6-methyl-1,6-dihydro-7H-pyrrolo[2,3-c]pyridin-7-one as a white amorphous solid (5 mg, 30%). LCMS calculated for $C_{21}H_{26}N_3O_3$ (M+H)$^+$: m/z=368.1; found=368.1. $^1$H NMR (300 MHz, DMSO-$d_6$) δ 11.90 (s, 1H), 7.21 (t, J=2.7 Hz, 1H), 7.16 (s, 1H), 6.24 (d, J=2.8 Hz, 1H), 6.18 (d, J=2.8 Hz, 1H), 6.12 (d, J=2.1 Hz, 1H), 3.75-3.67 (m, 1H), 3.67 (s, 3H), 3.51 (s, 3H), 3.30 (d, J=9.5 Hz, 1H), 3.01-2.91 (m, 1H), 2.85 (s, 3H), 1.68-1.57 (m, 1H), 0.82 (d, J=6.8 Hz, 3H), 0.75 (d, J=6.7 Hz, 3H).

Examples 23-24

The compounds of Examples 23-24 and the experimental procedures used to prepare them are set out in Table 3 below.

TABLE 3

| Ex. No. | Name | R$^1$ | Synthetic Procedure |
|---|---|---|---|
| 23 | 2-cyclopropyl-6-methoxy-8-(6-methyl-7-oxo-6,7-dihydro-1H-pyrrolo[2,3-c]pyridin-4-yl)-2H-1,4-benzoxazin-3(4H)-one | cyclopropyl | Ex. No. 6 |
| 24 | 6-methoxy-8-(6-methyl-7-oxo-6,7-dihydro-1H-pyrrolo[2,3-c]pyridin-4-yl)-2-phenyl-2H-1,4-benzoxazin-3(4H)-one | phenyl | Ex. No. 6 |

Example 24A. 6-methoxy-8-(6-methyl-7-oxo-6,7-dihydro-1H-pyrrolo[2,3-c]pyridin-4-yl)-2-phenyl-2H-1,4-benzoxazin-3(4H)-one (Enantiomer 1)

Example 24B. 6-methoxy-8-(6-methyl-7-oxo-6,7-dihydro-1H-pyrrolo[2,3-c]pyridin-4-yl)-2-phenyl-2H-1,4-benzoxazin-3(4H)-one (Enantiomer 2)

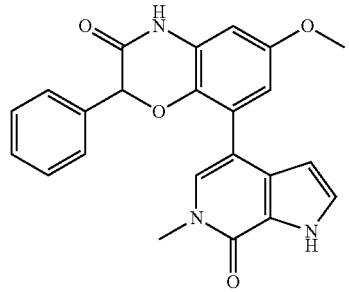 [SMILES: COc1cc2c(c(-c3cn(C)c(=O)c4[nH]ccc34)c1)OC(c1ccccc1)C(=O)N2]

The enantiomers of Example 24 were separated by prep chiral HPLC using the following conditions: Column: Phenomenex Lux Cellulose C-4, 5 μm, 21.2×25 mm; Mobile phase: 30% Ethanol in Hexanes; Gradient: 18 mL/min; Loading: 2 mg in 1800 μL; Run time: 28 min; Peak retention times: 20.9 and 24.0 minutes.

Example 24A, Peak 1 (20.9 min) as a solid residue. LCMS calculated for $C_{23}H_{20}N_3O_4$ (M+H)$^+$: m/z=402.1; found: 402.1. $^1$H NMR (300 MHz, DMSO-$d_6$) δ 11.93 (s, 1H), 10.90 (s, 1H), 7.28-7.17 (m, 4H), 7.13 (t, J=2.7 Hz, 1H), 7.02 (s, 1H), 6.49 (d, J=2.9 Hz, 1H), 6.46 (d, J=2.9 Hz, 1H), 5.99 (s, 1H), 5.61 (s, 1H), 3.65 (s, 3H), 3.42 (s, 3H).

Example 24B, Peak 2 (24.0 min) as a solid residue. LCMS calculated for $C_{23}H_{20}N_3O_4$ (M+H)$^+$: m/z=402.1; found: 402.1. $^1$H NMR (300 MHz, DMSO-$d_6$) δ 11.93 (s, 1H), 10.90 (s, 1H), 7.28-7.17 (m, 4H), 7.13 (t, J=2.7 Hz, 1H), 7.02 (s, 1H), 6.49 (d, J=2.9 Hz, 1H), 6.46 (d, J=2.9 Hz, 1H), 5.99 (s, 1H), 5.61 (s, 1H), 3.65 (s, 3H), 3.42 (s, 3H).

Example 25. 2-(2-chloro-4-fluorophenyl)-6-methoxy-8-(6-methyl-7-oxo-6,7-dihydro-1H-pyrrolo[2,3-c]pyridin-4-yl)-2H-1,4-benzoxazin-3(4H)-one

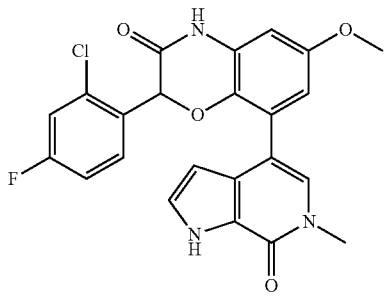 [SMILES: COc1cc2c(c(-c3cn(C)c(=O)c4[nH]ccc34)c1)OC(c1ccc(F)cc1Cl)C(=O)N2]

Step 1. methyl bromo(2-chloro-4-fluorophenyl)acetate

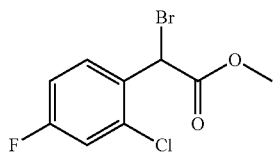

A solution of methyl (2-chloro-4-fluorophenyl)acetate (100 mg, 0.5 mmol) (Acros Organics cat#30478) and N-bromosuccinimide (90 mg, 0.5 mmol) in carbon tetrachloride (0.7 mL) was heated to 100° C. for 1 h. The reaction mixture was cooled to room temperature, filtered, and partitioned between ethyl acetate and water. The combined organic layers were washed with brine, dried over MgSO$_4$, filtered, and concentrated to afford crude methyl bromo(2-chloro-4-fluorophenyl)acetate as light yellow semi solid (120 mg, 90%).

Step 2. 2-(2-chloro-4-fluorophenyl)-6-methoxy-8-(6-methyl-7-oxo-6,7-dihydro-1H-pyrrolo[2,3-c]pyridin-4-yl)-2H-1,4-benzoxazin-3(4H)-one Using methods similar to conditions in Example 9, but using methyl bromo(2-chloro-4-fluorophenyl)acetate from Step 1, the title compound was prepared and purified by prep HPLC on a C-18 column eluting a water:acetonitrile gradient buffered at pH 2 with TFA to afford 2-(2-chloro-4-fluorophenyl)-6-methoxy-8-(6-methyl-7-oxo-6,7-dihydro-1H-pyrrolo[2,3-c]pyridin-4-yl)-2H-1,4-benzoxazin-3(4H)-one as a white amorphous solid (4 mg, 20%). LCMS calculated for $C_{23}H_{18}ClFN_3O_4(M+H)^+$: m/z=454.1; found=454.1. $^1$H NMR (300 MHz, DMSO-d$_6$) δ 11.94 (s, 1H), 11.00 (s, 1H), 7.52-7.40 (m, 2H), 7.36-7.13 (m, 2H), 7.11 (s, 1H), 6.55 (s, 1H), 6.13 (s, 1H), 5.87 (s, 1H), 3.74 (s, 3H), 3.46 (s, 3H).

Example 26. 2-isopropyl-6-methoxy-8-(6-methyl-7-oxo-6,7-dihydro-1H-pyrazolo[3,4-c]pyridin-4-yl)-2H-1,4-benzoxazin-3(4H)-one

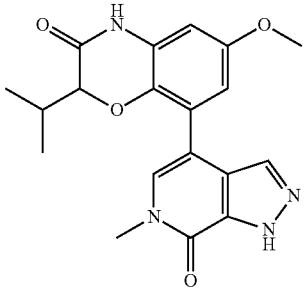 [SMILES: COc1cc2c(c(-c3cn(C)c(=O)c4[nH]ncc34)c1)OC(C(C)C)C(=O)N2]

Step 1. 2-isopropyl-6-methoxy-8-(6-methyl-7-oxo-1-{[2-(trimethylsilyl)ethoxy]methyl}-6,7-dihydro-1H-pyrazolo[3,4-c]pyridin-4-yl)-2H-1,4-benzoxazin-3(4H)-one

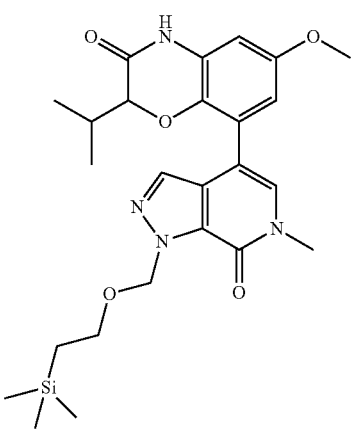

Using methods similar to conditions in Example 9, but using 6-methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one (0.081 g, 0.20 mmol) (WO2013097601), the title compound was prepared as an oil. LCMS calculated for $C_{25}H_{35}N_4O_5Si$ $(M+H)^+$: m/z=499.2; found=499.2.

Step 2. 2-isopropyl-6-methoxy-8-(6-methyl-7-oxo-6,7-dihydro-1H-pyrazolo[3,4-c]pyridin-4-yl)-2H-1,4-benzoxazin-3(4H)-one 2-Isopropyl-6-methoxy-8-(6-methyl-7-oxo-1-{[2-(trimethylsilyl)ethoxy]methyl}-6,7-dihydro-1H-pyrazolo[3,4-c]pyridin-4-yl)-2H-1,4-benzoxazin-3(4H)-one was dissolved in a mixture of methylene chloride and TFA (2:1) and was stirred at room temperature for 3 h. The reaction mixture was concentrated in vacuo to give an oily residue. This residue was dissolved in ethanol (3 mL) and ammonium hydroxide (1 mL) and the mixture was stirred overnight at room temperature. The mixture was then concentrated in vacuo to give a glassy residue. The product was purified by prep HPLC on a C-18 column eluting a water:acetonitrile gradient buffered at pH 2 with TFA, to afford the title compound as an off white amorphous solid (25 mg, 42%). LCMS calculated for $C_{19}H_{21}N_4O_4$ (M+H)$^+$: m/z=369.1; found=369.1. $^1$H NMR (300 MHz, DMSO-d$_6$) δ 10.64 (s, 1H), 7.80 (s, 1H), 7.36 (s, 1H), 6.58 (d, J=2.4 Hz, 1H), 6.48 (d, J=2.6 Hz, 1H), 4.39 (d, J=3.8 Hz, 1H), 3.72 (s, 3H), 3.56 (s, 3H), 2.28-2.11 (m, 1H), 0.76 (dd, J=6.6, 3.4 Hz, 6H).

Example 27. 6-methoxy-2,2-dimethyl-8-(6-methyl-7-oxo-6,7-dihydro-1H-pyrrolo[2,3-c]pyridin-4-yl)-2H-1,4-benzoxazin-3(4H)-one

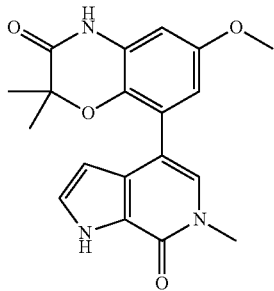

The compound of Example 27 was synthesized according to an experimental procedure analogous to that used for the synthesis of the compound of Example 9 to give a white amorphous solid (15 mg, 25%). LCMS found (M+H)$^+$: 354.1. $^1$H NMR (300 MHz, DMSO-d$_6$) δ 12.03 (s, 1H), 10.59 (s, 1H), 7.26 (t, J=2.7 Hz, 1H), 7.19 (s, 1H), 6.56 (d, J=2.9 Hz, 1H), 6.47 (d, J=2.9 Hz, 1H), 6.22-6.12 (m, 1H), 3.70 (s, 3H), 3.54 (s, 3H), 1.30 (s, 6H).

Example 28. 2-isopropyl-8-(6-methyl-7-oxo-6,7-dihydro-1H-pyrrolo[2,3-c]pyridin-4-yl)-6-(1-methyl-1H-pyrazol-4-yl)-2H-1,4-benzoxazin-3(4H)-one

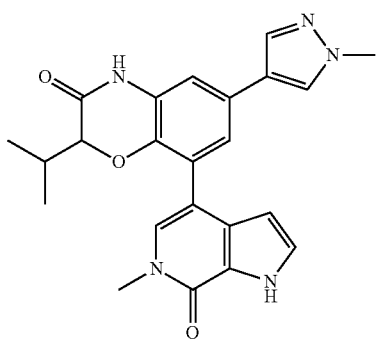 [SMILES: CC(C)C1Oc2c(cc(-c3cnn(C)c3)cc2-c2cn(C)c(=O)c3[nH]ccc23)NC1=O]

Step 1. 4-(1-methyl-1H-pyrazol-4-yl)-2-nitrophenol

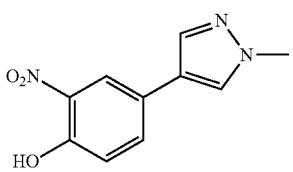 [SMILES: Cn1cc(-c2ccc(O)c([N+](=O)[O-])c2)cn1]

4-Bromo-2-nitrophenol (1.0 g, 4.6 mmol) (Aldrich cat#309877) was combined with 1-methyl-4-(4,4,5,5-tetramethyl-1,3,2-dioxaborolan-2-yl)-1H-pyrazole (1.0 g, 5.0 mmol) (Acros Organics cat#38296) in 1,4-dioxane (20 mL) and cesium fluoride (1.5 g, 10 mmol) in water (10 mL). The mixture was degassed with nitrogen, the catalyst 4-(di-tert-butylphosphino)-N,N-dimethylaniline-dichloropalladium (2:1) (0.1 g, 0.2 mmol) was added, and the mixture was heated in a sealed tube to 100° C. for 1 h. The mixture was then cooled to room temperature and partitioned between ethyl acetate and water. The organic layer was washed with brine, dried over magnesium sulfate, and concentrated to yield a dark oil. The product was purified by FCC on silica gel eluting a hexane: ethyl acetate gradient to afford 4-(1-methyl-1H-pyrazol-4-yl)-2-nitrophenol as a yellow solid (0.20 g, 20%). LCMS calculated for $C_{10}H_{10}N_3O_3$ (M+H)$^+$: m/z=220.1; found=220.1.

Step 2. 2-bromo-4-(1-methyl-1H-pyrazol-4-yl)-6-nitrophenol

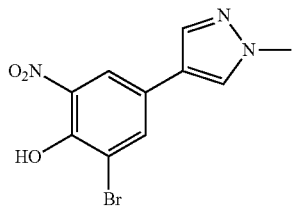 [SMILES: Cn1cc(-c2cc(Br)c(O)c([N+](=O)[O-])c2)cn1]

4-(1-Methyl-1H-pyrazol-4-yl)-2-nitrophenol (0.10 g, 0.46 mmol) was dissolved in acetic acid (3.9 mL) and ferric chloride (0.01 g, 0.09 mmol) in water (0.56 mL) was added. The reaction mixture was stirred at room temperature followed by addition of bromine (0.073 g, 0.46 mmol) in acetic acid (2 mL). The resulting mixture was stirred for an additional 2 h at room temperature then diluted with water to yield a slurry. This slurry was filtered and the solids were washed with water and dried. The product was purified by FCC on silica gel eluting a hexane: ethyl acetate gradient to afford 2-bromo-4-(1-methyl-1H-pyrazol-4-yl)-6-nitrophenol as a semisolid (0.12 g, 85%). LCMS calculated for $C_{10}H_9BrN_3O_3$(M+H)$^+$: m/z=298.1, 300.1; found=297.9, 299.9.

Step 3. 2-isopropyl-8-(6-methyl-7-oxo-6,7-dihydro-1H-pyrrolo[2,3-c]pyridin-4-yl)-6-(1-methyl-1H-pyrazol-4-yl)-2H-1,4-benzoxazin-3(4H)-one Using methods similar to conditions in Example 9, but using 2-bromo-4-(1-methyl-1H-pyrazol-4-yl)-6-nitrophenol from Step 2, the crude product was prepared. The product was purified by prep HPLC on a C-18 column eluting a water:acetonitrile gradient buffered at pH 2 with TFA, to afford the title compound as an off white amorphous solid (18 mg, 30%). LCMS calculated for $C_{23}H_{24}N_5O_3$ (M+H)$^+$: m/z=418.2; found=418.2. $^1$H NMR (300 MHz, DMSO-d$_6$) δ 12.00 (s, 1H), 10.71 (s, 1H), 8.00 (s, 1H), 7.68 (s, 1H), 7.29 (s, 1H), 7.28-7.23 (m, 1H), 7.17 (d, J=1.9 Hz, 1H), 6.97 (d, J=1.9 Hz, 1H), 6.19 (s, 1H), 4.38 (d, J=4.2 Hz, 1H), 3.83 (s, 3H), 3.55 (s, 3H), 2.29-2.11 (m, 1H), 0.87-0.73 (m, 6H).

Example 29. 6-methoxy-2,2-dimethyl-8-(6-methyl-7-oxo-6,7-dihydro-1H-pyrazolo[3,4-c]pyridin-4-yl)-2H-1,4-benzoxazin-3(4H)-one

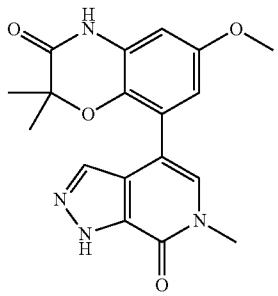

The compound of Example 29 was synthesized according to an experimental procedure analogous to that used for the synthesis of the compounds of Examples 9 and 26 to afford the title compound as an amorphous white solid (22 mg, 37%). LCMS found (M+H)$^+$: 355.1. $^1$H NMR (300 MHz, DMSO-d$_6$) δ 10.62 (s, 1H), 7.80 (s, 1H), 7.29 (s, 1H), 6.60 (d, J=2.9 Hz, 1H), 6.49 (d, J=2.9 Hz, 1H), 3.72 (s, 3H), 3.56 (s, 3H), 1.30 (s, 6H).

Example 30. 8-(6-methyl-7-oxo-6,7-dihydro-1H-pyrrolo[2,3-c]pyridin-4-yl)spiro[1,4-benzoxazine-2,1'-cyclopropan]-3(4H)-one

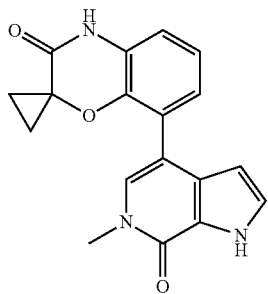 [SMILES: Cn1cc(-c2cccc3c2OC2(CC2)C(=O)N3)c2cc[nH]c2c1=O]

Step 1. methyl 1-(2-bromo-6-nitrophenoxy)cyclopropanecarboxylate

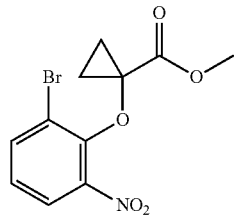 [SMILES: COC(=O)C1(Oc2c(Br)cccc2[N+](=O)[O-])CC1]

Sodium hydride in mineral oil (22 mg, 0.94 mmol) was added to a solution of methyl 1-hydroxycyclopropanecarboxylate (40 mg, 0.4 mmol) (Acros Organics cat#30211) in tetrahydrofuran (2 mL). After 10 min 15-Crown-5 (5 μL, 0.02 mmol) and 1-bromo-2-fluoro-3-nitrobenzene (100 mg, 0.4 mmol) (Ark Pharma cat# AK-35754) were added. The reaction mixture was stirred at room temperature overnight then quenched with methanol (1 mL) and partitioned between ethyl acetate and water. The combined organic layers were washed with brine, dried over MgSO$_4$, filtered, and concentrated to yield crude product. The product was purified by FCC on silica gel eluting a hexane: ethyl acetate gradient to afford methyl 1-(2-bromo-6-nitrophenoxy)cyclopropanecarboxylate as a semisolid (50 mg, 40%). LCMS calculated for C$_{11}$H$_{11}$BrNO$_5$ (M+H)$^+$: m/z=316.1, 318.1; found=315.9, 318.0.

Step 2. 8-bromospiro[1,4-benzoxazine-2,1'-cyclopropan]-3(4H)-one

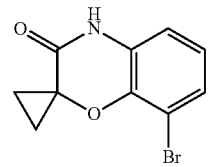 [SMILES: O=C1Nc2cccc(Br)c2OC12CC2]

Iron powder (40 mg, 0.8 mmol) was added to a mixture of methyl 1-(2-bromo-6-nitrophenoxy)cyclopropanecarboxylate (50 mg, 0.2 mmol) in acetic acid (20 mL) which was degassed with nitrogen. The reaction mixture was heated at 60° C. for 2 h and was subsequently concentrated to remove acetic acid. The resulting residue was partitioned between ethyl acetate and aqueous saturated sodium bicarbonate. The combined organic layers were washed with brine, dried over MgSO$_4$, filtered, and concentrated to afford crude 8-bromospiro[1,4-benzoxazine-2,1'-cyclopropan]-3 (4H)-one (40 mg, 100%). LCMS calculated for C$_{10}$H$_9$BrNO$_2$ (M+H)$^+$: m/z=254.1, 256.1; found=253.9, 256.0.

Step 3. 8-{6-methyl-1-[(4-methylphenyl)sulfonyl]-7-oxo-6,7-dihydro-H-pyrrolo[2,3-c]pyridin-4-yl}spiro[1,4-benzoxazine-2,1'-cyclopropan]-3(4H)-one

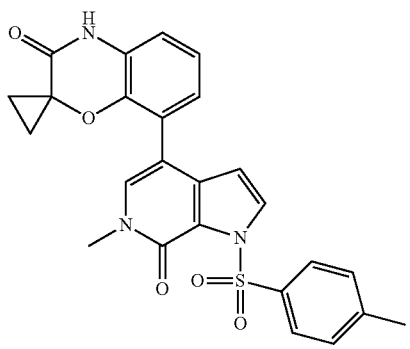 [SMILES: Cc1ccc(S(=O)(=O)n2ccc3c(-c4cccc5c4OC4(CC4)C(=O)N5)cn(C)c(=O)c32)cc1]

8-bromospiro[1,4-benzoxazine-2,1'-cyclopropan]-3(4H)-one (13 mg, 0.050 mmol) and 6-methyl-1-[(4-methylphenyl)sulfonyl]-4-(4,4, 5,5-tetramethyl-1,3,2-dioxaborolan-2-yl)-1,6-dihydro-7H-pyrrolo[2,3-c]pyridin-7-one (26 mg, 0.060 mmol) were dissolved in a mixture of 1-butanol (4 mL) and cesium fluoride (26 mg, 0.17 mmol) in water (1 mL). The reaction mixture was then degassed with nitrogen and 4-(ditert-butylphosphino)-N,N-dimethylaniline-dichloropalladium (2:1) (20 mg, 0.02 mmol) was added. The resulting mixture was heated to 100° C. for 3 h. This mixture was then cooled to room temperature and between ethyl acetate and water. The organic layer was washed with brine, dried over MgSO$_4$, filtered, and concentrated to yield crude product. The product was purified by FCC on silica gel eluting a hexane: ethyl acetate gradient to afford 8-{6-methyl-1-[(4-methylphenyl)sulfonyl]-7-oxo-6,7-dihydro-1H-pyrrolo[2,3-c]pyridin-4-yl}spiro[1,4-benzoxazine-2,1'-cyclopropan]-3(4H)-one as a semisolid (20 mg, 63%). LCMS calculated for $C_{25}H_{22}N_3O_5S$ (M+H)$^+$: m/z=476.1; found=476.1.

Step 4. 8-(6-methyl-7-oxo-6,7-dihydro-1H-pyrrolo[2,3-c]pyridin-4-yl)spiro[1,4-benzoxazine-2,1'-cyclopropan]-3(4H)-one 8-{6-Methyl-1-[(4-methylphenyl) sulfonyl]-7-oxo-6,7-dihydro-1H-pyrrolo[2,3-c]pyridin-4-yl}spiro[1,4-benzoxazine-2,1'-cyclopropan]-3(4H)-one was dissolved in a mixture of ethanol (4 mL) and 1.0 M sodium hydroxide in water (2 mL) and the resulting mixture was heated at 80° C. for 1 h. The reaction mixture was then concentrated and partitioned between ethyl acetate and water. The combined organic layers were washed with brine, dried over MgSO$_4$, filtered, and concentrated to yield crude product. The product was purified by prep HPLC on a C-18 column eluting a water:acetonitrile gradient buffered at pH 2 with TFA, to afford the title compound as an off white amorphous solid (7 mg, 40%). LCMS calculated for $C_{18}H_{16}N_3O_3$ (M+H)$^+$: m/z=322.1; found=322.1 $^1$H NMR (300 MHz, DMSO-d$_6$) δ 12.02 (s, 1H), 10.82 (s, 1H), 7.25 (t, J=2.7 Hz, 1H), 7.12 (s, 1H), 7.07-6.95 (m, 2H), 6.91 (dd, J=7.3, 2.0 Hz, 1H), 6.09 (t, J=2.2 Hz, 1H), 3.51 (s, 3H), 1.25-1.14 (m, 2H), 1.09-0.99 (m, 2H).

Example 31. 2,2-dimethyl-8-(6-methyl-7-oxo-6,7-dihydro-1H-pyrrolo[2,3-c]pyridin-4-yl)-2H-1,4-benzoxazin-3(4H)-one

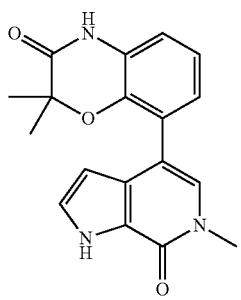

The compound of Example 31 was synthesized according to an experimental procedure analogous to that used for the synthesis of the compound of Example 1 to afford the title compound as an amorphous white solid (15 mg, 25%). LCMS found (M+H)$^+$: 324.1. $^1$H NMR (300 MHz, DMSO-d$_6$) δ 12.02 (s, 1H), 10.66 (s, 1H), 7.26 (t, J=2.7 Hz, 1H), 7.17 (s, 1H), 7.00 (s, 1H), 6.99 (d, J=2.1 Hz, 1H), 6.88 (dd, J=5.7, 3.6 Hz, 1H), 6.13 (s, 1H), 3.54 (s, 3H), 1.33 (s, 6H).

Example 32. 3,3-dimethyl-5-(6-methyl-7-oxo-6,7-dihydro-1H-pyrrolo[2,3-c]pyridin-4-yl)-3,4-dihydroquinoxalin-2(1H)-one

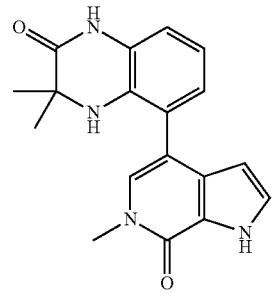 [SMILES: Cn1cc(-c2cccc3c2NC(C)(C)C(=O)N3)c2cc[nH]c2c1=O]

Step 1. methyl 2-[(2-bromo-6-nitrophenyl)amino]-2-methylpropanoate

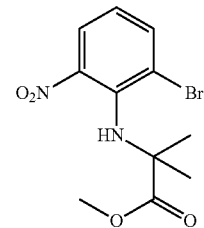 [SMILES: COC(=O)C(C)(C)Nc1c(Br)cccc1[N+](=O)[O-]]

Sodium bicarbonate (70 mg, 0.83 mmol) was added to a solution of 1-bromo-2-fluoro-3-nitrobenzene (100 mg, 0.4 mmol) and methyl 2-amino-2-methylpropanoate hydrochloride (90 mg, 0.6 mmol) (Aldrich cat# A8754) in N-methylpyrrolidinone (1 mL) and the resulting solution was heated to 100° C. overnight. The reaction mixture was then cooled to room temperature and was partitioned between ethyl acetate and water. The combined organic layers were washed with brine, dried over MgSO$_4$, filtered, and concentrated to yield a crude residue. The product was purified by FCC on silica gel eluting a hexane: ethyl acetate gradient to afford methyl 2-[(2-bromo-6-nitrophenyl)amino]-2-methylpropanoate as a semi-solid (50 mg, 30%). LCMS calculated for $C_{11}H_{14}BrN_2O_4$(M+H)$^+$: m/z=317.1, 319.1; found=317.0, 319.0.

Step 2. 3,3-dimethyl-5-(6-methyl-7-oxo-6,7-dihydro-1H-pyrrolo[2,3-c]pyridin-4-yl)-3,4-dihydroquinoxalin-2(1H)-one Using methods similar to conditions in Example 30, but using methyl 2-[(2-bromo-6-nitrophenyl)amino]-2-methylpropanoate from Step 1, the crude product was prepared. The product was purified by prep HPLC on a C-18 column eluting a water:acetonitrile gradient buffered at pH 2 with TFA, to afford the title compound as an off white amorphous solid (4 mg, 20%). LCMS calculated for $C_{18}H_{19}N_4O_2$ (M+H)$^+$: m/z=323.1; found=323.1.

Examples 33-34

The compounds of Examples 33-34 and the experimental procedures used to prepare them are set out in Table 4 below.

TABLE 4

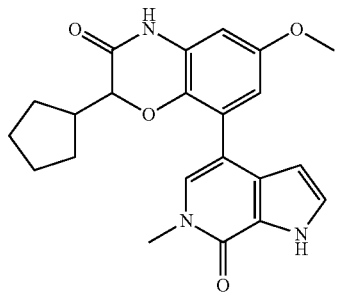 [SMILES: COc1cc2c(c(-c3cn(C)c(=O)c4[nH]ccc34)c1)OC(C1CCCC1)C(=O)N2]

| Ex. No. | Name | R⁵ | Synthetic Procedure |
|---|---|---|---|
| 33 | 2-isopropyl-8-(6-methyl-7-oxo-6,7-dihydro-1H-pyrrolo[2,3-c]pyridin-4-yl)-6-(morpholin-4-ylcarbonyl)-2H-1,4-benzoxazin-3(4H)-one | morpholine carbonyl | 20 |
| 34 | 2-isopropyl-N,N-dimethyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide | N,N-dimethyl carboxamide | 20 |

Example 35. 2-cyclopentyl-6-methoxy-8-(6-methyl-7-oxo-6,7-dihydro-1H-pyrrolo[2,3-c]pyridin-4-yl)-2H-1,4-benzoxazin-3(4H)-one

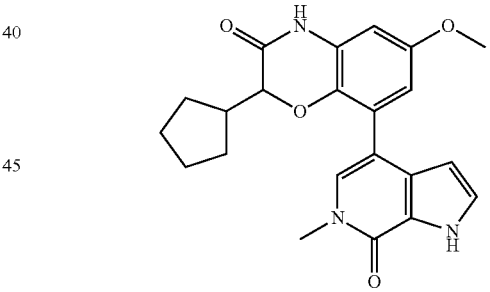

Step 1. ethyl bromo(cyclopentyl)acetate

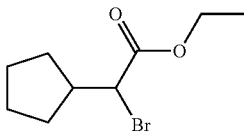

Thionyl chloride (0.35 mL, 4.8 mmol) was added dropwise to a solution of cyclopentaneacetic acid (0.5 g, 4 mmol) (Alfa Aesar cat# A15696) in 1,2-dichloroethane (20 mL) at room temperature. The reaction mixture was heated to reflux for 2 h then cooled to room temperature, at which time N-bromosuccinimide (850 mg, 4.8 mmol) and hydrogen bromide (5 µL, 0.09 mmol) (48% aqueous solution) were added successively. This mixture was then heated to reflux for 2 days. The mixture was then cooled to room temperature, ethanol (5 mL, 80 mmol) was added, and the resulting mixture was stirred for an additional 2 h at room temperature. The reaction mixture was then concentrated to give a crude residue. This residue was suspended in carbon tetrachloride, passed through a short pad of silica gel, and concentrated to afford crude ethyl bromo(cyclopentyl)acetate as an oil (0.8 g, 90%). LCMS calculated for $C_9H_{16}BrO_2$ (M+H)⁺: m/z=235.1; found=235.1.

Step 2. 2-cyclopentyl-6-methoxy-8-(6-methyl-7-oxo-6,7-dihydro-1H-pyrrolo[2,3-c]pyridin-4-yl)-2H-1,4-benzoxazin-3(4H)-one Using methods similar to conditions in Example 9, but using ethyl bromo(cyclopentyl)acetate from Step 1, the crude product was prepared. The product was purified by prep HPLC on a C-18 column eluting a water:acetonitrile gradient buffered at pH 2 with TFA to afford the title compound as an off white amorphous solid (8 mg, 40%). LCMS calculated for $C_{22}H_{24}N_3O_4$ (M+H)⁺: m/z=394.1; found=394.2. ¹H NMR (500 MHz, DMSO-d₆) δ 11.99 (s, 1H), 10.56 (s, 1H), 7.27 (s, 2H), 6.58 (d, J=2.9 Hz, 1H), 6.47 (d, J=2.9 Hz, 1H), 6.20 (s, 1H), 4.36 (d, J=6.1 Hz, 1H), 3.71 (s, 3H), 3.54 (s, 3H), 2.39-2.29 (m, 1H), 1.63-1.18 (m, 8H).

Example 35A. 2-Cyclopentyl-6-methoxy-8-(6-methyl-7-oxo-6,7-dihydro-1H-pyrrolo[2,3-c]pyridin-4-yl)-2H-1,4-benzoxazin-3(4H)-one (Enantiomer 1)

Example 35B. 2-Cyclopentyl-6-methoxy-8-(6-methyl-7-oxo-6,7-dihydro-1H-pyrrolo[2,3-c]pyridin-4-yl)-2H-1,4-benzoxazin-3(4H)-one (Enantiomer 2)

The enantiomers of compound Example 35 were separated by Chiral column HPLC using the following conditions: Column: Phenomenex Lux Cellulose C-4, 5 µm, 21.2×250 mm; Mobile phase: 60% Ethanol in Hexane; Gradient: 18 mL/min isocratic; Loading: 1 mg in 900 µL; Run time: 11 min; Retention times: 7.7 and 8.7 minutes.

Example 35A, Peak 1 (7.7 min). LCMS calculated for $C_{22}H_{24}N_3O_4$ (M+H)⁺: m/z=394.1; found=394.2. ¹H NMR (500 MHz, DMSO-d₆) δ 11.99 (s, 1H), 10.56 (s, 1H), 7.27 (s, 2H), 6.58 (d, J=2.9 Hz, 1H), 6.47 (d, J=2.9 Hz, 1H), 6.20 (s, 1H), 4.36 (d, J=6.1 Hz, 1H), 3.71 (s, 3H), 3.54 (s, 3H), 2.39-2.29 (m, 1H), 1.63-1.18 (m, 8H).

Example 35B, Peak 2 (8.7 minutes). LCMS calculated for $C_{22}H_{24}N_3O_4$ (M+H)⁺: m/z=394.1; found=394.2. ¹H NMR (500 MHz, DMSO-d₆) δ 11.99 (s, 1H), 10.56 (s, 1H), 7.27 (s, 2H), 6.58 (d, J=2.9 Hz, 1H), 6.47 (d, J=2.9 Hz, 1H), 6.20

(s, 1H), 4.36 (d, J=6.1 Hz, 1H), 3.71 (s, 3H), 3.54 (s, 3H), 2.39-2.29 (m, 1H), 1.63-1.18 (m, 8H).

Example 36. 6-(hydroxymethyl)-2-isopropyl-8-(6-methyl-7-oxo-6,7-dihydro-1H-pyrrolo[2,3-c]pyridin-4-yl)-2H-1,4-benzoxazin-3(4H)-one

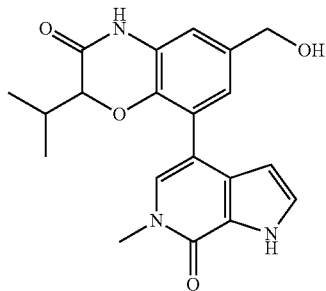 [SMILES: CC(C)C1Oc2c(cc(CO)cc2-c2cn(C)c(=O)c3[nH]ccc23)NC1=O]

Step 1. 8-bromo-6-(hydroxymethyl)-2-isopropyl-2H-1,4-benzoxazin-3(4H)-one

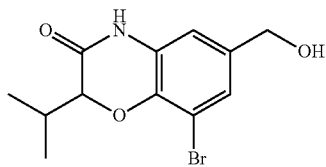 [SMILES: CC(C)C1Oc2c(Br)cc(CO)cc2NC1=O]

Isobutyl chloroformate (50 μL, 0.38 mmol) was added dropwise to a solution of 8-bromo-2-isopropyl-3-oxo-3,4-dihydro-2H-1,4-benzoxazine-6-carboxylic acid (from Example 20, 100 mg, 0.3 mmol) in tetrahydrofuran (10 mL) and triethylamine (53 μL, 0.38 mmol) cooled to 0° C. The resulting mixture was stirred for 2 h then added to a stirred solution of sodium tetrahydroborate (40 mg, 1 mmol) in water (4 mL) at 0° C. This mixture was warmed to room temperature and stirred for an additional 18 h. The mixture was then acidified using 1 N HCl and partitioned between ethyl acetate and water. The combined organic layers were washed with brine, dried over MgSO$_4$, filtered, and concentrated to yield crude product. The product was purified by FCC on silica gel eluting a hexane: ethyl acetate gradient to afford 8-bromo-6-(hydroxymethyl)-2-isopropyl-2H-1,4-benzoxazin-3(4H)-one as a semisolid (80 mg, 80%). LCMS calculated for C$_{12}$H$_{15}$BrNO$_3$ (M+H)$^+$: m/z=300.1, 302.1; found.=300.0, 302.1.

Step 2. 6-(hydroxymethyl)-2-isopropyl-8-(6-methyl-7-oxo-6,7-dihydro-1H-pyrrolo[2,3-c]pyridin-4-yl)-2H-1,4-benzoxazin-3(4H)-one Using methods similar to conditions in Example 9, but using 8-bromo-6-(hydroxymethyl)-2-isopropyl-2H-1,4-benzoxazin-3(4H)-one of Step 1, the crude product was prepared. The product was purified by prep HPLC on a C-18 column eluting a water: acetonitrile gradient buffered at pH 2 with TFA, to afford the title compound as an off white amorphous solid (50 mg, 70%). LCMS calculated for C$_{20}$H$_{22}$N$_3$O$_4$ (M+H)$^+$: m/z=368.1; found=368.1. $^1$H NMR (300 MHz, DMSO-d$_6$) δ 12.02 (s, 1H), 10.69 (s, 1H), 7.32-7.22 (m, 2H), 6.95 (d, J=1.9 Hz, 1H), 6.84 (d, J=1.8 Hz, 1H), 6.24-6.15 (m, 1H), 4.45 (d, J=4.2 Hz, 1H), 4.42 (s, 2H), 3.53 (s, 3H), 2.29-2.11 (m, 1H), 0.89-0.72 (m, 6H).

Example 37. 2-isopropyl-6-(methoxymethyl)-8-(6-methyl-7-oxo-6,7-dihydro-1H-pyrrolo[2,3-c]pyridin-4-yl)-2H-1,4-benzoxazin-3(4H)-one

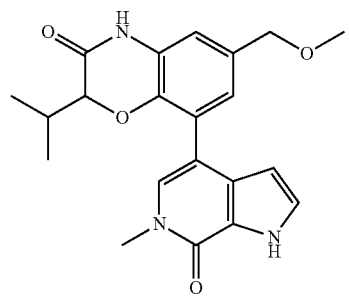 [SMILES: COCc1cc2c(c(-c3cn(C)c(=O)c4[nH]ccc34)c1)OC(C(C)C)C(=O)N2]

Step 1. 8-bromo-2-isopropyl-6-(methoxymethyl)-2H-1,4-benzoxazin-3(4H)-one

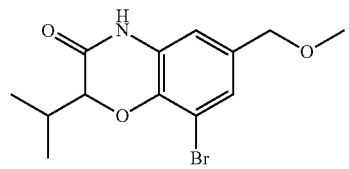 [SMILES: COCc1cc(Br)c2c(c1)NC(=O)C(C(C)C)O2]

A solution of 8-bromo-6-(hydroxymethyl)-2-isopropyl-2H-1,4-benzoxazin-3(4H)-one (20 mg, 0.07 mmol) of Example 36 in methanol (2 mL, 50 mmol) was treated with p-toluenesulfonic acid monohydrate (10 mg, 0.07 mmol) and the resulting mixture was heated in a microwave at 90° C. for 40 min. This mixture was cooled to room temperature, concentrated, and partitioned between ethyl acetate and water. The combined organic layers were washed with brine, dried over MgSO$_4$, filtered, and concentrated to afford 8-bromo-2-isopropyl-6-(methoxymethyl)-2H-1,4-benzoxazin-3(4H)-one as a clear oil (20 mg, 100%). LCMS calculated for C$_{13}$H$_{17}$BrNO$_3$ (M+H)$^+$: m/z=314.1, 316.1; found=314.0, 316.1.

Step 2. 2-isopropyl-6-(methoxymethyl)-8-(6-methyl-7-oxo-6,7-dihydro-1H-pyrrolo[2,3-c]pyridin-4-yl)-2H-1,4-benzoxazin-3(4H)-one Using methods similar to conditions in Example 9, but using 8-bromo-2-isopropyl-6-(methoxymethyl)-2H-1,4-benzoxazin-3(4H)-one from Step 1, the crude product was prepared. The product was purified by prep HPLC on a C-18 column eluting a water:acetonitrile gradient buffered at pH 2 with TFA to afford the title compound as an off white amorphous solid (6 mg, 30%). LCMS calculated for C$_{21}$H$_{24}$N$_3$O$_4$ (M+H)$^+$: m/z=382.1; found=382.1. $^1$H NMR (500 MHz, DMSO-d$_6$) δ 11.99 (s, 1H), 10.69 (s, 1H), 7.30-7.23 (m, 2H), 6.96 (d, J=1.8 Hz, 1H), 6.84 (d, J=1.9 Hz, 1H), 6.18 (t, J=2.3 Hz, 1H), 4.39 (d, J=4.2 Hz, 1H), 4.34 (s, 2H), 3.54 (s, 3H), 3.28 (s, 3H), 2.25-2.17 (m, 1H), 0.82 (dd, J=15.5, 6.8 Hz, 6H).

Example 38. 6-(Aminomethyl)-2-isopropyl-8-(6-methyl-7-oxo-6,7-dihydro-1H-pyrrolo[2,3-c]pyridin-4-yl)-2H-1,4-benzoxazin-3(4H)-one

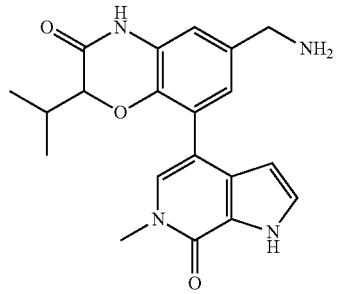 [SMILES: CC(C)C1Oc2c(cc(CN)cc2-c2cn(C)c(=O)c3[nH]ccc23)NC1=O]

Step 1. tert-butyl [(8-bromo-2-isopropyl-3-oxo-3,4-dihydro-2H-1,4-benzoxazin-6-yl)methyl]carbamate

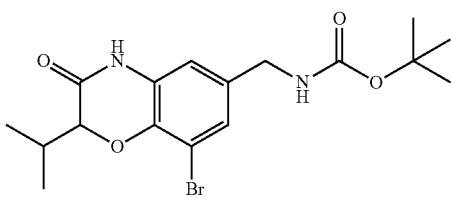 [SMILES: CC(C)C1Oc2c(Br)cc(CNC(=O)OC(C)(C)C)cc2NC1=O]

To an ice-cooled solution of 8-bromo-2-isopropyl-3-oxo-3,4-dihydro-2H-1,4-benzoxazine-6-carbonitrile (from Example 17, 100 mg, 0.3 mmol) in methanol (5 mL) was added di-tert-butyldicarbonate (100 mg, 0.7 mmol) and nickel chloride hexahydrate (8 mg, 0.03 mmol), followed by portion-wise addition of sodium tetrahydroborate (90 mg, 2 mmol). The resulting black solution was stirred at 0° C. for 30 min then warmed to room temperature and stirred overnight. $N^1$-(2-aminoethyl)ethane-1,2-diamine (10 mg, 0.1 mmol) was then added, and the mixture was concentrated to dryness. The resulting residue was dissolved in ethyl acetate and washed with 10% citric acid followed by saturated sodium bicarbonate. The combined organic layers were washed with brine, dried over $MgSO_4$, filtered, and concentrated to yield crude product. The product was purified by FCC on silica gel eluting a hexane: ethyl acetate gradient to afford tert-butyl [(8-bromo-2-isopropyl-3-oxo-3,4-dihydro-2H-1,4-benzoxazin-6-yl)methyl]carbamate as a semi-solid (100 mg, 70%). LCMS calculated for $C_{17}H_{23}BrN_2O_4$ $(M+H)^+$: m/z=399.1, 401.1; found=399.1, 401.0.

Step 2. 6-(aminomethyl)-2-isopropyl-8-(6-methyl-7-oxo-6,7-dihydro-1H-pyrrolo[2,3-c]pyridin-4-yl)-2H-1,4-benzoxazin-3(4H)-one Using methods similar to conditions in Example 9, but using tert-butyl [(8-bromo-2-isopropyl-3-oxo-3,4-dihydro-2H-1,4-benzoxazin-6-yl)methyl]carbamate from Step 1, the crude product was prepared. The product was purified by prep HPLC on a C-18 column eluting a water:acetonitrile gradient buffered at pH 10 to afford the title compound as an off white amorphous solid (5 mg, 50%). LCMS calculated for $C_{20}H_{23}N_4O_3$ $(M+H)^+$: m/z=367.1; found=367.2.

Example 39. N-{[2-isopropyl-8-(6-methyl-7-oxo-6,7-dihydro-1H-pyrrolo[2,3-c]pyridin-4-yl)-3-oxo-3,4-dihydro-2H-1,4-benzoxazin-6-yl]methyl}ethanesulfonamide

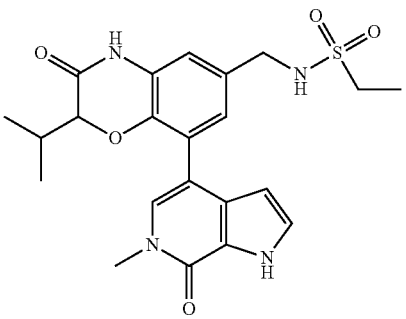 [SMILES: CCS(=O)(=O)NCc1cc2c(c(-c3cn(C)c(=O)c4[nH]ccc34)c1)OC(C(C)C)C(=O)N2]

Step 1. 6-(aminomethyl)-2-isopropyl-8-{6-methyl-[(4-ethylphenyl)sulfonyl]-7-oxo-6,7-dihydro-1H-pyrrolo[2,3-c]pyridin-4-yl}-2H-1,4-benzoxazin-3(4H)-one hydrochloride

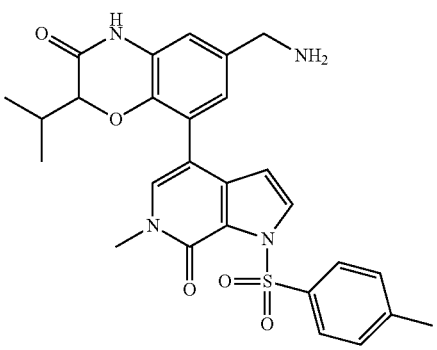 [SMILES: Cc1ccc(S(=O)(=O)n2ccc3c(-c4cc(CN)cc5c4OC(C(C)C)C(=O)N5)cn(C)c(=O)c32)cc1]

tert-Butyl [(2-isopropyl-8-{6-methyl-1-[(4-methylphenyl)sulfonyl]-7-oxo-6,7-dihydro-1H-pyrrolo[2, 3-c]pyridin-4-yl}-3-oxo-3,4-dihydro-2H-1,4-benzoxazin-6-yl)methyl]carbamate (100 mg, 0.2 mmol) of Example 38 was dissolved in 4 M hydrogen chloride in dioxane (5 mL) at room temperature and the mixture was stirred for 2 h. The reaction was then concentrated to afford crude 6-(aminomethyl)-2-isopropyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one hydrochloride as a white salt (100 mg, 100%). LCMS calculated for $C_{27}H_{29}N_4O_5S$ $(M+H)^+$: m/z=521.1; found=521.2.

Step 2. N-[(2-isopropyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazin-6-yl)methyl]ethanesulfonamide

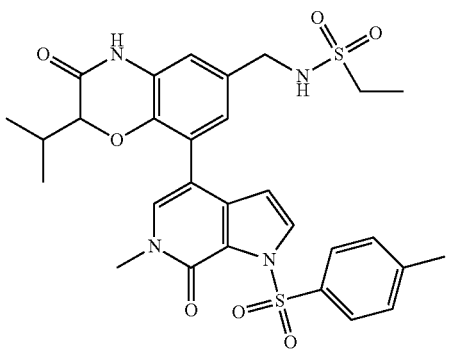 [SMILES: CCS(=O)(=O)NCc1cc2c(c(-c3cn(C)c(=O)c4c3ccn4S(=O)(=O)c3ccc(C)cc3)c1)OC(C(C)C)C(=O)N2]

Ethanesulfonyl chloride (4.1 mg, 0.032 mmol) was added to a solution of 6-(aminomethyl)-2-isopropyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one hydrochloride (16 mg, 0.029 mmol) in methylene chloride (1.0 mL) and triethylamine (8 μL, 0.06 mmol) at 0° C. and the mixture was stirred at 0° C. for 30 min. The mixture was partitioned between ethyl acetate and water. The organic layer was then washed with brine, dried over MgSO$_4$, filtered, and concentrated to afford crude N-[(2-isopropyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazin-6-yl)methyl]ethanesulfonamide as a semisolid (15 mg, 85%). LCMS calculated for $C_{29}H_{33}N_4O_7S_2$ (M+H)$^+$: m/z=613.1; found=613.2.

Step 3. N-{[2-isopropyl-8-(6-methyl-7-oxo-6,7-dihydro-1H-pyrrolo[2,3-c]pyridin-4-yl)-3-oxo-3,4-dihydro-2H-1,4-benzoxazin-6-yl]methyl}ethanesulfonamide Using methods similar to conditions in Example 9, but using N-[(2-isopropyl-8-{6-methyl-1-[(4-methylphenyl)sulfonyl]-7-oxo-6,7-dihydro-1H-pyrrolo[2,3-c]pyridin-4-yl}-3-oxo-3,4-dihydro-2H-1,4-benzoxazin-6-yl)methyl]ethanesulfonamide from Step 2, the crude product was prepared. The product was purified by prep HPLC on a C-18 column eluting a water: acetonitrile gradient buffered at pH 10 to afford the title compound as an off white amorphous solid (6 mg, 40%). LCMS calculated for $C_{22}H_{27}N_4O_5S$ (M+H)$^+$: m/z=459.1.1; found=459.2. $^1$H NMR (300 MHz, DMSO-d$_6$) δ 12.03 (s, 1H), 10.74 (s, 1H), 7.57 (t, J=6.2 Hz, 1H), 7.32-7.26 (m, 1H), 7.25 (s, 1H), 7.01 (d, J=1.9 Hz, 1H), 6.85 (d, J=1.8 Hz, 1H), 6.23 (d, J=2.5 Hz, 1H), 4.37 (d, J=4.3 Hz, 1H), 4.06 (d, J=6.2 Hz, 2H), 3.54 (s, 3H), 2.94 (q, J=7.3 Hz, 2H), 2.29-2.12 (m, 1H), 1.16 (t, J=7.4 Hz, 3H), 0.81 (dd, J=14.0, 6.8 Hz, 6H).

Examples 40-41

The compounds of Examples 40-41 and the experimental procedures used to prepare them are set out in Table 5 below.

TABLE 5

| Ex. No. | Name | R$^5$ | Synthetic Procedure |
|---|---|---|---|
| 40 | N-{[2-isopropyl-8-(6-methyl-7-oxo-6,7-dihydro-1H-pyrrolo[2,3-c]pyridin-4-yl)-3-oxo-3,4-dihydro-2H-1,4-benzoxazin-6-yl]methyl}acetamide | ![structure] | Ex. No. 39 |
| 41 | 2-isopropyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide | ![structure] | Ex. No. 20 |

Example 42. 2-Cyclopentyl-6-methoxy-8-(6-methyl-7-oxo-6,7-dihydro-1H-pyrazolo[3,4-c]pyridin-4-yl)-2H-1,4-benzoxazin-3(4H)-one

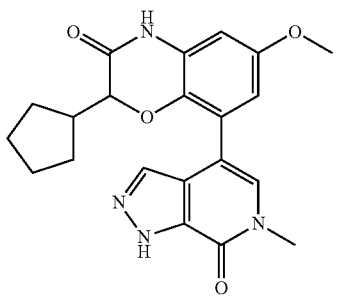 [SMILES: COc1cc2c(c(-c3cn(C)c(=O)c4[nH]ncc34)c1)OC(C1CCCC1)C(=O)N2]

The compound of Example 42 was synthesized according to an experimental procedure analogous to that used for the synthesis of the compounds of Examples 35 and 26 to afford the title compound as an amorphous white solid (50 mg, 50%). LCMS found (M+H)$^+$=395.2. $^1$H NMR (300 MHz, DMSO-d$_6$) δ 10.61 (s, 1H), 7.80 (s, 1H), 7.35 (s, 1H), 6.59 (d, J=2.9 Hz, 1H), 6.49 (d, 1H), 4.44 (d, J=5.9 Hz, 1H), 3.72 (s, 3H), 3.26 (s, 3H), 2.39-2.23 (m, 1H), 1.59-1.19 (m, 8H).

Example 42A. 2-cyclopentyl-6-methoxy-8-(6-methyl-7-oxo-6,7-dihydro-1H-pyrazolo[3,4-c]pyridin-4-yl)-2H-1,4-benzoxazin-3(4H)-one (Enantiomer 1)

Example 42B. 2-cyclopentyl-6-methoxy-8-(6-methyl-7-oxo-6,7-dihydro-1H-pyrazolo[3,4-c]pyridin-4-yl)-2H-1,4-benzoxazin-3(4H)-one (Enantiomer 2)

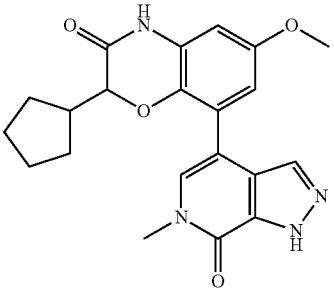

Step 1. 2-cyclopentyl-6-methoxy-8-(6-methyl-7-oxo-1-{[2-(trimethylsilyl)ethoxy]methyl}-6,7-dihydro-1H-pyrazolo[3,4-c]pyridin-4-yl)-2H-1,4-benzoxazin-3(4H)-one

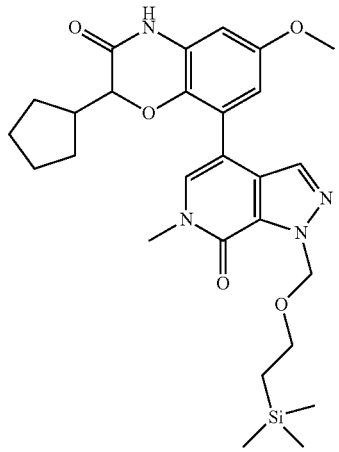 [SMILES: COc1cc2c(c(-c3cn(C)c(=O)c4c3cnn4COCC[Si](C)(C)C)c1)OC(C1CCCC1)C(=O)N2]

Using methods similar to conditions in Example 42, the intermediate product 2-cyclopentyl-6-methoxy-8-(6-methyl-7-oxo-1-{[2-(trimethylsilyl)ethoxy]methyl}-6,7-dihydro-1H-pyrazolo[3,4-c]pyridin-4-yl)-2H-1,4-benzoxazin-3(4H)-one was prepared as a pair of enantiomers. The enantiomers were separated by chiral column HPLC using the following conditions: Column: Phenomenex Lux Cellulose C-4, 5 µm, 21.2×250 mm; Mobile phase: 60% Ethanol in Hexane; Gradient: 18 mL/min isocratic; Loading: 1 mg in 900 µL; Run time: 7 min.; Retention time: 2.9 and 5.0 minutes.

Intermediate Peak 1 (2.9 minutes). LCMS calculated for $C_{27}H_{37}N_4O_5Si$ $(M+H)^+$: m/z=525.1; found=525.2.

Intermediate Peak 2 (5.0 minutes). LCMS calculated for $C_{27}H_{37}N_4O_5Si$ $(M+H)^+$: m/z=525.1; found=525.2.

Step 2. 2-cyclopentyl-6-methoxy-8-(6-methyl-7-oxo-6,7-dihydro-1H-pyrazolo[3,4-c]pyridin-4-yl)-2H-1,4-benzoxazin-3(4H)-one Using methods similar to conditions in Example 42, but using the purified enantiomers of Step 1, the crude product was prepared. The product was purified by prep HPLC on a C-18 column eluting a water:acetonitrile gradient buffered at pH 10, to afford the title compound as an off white amorphous solid.

Example 42A. Peak 1. LCMS calculated for $C_{21}H_{23}N_4O_4$ $(M+H)^+$: m/z=395.1; found=395.1. $^1H$ NMR (300 MHz, DMSO-$d_6$) δ 10.61 (s, 1H), 7.80 (s, 1H), 7.35 (s, 1H), 6.59 (d, J=2.9 Hz, 1H), 6.49 (d, 1H), 4.44 (d, J=5.9 Hz, 1H), 3.72 (s, 3H), 3.26 (s, 3H), 2.39-2.23 (m, 1H), 1.59-1.19 (m, 8H).

Example 42B. Peak 2. LCMS calculated for $C_{21}H_{23}N_4O_4$ $(M+H)^+$: m/z=395.1; found=395.1. $^1H$ NMR (300 MHz, DMSO-$d_6$) δ 10.61 (s, 1H), 7.80 (s, 1H), 7.35 (s, 1H), 6.59 (d, J=2.9 Hz, 1H), 6.49 (d, 1H), 4.44 (d, J=5.9 Hz, 1H), 3.72 (s, 3H), 3.26 (s, 3H), 2.39-2.23 (m, 1H), 1.59-1.19 (m, 8H).

Example 43. 6-(2-furyl)-2-isopropyl-8-(6-methyl-7-oxo-6,7-dihydro-1H-pyrrolo[2,3-c]pyridin-4-yl)-2H-1,4-benzoxazin-3(4H)-one

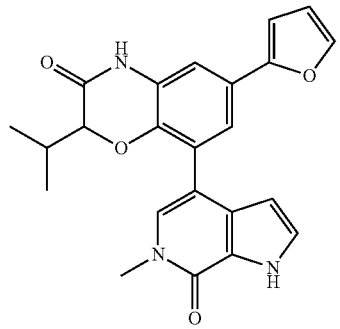 [SMILES: CC(C)C1Oc2c(cc(-c3ccco3)cc2-c2cn(C)c(=O)c3[nH]ccc23)NC1=O]

The compound of Example 43 was synthesized according to an experimental procedure analogous to that used for the synthesis of the compound of Example 28 to afford the title compound as an amorphous white solid (15 mg, 25%). LCMS found $(M+H)^+$=404.1. $^1H$ NMR (300 MHz, DMSO-$d_6$) δ 12.22 (s, 1H), 10.76 (s, 1H), 7.74 (s, 1H), 7.42-7.36 (m, 1H), 7.31 (d, J=20.1 Hz, 2H), 7.02 (d, J=8.3 Hz, 1H), 6.85 (s, 2H), 6.77 (s, 1H), 4.38 (d, J=5.4 Hz, 1H), 3.59 (s, 3H), 2.24-2.10 (m, 1H), 1.02 (d, J=6.9 Hz, 3H), 0.94 (d, J=6.7 Hz, 3H).

Example 44. 2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one

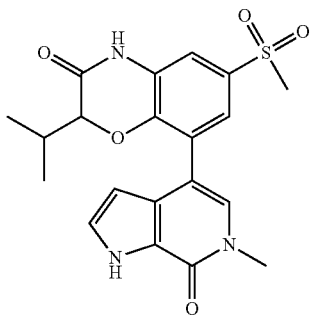

Step 1. 2-[2-hydroxy-5-(methylsulfonyl)phenyl]-1H-isoindole-1,3(2H)-dione

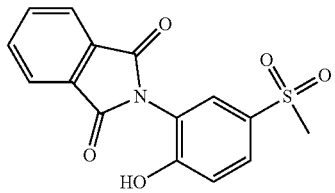 [SMILES: CS(=O)(=O)c1ccc(O)c(N2C(=O)c3ccccc3C2=O)c1]

Phthalic anhydride (1.7 g, 12 mmol) was added to a solution of 2-amino-4-(methylsulfonyl)phenol (2.0 g, 11 mmol) (TCI cat#A2198) in acetic acid (40.0 mL) and the resulting mixture was heated to 120° C. for 18 h. The reaction was then cooled to room temperature and poured over water (150 mL), where it slowly formed a precipitate. The solids were collected and dried to afford 2-[2-hydroxy-5-(methylsulfonyl)phenyl]-1H-isoindole-1,3(2H)-dione as a tan crystalline solid (3.0 gm, 80%). LCMS calculated for $C_{15}H_{12}NO_5S$ $(M+H)^+$: m/z=318.1; found=318.0.

Step 2. 2-[3-bromo-2-hydroxy-5-(methylsulfonyl)phenyl]-1H-isoindole-1,3(2H)-dione

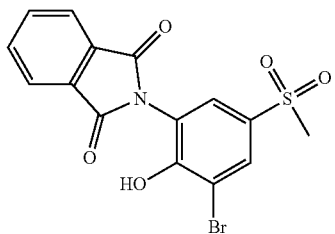 [SMILES: CS(=O)(=O)c1cc(Br)c(O)c(N2C(=O)c3ccccc3C2=O)c1]

Bromine (0.52 mL, 10 mmol) in acetic acid (2 mL) was slowly added to a solution of 2-[2-hydroxy-5-(methylsulfonyl)phenyl]-1H-isoindole-1,3(2H)-dione (3.2 g, 10. mmol) in acetic acid (160 mL) and ferric chloride (0.3 g, 2 mmol) in water (32 mL) at room temperature. The reaction mixture was stirred for 2 h and then diluted with water to yield a slurry. The solids were filtered off, washed with water, and dried to afford 2-[3-bromo-2-hydroxy-5-(methylsulfonyl)phenyl]-1H-isoindole-1,3(2H)-dione as an off white powder (3.1 g, 78%). LCMS calculated for $C_{15}H_{11}BrNO_5S$ $(M+H)^+$: m/z=396.1, 398.1; found=396.0, 398.0.

Step 3. 2-amino-6-bromo-4-(methylsulfonyl)phenol

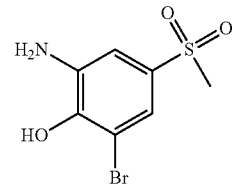

Hydrazine (0.48 mL, 15 mmol) was added to a solution of 2-[3-bromo-2-hydroxy-5-(methylsulfonyl)phenyl]-1H-isoindole-1,3(2H)-dione (3.0 g, 7.6 mmol) in ethanol (150 mL) at room temperature. The reaction was stirred at room temperature for 15 minutes, forming a slurry. The mixture was then heated to 100° C. for 18 h, cooled to room temperature, filtered, and the mother liquor was concentrated in vacuo to yield semisolid residue. This residue was suspended in ethyl acetate, filtered, and concentrated to afford 2-amino-6-bromo-4-(methylsulfonyl)phenol as a viscous oil (1.8 g, 90%). LCMS calculated for $C_7H_9BrNO_3S$ $(M+H)^+$: m/z=266.1, 268.1; found=265.9, 267.9.

Step 4. 2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one Using methods similar to conditions in Example 9, but using 2-amino-6-bromo-4-(methylsulfonyl)phenol from Step 1, the crude product was prepared. The product was purified by prep HPLC on a C-18 column eluting a water:acetonitrile gradient buffered at pH 10 to afford the title compound as an off white amorphous solid (55 mg, 68%). LCMS calculated for $C_{20}H_{22}N_3O_5S$ $(M+H)^+$: m/z=416.1; found=416.1. $^1H$ NMR (300 MHz, DMSO-$d_6$) δ 12.09 (s, 1H), 11.03 (s, 1H), 7.55 (d, J=2.2 Hz, 1H), 7.38 (s, 2H), 7.29 (t, J=2.6 Hz, 1H), 6.21 (s, 1H), 4.62 (d, J=3.9 Hz, 1H), 3.55 (s, 3H), 3.20 (s, 3H), 2.32-2.18 (m, 1H), 0.80 (d, J=6.7 Hz, 6H).

Example 44A. 2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one Example 44B. 2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one

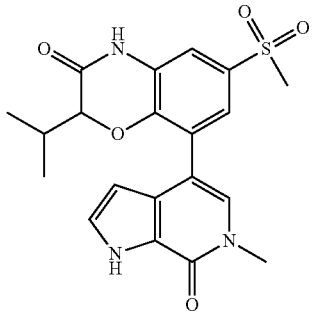 [SMILES: CC(C)C1Oc2c(cc(S(C)(=O)=O)cc2-c2cn(C)c(=O)c3[nH]ccc23)NC1=O]

The enantiomers of compound Example 44 were separated by prep chiral column chromatography using the following conditions: Column: phenomenex Lux Cellulose C-4, 5 µm, 21, 2×250 mm; Mobile phase: 80% EtOH/Hexanes; Gradient condition: isocratic at 18 mL/min; Loading: 1.5 mg in 900 µL; Run time: 17 min; Peak retention times: 11.6 and 14.8 min.

Example 44A. Peak 1 (11.6 min) as a solid residue. LCMS calculated for $C_{20}H_{22}N_3O_5S$ $(M+H)^+$: m/z=416.1; found=416.1. $^1$H NMR (300 MHz, DMSO-$d_6$) δ 12.09 (s, 1H), 11.03 (s, 1H), 7.55 (d, J=2.2 Hz, 1H), 7.38 (s, 2H), 7.29 (t, J=2.6 Hz, 1H), 6.21 (s, 1H), 4.62 (d, J=3.9 Hz, 1H), 3.55 (s, 3H), 3.20 (s, 3H), 2.32-2.18 (m, 1H), 0.80 (d, J=6.7 Hz, 6H).

Example 44B. Peak 2 (14.8 min) as a solid residue. LCMS calculated for $C_{20}H_{22}N_3O_5S$ $(M+H)^+$: m/z=416.1; found=416.1. $^1$H NMR (300 MHz, DMSO-$d_6$) δ 12.09 (s, 1H), 11.03 (s, 1H), 7.55 (d, J=2.2 Hz, 1H), 7.38 (s, 2H), 7.29 (t, J=2.6 Hz, 1H), 6.21 (s, 1H), 4.62 (d, J=3.9 Hz, 1H), 3.55 (s, 3H), 3.20 (s, 3H), 2.32-2.18 (m, 1H), 0.80 (d, J=6.7 Hz, 6H).

Examples 45-47

The compounds of Examples 45-47 and the experimental procedures used to prepare them are set out in Table 6 below.

TABLE 6

| Ex. No. | Name | $R^1$ | $R^2$ | $R^3$ | Synthetic Procedure |
|---|---|---|---|---|---|
| 45 | 2,2-dimethyl-8-(6-methyl-7-oxo-6,7-dihydro-1H-pyrrolo[2,3-c]pyridin-4-yl)-6-(methylsulfonyl)-2H-1,4-benzoxazin-3(4H)-one | CH₃— | CH₃— | H | 44 |
| 46 | 8-(6-methyl-7-oxo-6,7-dihydro-1H-pyrrolo[2,3-c]pyridin-4-yl)-6-(methylsulfonyl)-2-phenyl-2H-1,4-benzoxazin-3(4H)-one | (phenyl) | H | H | 44 |
| 47 | 2-isopropyl-4-methyl-8-(6-methyl-7-oxo-6,7-dihydro-1H-pyrrolo[2,3-c]pyridin-4-yl)-6-(methylsulfonyl)-2H-1,4-benzoxazin-3(4H)-one | i-Prop | H | Me | 44, 8 |

Example 47A. 2-isopropyl-4-methyl-8-(6-methyl-7-oxo-6,7-dihydro-1H-pyrrolo[2,3-c]pyridin-4-yl)-6-(methylsulfonyl)-2H-1,4-benzoxazin-3(4H)-one Example 47B. 2-isopropyl-4-methyl-8-(6-methyl-7-oxo-6,7-dihydro-1H-pyrrolo[2,3-c]pyridin-4-yl)-6-(methylsulfonyl)-2H-1,4-benzoxazin-3(4H)-one

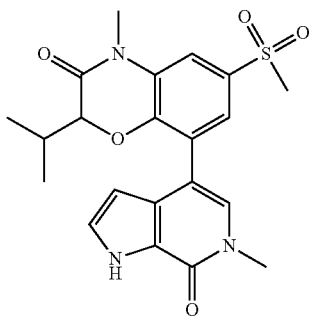 [SMILES: CC(C)C1Oc2c(-c3cn(C)c(=O)c4[nH]ccc34)cc(S(C)(=O)=O)cc2N(C)C1=O]

The enantiomers of compound Example 47 were separated by prep chiral column chromatography using the following conditions: Column: Chiralpak IA, 5 μm, 21, 2×250 mm; Mobile phase: 80% EtOH/Hexanes; Gradient condition: isocratic at 8 mL/min; Loading: 16.0 mg in 900 μL; Run time: 70 min; Peak retention times: 27.3 and 51.3 min.

Example 47A, Peak 1 (27.3 min). LCMS calculated for $C_{21}H_{24}N_3O_5S$ (M+H)$^+$: m/z=430.1; found=430.1. $^1$H NMR (300 MHz, DMSO-$d_6$) δ 12.06 (s, 1H), 7.58 (d, J=2.1 Hz, 1H), 7.52 (d, J=2.1 Hz, 1H), 7.34 (s, 1H), 7.25 (d, J=2.8 Hz, 1H), 6.15 (d, J=2.8 Hz, 1H), 4.59 (d, J=4.2 Hz, 1H), 3.51 (s, 3H), 3.34 (s, 3H), 3.23 (s, 3H), 2.25-2.13 (m, 1H), 0.73 (dd, J=6.7, 4.8 Hz, 6H).

Example 47B, Peak 2 (51.3 min). LCMS calculated for $C_{21}H_{24}N_3O_5S$ (M+H)$^+$: m/z=430.1; found=430.1. $^1$H NMR (300 MHz, DMSO-$d_6$) δ 12.06 (s, 1H), 7.58 (d, J=2.1 Hz, 1H), 7.52 (d, J=2.1 Hz, 1H), 7.34 (s, 1H), 7.25 (d, J=2.8 Hz, 1H), 6.15 (d, J=2.8 Hz, 1H), 4.59 (d, J=4.2 Hz, 1H), 3.51 (s, 3H), 3.34 (s, 3H), 3.23 (s, 3H), 2.25-2.13 (m, 1H), 0.73 (dd, J=6.7, 4.8 Hz, 6H).

Examples 48-49

The compounds of Examples 48-49 and the experimental procedures used to prepare them are set out in Table 7 below.

TABLE 7

| Ex. No. | Name | R$^1$ | R$^5$ | Synthetic Procedure |
|---|---|---|---|---|
| 48 | 2-(2-hydroxyethyl)-8-(6-methyl-7-oxo-6,7-dihydro-1H-pyrrolo[2,3-c]pyridin-4-yl)-6-(methylsulfonyl)-2H-1,4-benzoxazin-3(4H)-one | HO-CH₂CH₂- | -S(O)₂CH₃ | Ex. No. 44 |
| 49 | 6-acetyl-2-isopropyl-8-(6-methyl-7-oxo-6,7-dihydro-1H-pyrrolo[2,3-c]pyridin-4-yl)-2H-1,4-benzoxazin-3(4H)-one | i-Prop | -C(O)CH₃ | Ex. No. 9 |

Example 50. 6-(1-hydroxyethyl)-2-isopropyl-8-(6-methyl-7-oxo-6,7-dihydro-1H-pyrrolo[2,3-c]pyridin-4-yl)-2H-1,4-benzoxazin-3(4H)-one

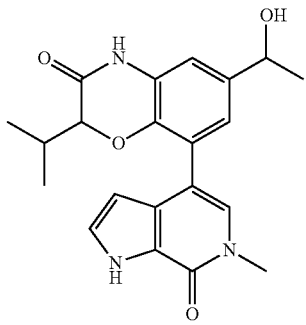 [SMILES: CC(O)c1cc2c(c(-c3cn(C)c(=O)c4[nH]ccc34)c1)OC(C(C)C)C(=O)N2]

6-Acetyl-2-isopropyl-8-(6-methyl-7-oxo-6,7-dihydro-1H-pyrrolo[2,3-c]pyridin-4-yl)-2H-1,4-benzoxazin-3(4H)-one (from Example 49, 0.050 g, 0.13 mmol) was dissolved in methanol (5.0 mL) at room temperature and sodium tetrahydroborate (0.010 g, 0.26 mmol) was added. The reaction mixture was stirred for 1 h and the product was purified without workup by prep HPLC on a C-18 column eluting a water:acetonitrile gradient buffered at pH 10 to afford the title compound as a white amorphous solid (25 mg, 50%). LCMS calculated for $C_{21}H_{24}N_3O_4$ $(M+H)^+$: m/z=382.1; found: 382.2. $^1$H NMR (300 MHz, DMSO-$d_6$) δ 11.96 (s, 1H), 10.61 (s, 1H), 7.25-7.13 (m, 2H), 6.93 (dd, J=5.3, 1.9 Hz, 1H), 6.82 (dd, J=5.8, 1.9 Hz, 1H), 6.14 (s, 1H), 5.09 (d, J=3.9 Hz, 1H), 4.68-4.52 (m, 1H), 4.30 (d, J=3.7 Hz, 1H), 3.49 (s, 3H), 2.23-2.05 (m, 1H), 1.25 (d, J=6.3 Hz, 3H), 0.76 (dd, J=12.5, 6.8 Hz, 6H).

Example 51. 6-(ethylsulfonyl)-2-isopropyl-8-(6-methyl-7-oxo-6,7-dihydro-1H-pyrrolo[2,3-c]pyridin-4-yl)-2H-1,4-benzoxazin-3(4H)-one

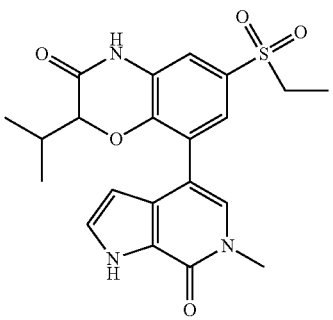 [SMILES: CCS(=O)(=O)c1cc2c(c(-c3cn(C)c(=O)c4[nH]ccc34)c1)OC(C(C)C)C(=O)N2]

Step 1. 4-(ethylthio)phenol

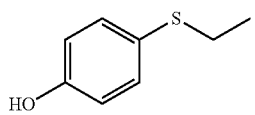

4-Mercaptophenol (0.5 g, 4 mmol) (Aldrich cat#559938-5) was dissolved in acetone (10.0 mL) and potassium carbonate (0.684 g, 4.95 mmol) and iodoethane (0.396 mL, 4.95 mmol) were added. The reaction mixture was stirred at room temperature for 2 h, diluted with ethyl acetate, and filtered. The organic layer was concentrated in vacuo to yield a yellow oil. The product was purified by FCC on silica gel eluting a hexane: ethyl acetate gradient to afford 4-(ethylthio)phenol as a clear oil which crystallized upon sitting (0.5 g, 80%).

Step 2. 4-(ethylsulfonyl)phenol

Oxone (0.99 g, 6.5 mmol) (Aldrich cat#22803-6) was added in portions to a solution of 4-(ethylthio)phenol (0.50 g, 3.2 mmol) in ethanol (10.0 mL) and water (10.0 mL) at room temperature. The reaction mixture was stirred for 18 h then partitioned between ethyl acetate and water. The combined organic layers were washed with brine, dried over magnesium sulfate, and concentrated in vacuo to afford 4-(ethylsulfonyl)phenol as a semisolid (0.58 g, 96%). LCMS calculated for $C_8H_{11}O_3S$ $(M+H)^+$: m/z=187.0; found: 187.0.

Step 3. 4-(ethylsulfonyl)-2-nitrophenol

Nitric acid (0.1 mL, 3 mmol) was added to a mixture of 4-(ethylsulfonyl)phenol (0.5 g, 3 mmol) in acetic acid (9 mL) at room temperature. The mixture was heated to 80° C. for 3 h then cooled to room temperature and partitioned between ethyl acetate and water. The combined organic layers were washed with brine, dried over MgSO$_4$, filtered, and concentrated to yield crude product. The product was crystallized from ethyl ether to afford 4-(ethylsulfonyl)-2-nitrophenol as a pale yellow solid (0.59 g, 100%). LCMS calculated for $C_8H_{10}NO_5S$ $(M+H)^+$: m/z=232.1; found: 232.0.

Step 4. 2-bromo-4-(ethylsulfonyl)-6-nitrophenol

Bromine (0.41 g, 2.6 mmol) in acetic acid (5 mL) was added to a solution of 4-(ethylsulfonyl)-2-nitrophenol (0.6 g, 2 mmol) in acetic acid (20 mL) and ferric chloride (0.08 g, 0.5 mmol) in water (0.3 mL) at room temperature and the resulting mixture was stirred for 4 h. This mixture was then diluted with water (70 mL), forming a slurry. The solids were collected, washed with water, and dried to afford 2-bromo-4-(ethylsulfonyl)-6-nitrophenol as an off white powder (0.72 gm, 80%). LCMS calculated for $C_8H_9BrNO_5$ $(M+H)^+$: m/z=310.0, 312.0; found: 310.0, 311.9.

Step 5. 2-amino-6-bromo-4-(ethylsulfonyl)phenol

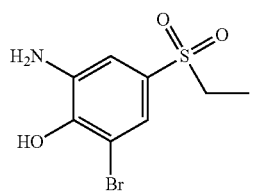

2-Bromo-4-(ethylsulfonyl)-6-nitrophenol (0.20 g, 0.64 mmol) was dissolved in ethanol (7.0 mL, 120 mmol), degassed with nitrogen, and Raney Nickel (75 mg) was added. The reaction mixture was stirred under a hydrogen atmosphere for 2 h. The mixture was decanted from the solids and concentrated in vacuo to afford 2-amino-6-bromo-4-(ethylsulfonyl)phenol as a glass (0.11 g, 47%). LCMS calculated for $C_8H_{11}BrNO_3S$ (M+H): m/z=280.1, 282.1; found: 280.0, 282.0.

Step 6. 6-(ethylsulfonyl)-2-isopropyl-8-(6-methyl-7-oxo-6,7-dihydro-1H-pyrrolo[2,3-c]pyridin-4-yl)-2H-1,4-benzoxazin-3(4H)-one Using methods similar to conditions in Example 44, but using 2-amino-6-bromo-4-(ethylsulfonyl)phenol from Step 5, the crude product was prepared. The product was purified by prep HPLC on a C-18 column eluting a water:acetonitrile gradient buffered at pH 10 to afford the title compound as an off white amorphous solid (25 mg, 20%). LCMS calculated for $C_{21}H_{24}N_3O_5S$ (M+H): m/z=430.1; found 430.2. $^1$H NMR (300 MHz, DMSO-$d_6$) δ 12.05 (s, 1H), 10.95 (bs, 1H), 7.43 (d, J=2.2 Hz, 1H), 7.33 (s, 1H), 7.27 (dd, J=10.2, 2.4 Hz, 2H), 6.14 (d, J=2.7 Hz, 1H), 4.57 (d, J=3.8 Hz, 1H), 3.50 (s, 3H), 3.21 (q, 2H), 2.28-2.12 (m, 1H), 1.07 (t, J=7.3 Hz, 3H), 0.76 (d, J=6.7 Hz, 6H).

Examples 52-56

The compounds of Examples 52-56 and the experimental procedures used to prepare them are set out in Table 8 below.

TABLE 8

| Ex. No. | Name | $R^3$ | $R^5$ | Synthetic Procedure |
|---|---|---|---|---|
| 52 | 2-isopropyl-6-(isopropylsulfonyl)-8-(6-methyl-7-oxo-6,7-dihydro-1H-pyrrolo[2,3-c]pyridin-4-yl)-2H-1,4-benzoxazin-3(4H)-one | H | -S(O)$_2$-iPr | 44 |
| 53 | 4-(cyclopropylmethyl)-2-isopropyl-8-(6-methyl-7-oxo-6,7-dihydro-1H-pyrrolo[2,3-c]pyridin-4-yl)-6-(methyslulfonyl)-2H-1,4-benzoxazin-3(4H)-one | CH$_2$-cyclopropyl | -S(O)$_2$Me | 44, 8 |
| 54 | 4-ethyl-2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one | Et | -S(O)$_2$Me | 44, 8 |
| 55 | 6-(ethylsulfonyl)-2-isopropyl-4-methyl-8-(6-methyl-7-oxo-6,7-dihydro-1H-pyrrolo[2,3-c]pyridin-4-yl)-2H-1,4-benzoxazin-3(4H)-one | Me | -S(O)$_2$Et | 44, 8 |

TABLE 8-continued

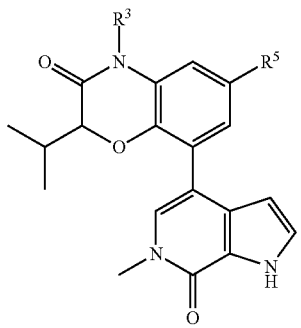

| Ex. No. | Name | R³ | R⁵ | Synthetic Procedure |
|---|---|---|---|---|
| 56 | 2-isopropyl-6-(isopropylsulfonyl)-4-methyl-8-(6-methyl-7-oxo-6,7-dihydro-1H-pyrrolo[2,3-c]pyridin-4-yl)-2H-1,4-benzoxazin-3(4H)-one | Me | 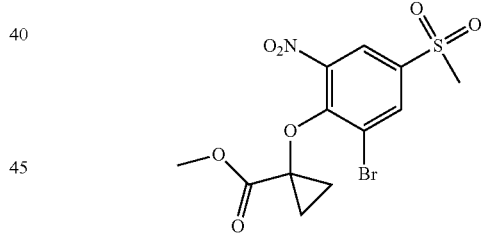 | 44, 8 |

Example 57. 8-(6-methyl-7-oxo-6,7-dihydro-1H-pyrrolo[2,3-c]pyridin-4-yl)-6-(methylsulfonyl)spiro[1,4-benzoxazine-2,1'-cyclopropan]-3(4H)-one

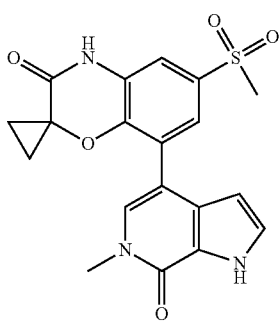 [SMILES: Cn1cc(-c2cc(S(C)(=O)=O)cc3c2OC2(CC2)C(=O)N3)c2cc[nH]c2c1=O]

Step 1.
1-bromo-2-fluoro-5-(methylsulfonyl)-3-nitrobenzene

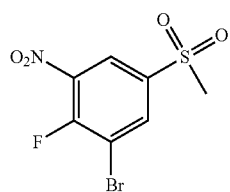

Bromine (1 g, 9 mmol) was added dropwise to a solution of 1-fluoro-4-(methylsulfonyl)-2-nitrobenzene (2 g, 9 mmol) (Oakwood cat#009288) in sulfuric acid (10 mL), followed by dropwise addition of nitric acid (0.42 mL, 10. mmol). The resulting mixture was heated to 80° C. for 5 h then cooled and poured over ice. The aqueous layer was extracted with methylene chloride and the combined organic layers were washed with saturated Na₂S₂O₃, brine, dried over MgSO₄, filtered, and concentrated to yield crude material. The product was purified by FCC on silica gel eluting a hexane: ethyl acetate gradient to afford 1-bromo-2-fluoro-5-(methylsulfonyl)-3-nitrobenzene as a glass (0.80 g, 30%). LCMS calculated for $C_7H_6BrNO_4S$ (M+H)⁺: m/z=298.1, 300.1; found 277.9, 299.7.

Step 2. methyl 1-[2-bromo-4-(methylsulfonyl)-6-nitrophenoxy]cyclopropanecarboxylate Sodium hydride in mineral oil (45 mg, 1.9 mmol) was added to a solution of methyl 1-hydroxycyclopropanecarboxylate (40 mg, 0.3 mmol) in tetrahydrofuran (5 mL). After 10 min 15-Crown-5 (10 μL, 0.05 mmol) and 1-bromo-2-fluoro-5-(methylsulfonyl)-3-nitrobenzene (100 mg, 0.3 mmol) were added. This mixture was stirred overnight at room temperature and was then quenched with MeOH (1 mL). The resulting mixture was partitioned between ethyl acetate and water, and the combined organic layers were washed with brine, dried over MgSO₄, filtered, and concentrated to yield crude material. The product was purified by FCC on silica gel eluting a hexane: ethyl acetate gradient to afford methyl 1-[2-bromo-4-(methylsulfonyl)-6-nitrophenoxy]cyclopropanecarboxylate as a glass (45 mg, 30%). LCMS calculated for $C_{12}H_{13}BrNO_7S$ (M+H)⁺: m/z=394.1, 396.1; found 393.7, 395.8.

Step 3. 8-bromo-6-(methylsulfonyl)spiro[1,4-benzoxazine-2,1'-cyclopropan]-3(4H)-one

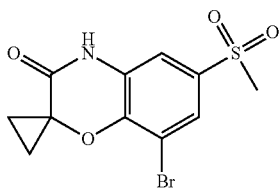 [SMILES: CS(=O)(=O)c1cc(Br)c2c(c1)NC(=O)C1(CC1)O2]

Iron filings (20 mg, 0.4 mmol) were added to a solution of methyl 1-[2-bromo-4-(methylsulfonyl)-6-nitrophenoxy]cyclopropanecarboxylate (40 mg, 0.1 mmol) in acetic acid (3 mL). The reaction was heated at 60° C. for 3 h, diluted with ethyl acetate, filtered, and concentrated. The residue was then dissolved in ethyl acetate and washed with saturated NaHCO$_3$. The organic layer was washed with brine, dried over MgSO$_4$, filtered, and concentrated to afford 8-bromo-6-(methylsulfonyl)spiro[1,4-benzoxazine-2,1'-cyclopropan]-3(4H)-one as crude material. LCMS calculated for C$_{11}$H$_{11}$BrNO$_4$S (M+H)$^+$: m/z=332.0, 334.0; found 331.8, 333.8.

Step 4. 8-(6-methyl-7-oxo-6,7-dihydro-1H-pyrrolo[2,3-c]pyridin-4-yl)-6-(methylsulfonyl)spiro[1,4-benzoxazine-2,1'-cyclopropan]-3(4H)-one Using methods similar to conditions in Example 44, but using 8-bromo-6-(methylsulfonyl)spiro[1,4-benzoxazine-2,1'-cyclopropan]-3(4H)-one from Step 3, the crude product was prepared. The product was purified by prep HPLC on a C-18 column eluting a water:acetonitrile gradient buffered at pH 10 to afford the title compound as an off white amorphous solid (10 mg, 30%). LCMS calculated for C$_{19}$H$_{18}$N$_3$O$_5$S (M+H)$^+$: m/z=400.1; found=400.0.

Example 58. 3,3-dimethyl-5-(6-methyl-7-oxo-6,7-dihydro-1H-pyrrolo[2,3-c]pyridin-4-yl)-7-(methylsulfonyl)-3,4-dihydroquinoxalin-2(1H)-one

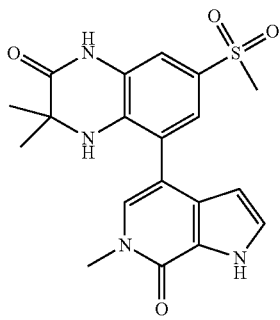 [SMILES: Cn1cc(-c2cc(S(C)(=O)=O)cc3c2NC(C)(C)C(=O)N3)c2cc[nH]c2c1=O]

Step 1. methyl 2-{[2-bromo-4-(methylsulfonyl)-6-nitrophenyl]amino}-2-methylpropanoate

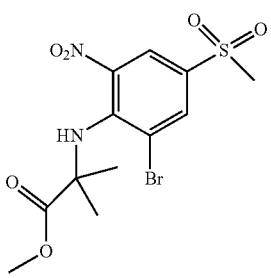 [SMILES: COC(=O)C(C)(C)Nc1c(Br)cc(S(C)(=O)=O)cc1[N+](=O)[O-]]

A mixture of 1-bromo-2-fluoro-5-(methylsulfonyl)-3-nitrobenzene (70 mg, 0.2 mmol) from Example 57, methyl 2-amino-2-methylpropanoate hydrochloride (50 mg, 0.3 mmol) (Sigma Aldrich cat# A8754), and sodium bicarbonate (40 mg, 0.5 mmol) in N-methylpyrrolidinone (4 mL) was heated overnight at 100° C. The mixture was then cooled to room temperature and partitioned between ethyl acetate and water. The combined organic layers were washed with brine, dried over MgSO$_4$, filtered, and concentrated to yield crude material. The product was purified by FCC on silica gel eluting a hexane: ethyl acetate gradient to afford methyl 2-{[2-bromo-4-(methylsulfonyl)-6-nitrophenyl]amino}-2-methylpropanoate as a glass (60 mg, 60%). LCMS calculated for C$_{12}$H$_{16}$BrN$_2$O$_6$S (M+H)$^+$: m/z=395.1, 397.1; found=395.0, 397.0.

Step 2. 3,3-dimethyl-5-(6-methyl-7-oxo-6,7-dihydro-1H-pyrrolo[2,3-c]pyridin-4-yl)-7-(methylsulfonyl)-3,4-dihydroquinoxalin-2(1H)-one Using methods similar to conditions in Example 57, but using methyl 2-{[2-bromo-4-(methylsulfonyl)-6-nitrophenyl]amino}-2-methylpropanoate from Step 1, the crude product was prepared. The product was purified by prep HPLC on a C-18 column eluting a water: acetonitrile gradient buffered at pH 10 to afford the title compound as an off white amorphous solid (12 mg, 30%). LCMS calculated for C$_{19}$H$_{21}$N$_4$O$_4$S (M+H)$^+$: m/z=401.1; found=401.1. $^1$H NMR (500 MHz, DMSO-d$_6$) δ 12.09 (s, 1H), 10.58 (s, 1H), 7.31-7.24 (m, 3H), 7.21 (s, 1H), 6.02 (s, 1H), 5.68 (s, 1H), 3.55 (s, 3H), 3.11 (s, 3H), 1.24 (s, 6H).

Examples 59-62

The compounds of Examples 59-62 and the experimental procedures used to prepare them are set out in Table 9 below.

TABLE 9

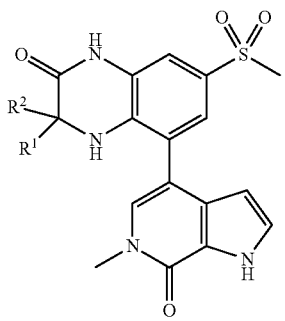

| Ex. No. | Name | R¹ | R² | Synthetic Procedure |
|---|---|---|---|---|
| 59 | 8'-(6-methyl-7-oxo-6,7-dihydro-1H-pyrrolo[2,3-c]pyridin-4-yl)-6'-(methylsulfonyl)-1',4'-dihydro-3'H-spiro[cyclopentane-1,2'-quinoxalin]-3'-one | 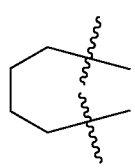<br>R¹ and R² taken together | | Ex. No. 58 |
| 60 | (3S)-3-isopropyl-5-(6-methyl-7-oxo-6,7-dihydro-1H-pyrrolo[2,3-c]pyridin-4-yl)-7-(methylsulfonyl)-3,4-dihydroquinoxalin-2(1H)-one | 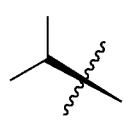 | H | Ex. No. 58 |
| 61 | (3R)-3-isopropyl-5-(6-methyl-7-oxo-6,7-dihydro-1H-pyrrolo[2,3-c]pyridin-4-yl)-7-(methylsulfonyl)-3,4-dihydroquinoxalin-2(1H)-one | 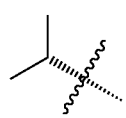 | H | Ex. No. 58 |
| 62 | 8'-(6-methyl-7-oxo-6,7-dihydro-1H-pyrrolo[2,3-c]pyridin-4-yl)-6'-(methylsulfonyl)-1',4'-dihydro-3'H-spiro[cyclobutane-1,2'-quinoxalin]-3'-one | 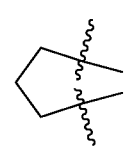<br>R¹ and R² taken together | | Ex. No. 58 |

Example 63. 4-methyl-8-(6-methyl-7-oxo-6,7-dihydro-1H-pyrrolo[2,3-c]pyridin-4-yl)-6-(methylsulfonyl)spiro[1,4-benzoxazine-2,1'-cyclopropan]-3(4H)-one

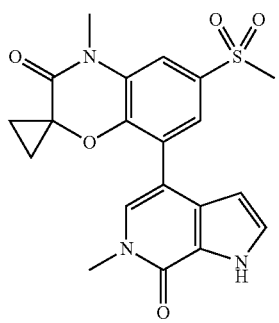 [SMILES: CN1C(=O)C2(CC2)Oc2c(-c3cn(C)c(=O)c4[nH]ccc34)cc(S(C)(=O)=O)cc21]

Step 1.
1-bromo-2-fluoro-5-(methylsulfonyl)-3-nitrobenzene

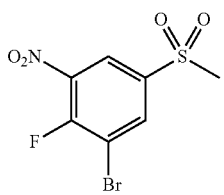

Nitric acid (0.42 mL, 10. mmol) was added drop wise to a solution of 1-fluoro-4-(methylsulfonyl)-2-nitrobenzene (2 g, 9 mmol) in sulfuric acid (10 mL) and bromine (1 g, 9 mmol) and the reaction was heated to 80° C. for 5 hrs. The reaction was allowed to cool to rt and was poured into ice. The aqueous layer was extracted with methylene chloride. The combined organic layer was washed with saturated $Na_2S_2O_3$, brine, dried over $MgSO_4$, filtered and concentrated to give the crude material. The product was purified by FCC on silica gel eluting with a hexane: ethyl acetate gradient to obtain 1-bromo-2-fluoro-5-(methylsulfonyl)-3-nitrobenzene as a white solid (0.80 g, 30%).

Step 2. Methyl 1-[2-bromo-4-(methylsulfonyl)-6-nitrophenoxy]cyclopropanecarboxylate

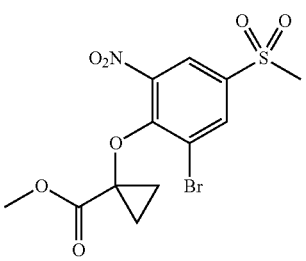

Sodium hydride in mineral oil (110 mg, 4.7 mmol) was added to a solution of methyl 1-hydroxycyclopropanecarboxylate (100 mg, 0.8 mmol) in N,N-dimethylformamide (20 mL) at 0° C. After 5 min, 1-bromo-2-fluoro-5-(methylsulfonyl)-3-nitrobenzene (250 mg, 0.84 mmol) was added and the reaction was stirred at 0° C. for 1 h. The reaction was quenched with MeOH (3 mL) and partitioned between water and ethyl acetate. The combined organic layer was washed with brine, dried over MgSO$_4$, filtered and concentrated to give crude material. The product was purified by FCC on silica gel eluting with hexane:ethyl acetate gradient to give methyl 1-[2-bromo-4-(methylsulfonyl)-6-nitrophenoxy]cyclopropanecarboxylate as a yellow oil (0.10 g, 67%). LCMS calculated for $C_{12}H_{13}BrNO_7S$ (M+H)$^+$: m/z=394.0 396.0; found: 394.0, 395.9.

Step 3. 8-bromo-6-(methylsulfonyl)spiro[1,4-benzoxazine-2,1'-cyclopropan]-3(4H)-one

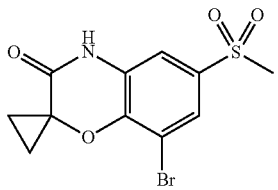 [SMILES: CS(=O)(=O)c1cc(Br)c2c(c1)NC(=O)C1(CC1)O2]

Iron powder (500 mg, 8 mmol) was added to a solution of methyl 1-[2-bromo-4-(methylsulfonyl)-6-nitrophenoxy]cyclopropanecarboxylate (700 mg, 2 mmol) in acetic acid (40 mL) which was degassed with nitrogen. The reaction was heated at 60° C. for 3 hrs. The reaction was allowed to cool to rt, diluted with ethyl acetate, filtered and concentrated. The residue was portioned between ethyl acetate and saturated NaHCO$_3$. The combined organic layer was washed with brine, dried over MgSO$_4$, filtered and concentrated to give crude material as a solid (0.50 g, 90%). LCMS calculated for $C_{11}H_{11}BrNO_4S$ (M+H)$^+$: m/z=331.9, 333.9; found: 331.9, 333.8.

Step 4. 8-Bromo-4-methyl-6-(methylsulfonyl)spiro[1,4-benzoxazine-2,1'-cyclopropan]-3(4H)-one

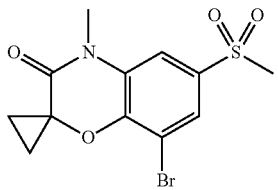 [SMILES: CN1C(=O)C2(CC2)Oc2c(Br)cc(S(C)(=O)=O)cc21]

Sodium hydride in mineral oil (30. mg, 1.3 mmol) was added to a mixture of 8-bromo-6-(methylsulfonyl)spiro[1,4-benzoxazine-2,1'-cyclopropan]-3(4H)-one (280 mg, 0.84 mmol) in N,N-dimethylformamide (50 mL) at 0° C. The reaction was stirred for 20 min and methyl iodide (63 μL, 1.0 mmol) was added and stirred for 30 min at rt. The reaction was quenched with methanol and partitioned between ethyl acetate and water. The combined organic layer was washed with brine, dried over MgSO$_4$, filtered and concentrated to give crude material. The product was purified by FCC on silica gel eluting with hexane:ethyl acetate gradient to give 8-bromo-4-methyl-6-(methylsulfonyl)spiro[1,4-benzoxazine-2,1'-cyclopropan]-3(4H)-one as a semisolid (0.286 g, 96%). LCMS calculated for $C_{12}H_{13}BrNO_4S$ (M+H)$^+$: m/z=346.1 and 348.1; found: 346.1, 348.1.

Step 5. 4-methyl-8-{6-methyl-1-[(4-methylphenyl)sulfonyl]-7-oxo-6,7-dihydro-1H-pyrrolo[2,3-c]pyridin-4-yl}-6-(methylsulfonyl)spiro[1,4-benzoxazine-2,1'-cyclopropan]-3(4H)-one

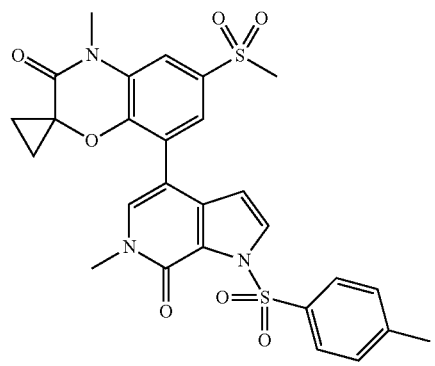 [SMILES: Cc1ccc(S(=O)(=O)n2ccc3c(-c4cc(S(C)(=O)=O)cc5c4OC4(CC4)C(=O)N5C)cn(C)c(=O)c32)cc1]

8-Bromo-4-methyl-6-(methylsulfonyl)spiro[1,4-benzoxazine-2,1'-cyclopropan]-3(4H)-one (260 mg, 0.75 mmol) and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (390 mg, 0.90 mmol) were dissolved in 1,4-dioxane (40 mL) with cesium fluoride (300 mg, 2 mmol) in water (10 mL) and the reaction was degassed with nitrogen. The catalyst 4-(di-tert-butylphosphino)-N,N-dimethylaniline-dichloropalladium (2:1) (200 mg, 0.2 mmol) was added, degassed with nitrogen and the reaction was heated to 100° C. for 2 hrs. The reaction was allowed to cool to rt and partitioned between ethyl acetate and water. The combined organic layer was washed with brine and dried over MgSO$_4$, filtered and concentrated to give crude material. The product was purified by FCC on silica gel eluting hexane:ethyl acetate gradient to give 4-methyl-8-{6-methyl-1-[(4-methylphenyl)sulfonyl]-7-oxo-6,7-dihydro-1H-pyrrolo[2,3-c]pyridin-4-yl}-6-(methylsulfonyl)spiro[1,4-benzoxazine-2,1'-cyclopropan]-3(4H)-one as a solid residue (0.27 g, 63%). LCMS calculated for $C_{27}H_{26}N_3O_7S_2$ (M+H)$^+$: m/z=568.1; found: 568.1.

Step 6. 4-methyl-8-(6-methyl-7-oxo-6,7-dihydro-1H-pyrrolo[2,3-c]pyridin-4-yl)-6-(methylsulfonyl)spiro[1,4-benzoxazine-2,1'-cyclopropan]-3(4H)-one 1.0 M Sodium hydroxide in water (2 mL, 2 mmol) was added to a solution of 4-methyl-8-{6-methyl-1-[(4-methylphenyl)sulfonyl]-7-oxo-6,7-dihydro-1H-pyrrolo[2,3-c]pyridin-4-yl}-6-(methylsulfonyl)spiro[1,4-benzoxazine-2,1'-cyclopropan]-3(4H)-one in ethanol (6 mL). The reaction was stirred at 80° C. for 2 h, then allowed to cool to rt. The product was purified without workup by prep HPLC on a C-19 column eluting with a water:acetonitrile gradient buffered pH 10 to give the title compound as a white amorphous solid (0.12 g, 39%). $^1$H NMR (500 MHz, DMSO-d$_6$) δ 12.09 (s, 1H), 7.62 (d, J=2.1 Hz, 1H), 7.60 (d, J=2.1 Hz, 1H), 7.30 (d, J=2.8 Hz, 1H), 7.25 (s, 1H), 6.14 (d, J=2.8 Hz, 1H), 3.54 (s, 3H), 3.42 (s, 3H), 3.29 (s, 3H), 1.32-1.25 (m, 2H), 1.16-1.10 (m, 2H). LCMS calculated for $C_{20}H_{20}N_3O_5S$ (M+H)$^+$: m/z=414.1; found: 414.1.

Example 64. 8'-(6-methyl-7-oxo-6,7-dihydro-1H-pyrrolo[2,3-c]pyridin-4-yl)-6'-(methylsulfonyl)-1',4'-dihydro-3'H-spiro[cyclohexane-1,2'-quinoxalin]-3'-one

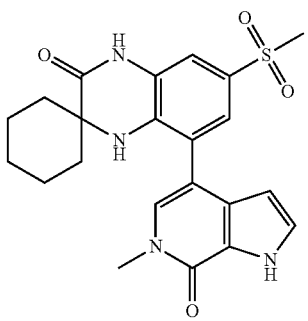 [SMILES: Cn1cc(-c2cc(S(C)(=O)=O)cc3c2NC2(CCCCC2)C(=O)N3)c2cc[nH]c2c1=O]

The compound of Example 64 was synthesized according to an experimental procedure analogous to that used for the synthesis of the compound of Example 58 to afford the title compound as a white amorphous solid (5 mg, 10%). LCMS found (M+H)$^+$=441.2.

Examples 65-66

The compounds of Examples 65-66 and the experimental procedures used to prepare them are set out in Table 10 below.

TABLE 10

| Ex. No. | Name | $R^1$ | $R^2$ | $R^3$ | Synthetic Procedure |
|---|---|---|---|---|---|
| 65 | 8-(6-methyl-7-oxo-6,7-dihydro-1H-pyrazolo[3,4-c]pyridin-4-yl)-6-(methylsulfonyl)spiro[1,4-benzoxazine-2,1'-cyclopropan]-3(4H)-one | $R^1$ and $R^2$ taken together | | H | Ex. Nos. 57, 26 |
| 66 | 4-methyl-8-(6-methyl-7-oxo-6,7-dihydro-1H-pyrazolo[3,4-c]pyridin-4-yl)-6-(methylsulfonyl)spiro[1,4-benzoxazine-2,1'-cyclopropan]-3(4H)-one | $R^1$ and $R^2$ taken together | | CH$_3$— | Ex. Nos. 57, 26, 8 |

Example 67. 2-isopropyl-N,N-dimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide

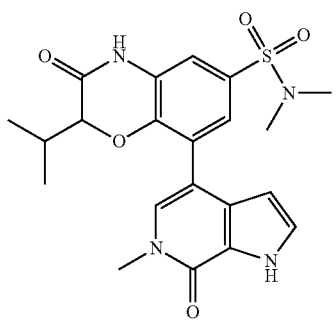 [SMILES: CC(C)C1Oc2c(cc(S(=O)(=O)N(C)C)cc2-c2cn(C)c(=O)c3[nH]ccc23)NC1=O]

Step 1.
4-hydroxy-N,N-dimethyl-3-nitrobenzenesulfonamide

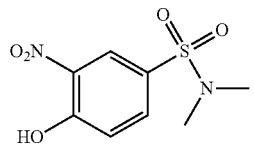 [SMILES: CN(C)S(=O)(=O)c1ccc(O)c([N+](=O)[O-])c1]

2.0 M Dimethylamine in THF (0.2 mL, 0.4 mmol) was added to a mixture of 4-hydroxy-3-nitrobenzenesulfonyl chloride (100 mg, 0.4 mmol) (Matrix cat#084425) and 4-N,N-dimethylaminopyridine (50 mg, 0.4 mmol) in tetrahydrofuran (5 mL) at room temperature. The reaction mixture was stirred overnight then partitioned between ethyl acetate and 1 N HCl. The combined organic layers were washed with brine, dried over MgSO$_4$, filtered, and concentrated to afford crude 4-hydroxy-N,N-dimethyl-3-nitrobenzenesulfonamide as a solid (90 mg, 90%). LCMS calculated for C$_8$H$_{11}$N$_2$O$_5$S (M+H)$^+$: m/z=247.1; found=247.0.

Step 2. 3-bromo-4-hydroxy-N,N-dimethyl-5-nitrobenzenesulfonamide

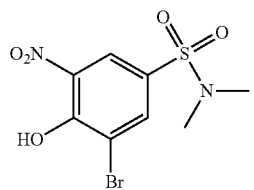

Bromine (10 µL, 0.2 mmol) was added to a solution of 4-hydroxy-N,N-dimethyl-3-nitrobenzenesulfonamide (50 mg, 0.2 mmol) in acetic acid (2 mL) and ferric chloride (7 mg, 0.04 mmol) in water (0.5 mL) at room temperature. The reaction was stirred overnight at room temperature then partitioned between saturated NaHCO$_3$ and ethyl acetate. The combined organic layers were washed with brine, dried over MgSO$_4$, filtered, and concentrated to afford crude 3-bromo-4-hydroxy-N,N-dimethyl-5-nitrobenzenesulfonamide (60 mg, 80%) as a glass. LCMS calculated for C$_8$H$_{10}$BrN$_2$O$_5$S (M+H)$^+$: m/z=325.1, 327.1; found=324.9, 326.9.

Step 3. 3-amino-5-bromo-4-hydroxy-N,N-dimethyl-benzenesulfonamide

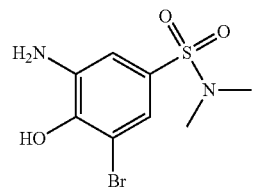 [SMILES: CN(C)S(=O)(=O)c1cc(Br)c(O)c([N+](=O)[O-])c1]

Raney Nickel (25 mg) was added to a solution of 3-bromo-4-hydroxy-N,N-dimethyl-5-nitrobenzenesulfonamide (50 mg, 0.2 mmol) in ethanol (5 mL) in a Parr shaker bottle. The mixture was degassed with nitrogen and charged to 30 psi hydrogen. The mixture was shaken for 2 h, filtered, and concentrated to afford crude 3-amino-5-bromo-4-hydroxy-N,N-dimethylbenzenesulfonamide as a yellow oil (40 mg, 90%). LCMS calculated for C$_8$H$_{12}$BrN$_2$O$_3$S (M+H)$^+$: m/z=295.1, 297.1; found=295.0, 297.0.

Step 4. 2-isopropyl-N,N-dimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide Using methods similar to conditions in Example 9, but using 3-amino-5-bromo-4-hydroxy-N,N-dimethylbenzenesulfonamide from Step 3, the crude product was prepared. The product was purified by prep HPLC on a C-18 column eluting a water:acetonitrile gradient buffered at pH 10 to afford the title compound as a white amorphous solid (4 mg, 40%). LCMS calculated for C$_{21}$H$_{25}$N$_4$O$_5$S (M+H)$^+$: m/z=445.1; found=445.2. $^1$H NMR (300 MHz, DMSO-d$_6$) δ 12.1 (s, 1H), 7.35 (s, 1H), 7.29 (d, J=2.8 Hz, 1H), 7.22 (m, 1H), 7.11 (m, 1H), 6.16 (d, J 2.7 Hz, 1H), 4.4 (d, 1H), 3.54 (s, 3H), 2.62 (s, 3H), 2.48 (s, 3H), 2.3-2.2 (m, 1H), 0.80 (dd, 6H).

Example 75. 2,2,4-trimethyl-8-(6-methyl-7-oxo-6,7-dihydro-1H-pyrrolo[2,3-c]pyridin-4-yl)-6-(methylsulfonyl)-2H-1,4-benzoxazin-3(4H)-one

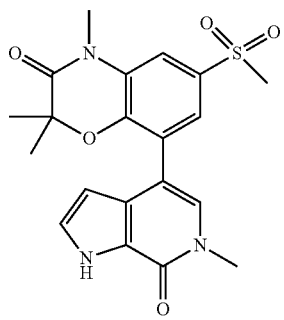 [SMILES: CN1C(=O)C(C)(C)Oc2c(-c3cn(C)c(=O)c4[nH]ccc34)cc(S(C)(=O)=O)cc21]

Step 1. 4-(methylthio)phenol

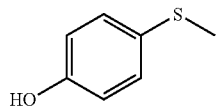

4-Mercaptophenol (0.5 g, 4 mmol) (Aldrich cat#559938-5) was dissolved in acetone (10.0 mL), then potassium carbonate (0.684 g, 4.95 mmol) and iodomethane (0.396 mL, 4.95 mmol) were added. The reaction mixture was stirred at room temperature for 2 h, diluted with ethyl acetate, and filtered. The organic layer was concentrated in vacuo to yield a yellow oil. The product was purified by FCC on silica gel eluting a hexane: ethyl acetate gradient to afford 4-(methylthio)phenol as a clear oil which crystallized upon sitting (0.55 g, 80%).

Step 2. 4-(methylsulfonyl)phenol

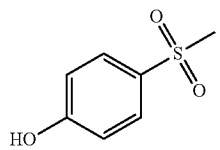

Oxone (0.99 g, 6.5 mmol) (Aldrich cat#22803-6) was added in portions to a solution of 4-(methylthio)phenol (0.50 g, 3.2 mmol) in ethanol (10.0 mL) and water (10.0 mL) at room temperature. The reaction mixture was stirred for 18 h then partitioned between ethyl acetate and water. The combined organic layers were washed with brine, dried over magnesium sulfate, and concentrated in vacuo to afford 4-(methylsulfonyl)phenol as a semisolid (0.60 g, 96%). LCMS calculated for $C_7H_9O_3S$ $(M+H)^+$: m/z=173.0; found: 173.0.

Step 3. 4-(methylsulfonyl)-2-nitrophenol

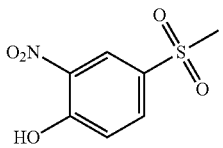

Nitric acid (0.1 mL, 3 mmol) was added to a mixture of 4-(methylsulfonyl)phenol (0.5 g, 3 mmol) in acetic acid (9 mL) at room temperature. The mixture was heated to 80° C. for 3 h then cooled to room temperature and partitioned between ethyl acetate and water. The combined organic layers were washed with brine, dried over MgSO$_4$, filtered, and concentrated to yield crude product. The product was crystallized from ethyl ether to afford 4-(methylsulfonyl)-2-nitrophenol as a pale yellow solid (0.59 g, 100%). LCMS calculated for $C_7H_8NO_5S$ $(M+H)^+$: m/z=218.1; found: 218.0.

Step 4. 2-bromo-4-(methylsulfonyl)-6-nitrophenol

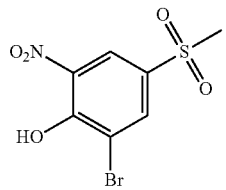

Bromine (0.41 g, 2.6 mmol) in acetic acid (5 mL) was added to a solution of 4-(methylsulfonyl)-2-nitrophenol (0.63 g, 2 mmol) in acetic acid (20 mL) and ferric chloride (0.08 g, 0.5 mmol) in water (0.3 mL) at room temperature and the resulting mixture was stirred for 4 h. This mixture was then diluted with water (70 mL), forming a slurry. The solids were collected, washed with water, and dried to afford 2-bromo-4-(methylsulfonyl)-6-nitrophenol as an off white powder (0.75 gm, 80%). LCMS calculated for $C_7H_7BrNO_5S$ $(M+H)^+$: m/z=295.9, 297.9; found: 296.0, 298.0.

Step 5. 2-amino-6-bromo-4-(methylsulfonyl)phenol

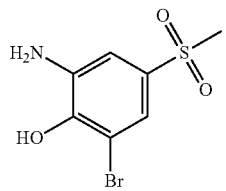

2-Bromo-4-(methylsulfonyl)-6-nitrophenol (0.20 g, 0.64 mmol) was dissolved in ethanol (7.0 mL, 120 mmol), degassed with nitrogen, and then Raney Nickel (75 mg) was added. The reaction mixture was stirred under a hydrogen atmosphere for 2 h. The mixture was decanted from the solids and concentrated in vacuo to afford 2-amino-6-bromo-4-(methylsulfonyl)phenol as a glass (0.19 g, 95%). LCMS calculated for $C_7H_9BrNO_3S$ $(M+H)^+$: m/z=266.1, 268.1; found: 266.0, 268.0.

Step 6. 8-bromo-2, 2-dimethyl-6-(methylsulfonyl)-2H-1,4-benzoxazin-3(4H)-one

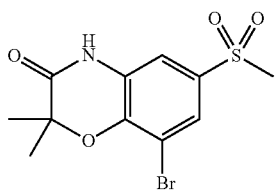

2-Bromo-2-methyl-propanoyl bromide (0.41 mL, 3.4 mmol) (Aldrich cat#252271) was added slowly to a solution of 2-amino-6-bromo-4-(methylsulfonyl)phenol (0.75 g, 2.8 mmol) in acetonitrile (49.7 mL) and potassium carbonate (1.6 g, 11 mmol) in water (16 mL) at rt. The reaction was stirred for 1 h and was heated to 80° C. in an oil bath to cyclize. The reaction was heated for 18 h and was allowed to cool to rt. The reaction was partitioned between ethyl acetate and water. The combined organic layer was washed with brine, dried over magnesium sulfate and concentrated to give a dark oil. The product was purified by FCC on silica gel eluting hexane:ethyl acetate gradient to give 8-bromo-2,2-dimethyl-6-(methyl sulfonyl)-2H-1,4-benzoxazin-3(4H)-one as a solid (0.84 g, 89%). LCMS calculated for $C_{11}H_{13}BrNO_4S$ (M+H)$^+$: m/z=334.1, 336.1; found: 334.0, 336.0.

Step 7. 8-bromo-2, 2, 4-trimethyl-6-(methylsulfonyl)-2H-1,4-benzoxazin-3(4H)-one

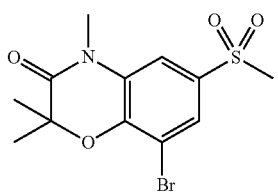 [SMILES: CN1C(=O)C(C)(C)Oc2c(Br)cc(S(C)(=O)=O)cc21]

Sodium hydride (0.12 g, 2.9 mmol) was added to a solution of 8-bromo-2,2-dimethyl-6-(methylsulfonyl)-2H-1,4-benzoxazin-3(4H)-one (0.82 g, 2.4 mmol) in N,N-dimethylformamide (23.4 mL) under nitrogen at rt. The reaction was stirred for 30 minutes and methyl iodide (0.30 mL, 4.9 mmol) was added. After stirring for 1 h the reaction was partitioned between ethyl acetate and water. The organic layer was washed with brine, dried over magnesium sulfate and concentrated to give 8-bromo-2, 2,4-trimethyl-6-(methylsulfonyl)-2H-1,4-benzoxazin-3(4H)-one as a solid residue (0.83 g, 97%). LCMS calculated for $C_{12}H_{15}BrNO_4S$ (M+H)$^+$: m/z=348.1, 350.1; found: 348.0, 350.0.

Step 8. 2,2, 4-trimethyl-8-(6-methyl-7-oxo-6,7-dihydro-1H-pyrrolo[2,3-c]pyridin-4-yl)-6-(methylsulfonyl)-2H-1,4-benzoxazin-3(4H)-one Using methods similar to conditions in Example 9, but using 8-bromo-2,2,4-trimethyl-6-(methylsulfonyl)-2H-1,4-benzoxazin-3(4H)-one from Step 7, the crude product was prepared. The product was purified by prep HPLC on a C-18 column eluting with a water:acetonitrile gradient buffered at pH 10 to afford the title compound as an off white amorphous solid (25 mg, 30%). LCMS calculated for $C_{20}H_{22}N_3O_5S$ (M+H)$^+$: m/z=416.1; found 416.1. $^1$H NMR (300 MHz, DMSO-d6) δ 12.11 (s, 1H), 7.63 (d, J=1.7 Hz, 1H), 7.59 (d, J=1.9 Hz, 1H), 7.30 (d, J=2.7 Hz, 2H), 6.15 (d, J=2.1 Hz, 1H), 3.56 (s, 3H), 3.40 (s, 3H), 3.28 (s, 3H), 1.38 (s, 6H).

Example 76. 6-(ethylsulfonyl)-2,2,4-trimethyl-8-(6-methyl-7-oxo-6,7-dihydro-1H-pyrrolo[2,3-c]pyridin-4-yl)-2H-1,4-benzoxazin-3(4H)-one

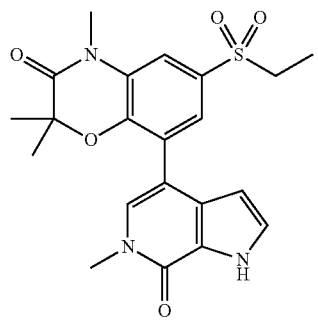 [SMILES: CCS(=O)(=O)c1cc(-c2cn(C)c(=O)c3[nH]ccc23)c2c(c1)N(C)C(=O)C(C)(C)O2]

Step 1. 8-bromo-6-(ethylsulfonyl)-2,2-dimethyl-2H-1,4-benzoxazin-3(4H)-one

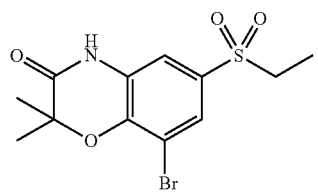 [SMILES: CCS(=O)(=O)c1cc(Br)c2c(c1)NC(=O)C(C)(C)O2]

Potassium carbonate (200 mg, 1 mmol) was added to a solution of 2-amino-6-bromo-4-(ethylsulfonyl)phenol (180 mg, 0.64 mmol) from Example 51, Step 5, in acetonitrile (2 mL) and 2-bromo-2-methyl-propanoic acid ethyl ester (520 mg, 2.7 mmol). The reaction was heated to 80° C. for 3 hrs. The reaction was filtered, concentrated and purified by FCC on silica gel eluting with a hexane:ethyl acetate gradient to afford 8-bromo-6-(ethylsulfonyl)-2,2-dimethyl-2H-1,4-benzoxazin-3(4H)-one as white solid (124 mg, 54%). LCMS calculated for $C_{12}H_{15}BrNO_4S$ (M+H)$^+$: m/z=348.1, 350.1; found: 347.8, 349.9.

Step 2. 8-bromo-6-(ethylsulfonyl)-2, 2, 4-trimethyl-2H-1,4-benzoxazin-3(4H)-one

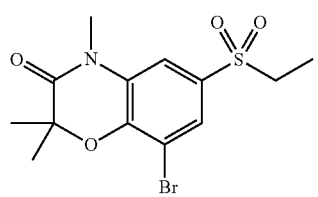 [SMILES: CCS(=O)(=O)c1cc(Br)c2c(c1)N(C)C(=O)C(C)(C)O2]

Sodium hydride in mineral oil (19 mg, 0.78 mmol) was added to a mixture of 8-bromo-6-(ethylsulfonyl)-2,2-dimethyl-2H-1,4-benzoxazin-3(4H)-one (180 mg, 0.52 mmol) in N,N-dimethylformamide (30 mL) at 0° C. The reaction was stirred for 20 min and methyl iodide (39 μL, 0.62 mmol) was added and stirred for 30 min at rt. The reaction was quenched with MeOH and partitioned between water and ethyl acetate. The combined organic layer was washed with brine, dried over MgSO₄, filtered and concentrated to give crude 8-bromo-6-(ethylsulfonyl)-2,2,4-trimethyl-2H-1,4-benzoxazin-3(4H)-one as a foam (280 mg, 96%). LCMS calculated for $C_{13}H_{17}BrNO_4S$ (M+H)⁺: m/z=362.0, 364.0; found: 362.0, 364.0.

Step 3. 6-(ethylsulfonyl)-2, 2, 4-trimethyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one

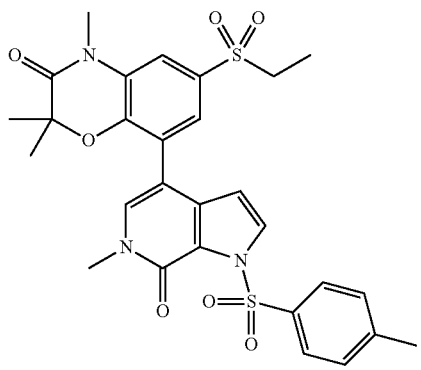

8-Bromo-6-(ethylsulfonyl)-2,2,4-trimethyl-2H-1,4-benzoxazin-3(4H)-one (200 mg, 0.6 mmol) and 6-methyl-1-[(4-methyphenyl)sulfonyl]-4-(4,4,5,5-tetramethyl-1,3,2-dioxaborolan-2-yl)-1,6-dihydro-7H-pyrrolo[2,3-c]pyridin-7-one (280 mg, 0.66 mmol) were dissolved in 1,4-dioxane (30 mL) with cesium fluoride (200 mg, 2 mmol) in water (10 mL) and was degassed with nitrogen. The catalyst 4-(di-tert-butyl-phosphino)-N,N-dimethylaniline-dichloropalladium (2:1) (100 mg, 0.2 mmol) was added, degassed with N₂ and the reaction was heated to 100° C. for 2 h. The reaction was allowed to cool to rt, diluted with ethyl acetate and washed with water, brine and dried over MgSO₄, then filtered and concentrated to give crude material. The product was purified by FCC on silica gel eluting with hexane:ethyl acetate gradient to obtain 6-(ethylsulfonyl)-2,2,4-trimethyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one as a glass (200 mg, 60%). LCMS calculated for $C_{28}H_{30}N_3O_7S_2$(M+H)⁺: m/z=584.1; found: 584.2.

Step 4. 6-(ethylsulfonyl)-2, 2, 4-trimethyl-8-(6-methyl-7-oxo-6,7-dihydro-1H-pyrrolo[2,3-c]pyridin-4-yl)-2H-1,4-benzoxazin-3(4H)-one 1.0 M Sodium hydroxide in water (1 mL, 1 mmol) was added to a solution obtain 6-(ethylsulfonyl)-2,2,4-trimethyl-8-{6-methyl-1-[(4-methylphenyl)sulfonyl]-7-oxo-6,7-dihydro-1H-pyrrolo[2,3-c]pyridin-4-yl}-2H-1,4-benzoxazin-3(4H)-one in ethanol (4 mL). The reaction was stirred at 80° C. for 2 h, allowed to cool to rt and purified by prep HPLC without workup on a C-18 column eluting with a water:acetonitrile gradient buffered pH 10 to give the title compound as a white amorphous solid (110 mg, 50%). ¹H NMR (300 MHz, DMSO-d₆) δ 12.12 (s, 1H), 7.58 (d, J=1.9 Hz, 1H), 7.52 (d, J=2.0 Hz, 1H), 7.30 (d, J=2.6 Hz, 2H), 6.13 (d, J 2.1 Hz, 1H), 3.56 (s, 3H), 3.39 (s, 3H), 3.34 (q, J=7.4 Hz, 2H), 1.38 (s, 6H), 1.14 (t, J=7.3 Hz, 3H). LCMS calculated for $C_{21}H_{24}N_3O_5S$ (M+H)⁺: m/z=430.1; found: 430.1.

Examples 68-83

The compounds of Examples 68-83 and the experimental procedures used to prepare them are set out in Table 11 below.

TABLE 11

| Ex. No. | Name | R¹ | R² | R³ | R⁵ | Synthetic Procedure |
|---|---|---|---|---|---|---|
| 68 | 2-isopropyl-N-methyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide | i-Prop | H | H | ⟶S(O)₂NHCH₃ | Ex. No. 67 |
| 69 | N,N,2,2,4-pentamethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide | CH₃— | CH₃— | CH₃— | ⟶S(O)₂N(CH₃)₂ | Ex. Nos. 67, 8 |

TABLE 11-continued

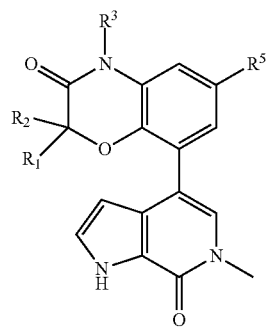

| Ex. No. | Name | R¹ | R² | R³ | R⁵ | Synthetic Procedure |
|---|---|---|---|---|---|---|
| 70 | N,N,2,2-tetramethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide | CH₃— | CH₃— | H | —S(O)₂N(CH₃)₂ | Ex. No. 67 |
| 71 | 2-isopropyl-N,N,4-trimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide | i-Prop | H | CH₃— | —S(O)₂N(CH₃)₂ | Ex. Nos. 67, 8 |
| 72 | 2,2-dimethyl-8-(6-methyl-7-oxo-6,7-dihydro-1H-pyrrolo[2,3-c]pyridin-4-yl)-6-(piperidin-1-ylsulfonyl)-2H-1,4-benzoxazin-3(4H)-one | CH₃— | CH₃— | H | —S(O)₂-piperidinyl | Ex. No. 67 |
| 73 | 2,2,4-trimethyl-8-(6-methyl-7-oxo-6,7-dihydro-1H-pyrrolo[2,3-c]pyridin-4-yl)-6-(piperidin-1-ylsulfonyl)-2H-1,4-benzoxazin-3(4H)-one | CH₃— | CH₃— | CH₃— | —S(O)₂-piperidinyl | Ex. Nos. 67, 8 |
| 74 | N-isopropyl-2,2-dimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide | CH₃— | CH₃— | H | —S(O)₂NH(i-Pr) | Ex. No. 67 |
| 75 | 2,2,4-trimethyl-8-(6-methyl-7-oxo-6,7-dihydro-1H-pyrrolo[2,3-c]pyridin-4-yl)-6-(methylsulfonyl)-2H-1,4-benzoxazin-3(4H)-one | CH₃— | CH₃— | CH₃— | —S(O)₂CH₃ | Ex. No. 75 |
| 76 | 6-(ethylsulfonyl)-2,2,4-trimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | CH₃— | —S(O)₂Et | Ex. No. 76 |
| 77 | 6-(isopropylsulfonyl)-2,2,4-trimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | CH₃— | —S(O)₂(i-Pr) | Ex. Nos. 51, 8 |
| 78 | 6-(ethylsulfonyl)-2,2-dimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | H | —S(O)₂Et | Ex. No. 51 |

TABLE 11-continued

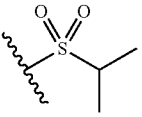 [SMILES: *S(=O)(=O)C(C)C]

| Ex. No. | Name | R¹ | R² | R³ | R⁵ | Synthetic Procedure |
|---|---|---|---|---|---|---|
| 79 | 6-(isopropylsulfonyl)-2,2-dimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | H | 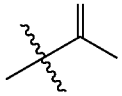 | Ex. No. 51 |
| 80 | 6-acetyl-2,2-dimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | H | 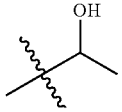 | Ex. No. 9 |
| 81 | 6-(1-hydroxyethyl)-2,2-dimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | H | 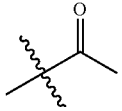 [SMILES: *C(C)=O] | Ex. Nos. 80, 50 |
| 82 | 6-acetyl-2,2,4-trimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | CH₃— | 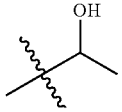 | Ex. Nos. 9, 8 |
| 83 | 6-(1-hydroxyethyl)-2,2,4-trimethyl-8-(6-methyl-7-oxo-6,7-dihydro-1H-pyrrolo[2,3-c]pyridin-4-yl)-2H-1,4-benzoxazin-3(4H)-one | CH₃— | CH₃— | CH₃— | 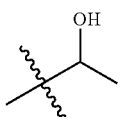 [SMILES: *C(C)O] | Ex. Nos. 82, 50 |

Example 83A. 6-(1-hydroxyethyl)-2,2,4-trimethyl-8-(6-methyl-7-oxo-6,7-dihydro-1H-pyrrolo[2,3-c]pyridin-4-yl)-2H-1,4-benzoxazin-3(4H)-one (Enantiomer 1)

Example 83B. 6-(1-hydroxyethyl)-2,2,4-trimethyl-8-(6-methyl-7-oxo-6,7-dihydro-1H-pyrrolo[2,3-c]pyridin-4-yl)-2H-1,4-benzoxazin-3(4H)-one (Enantiomer 2)

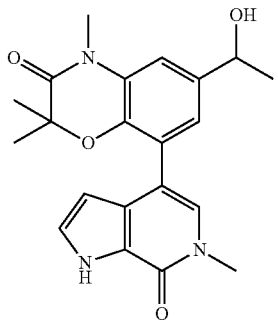 [SMILES: CC(O)c1cc(-c2cn(C)c(=O)c3[nH]ccc23)c2c(c1)N(C)C(=O)C(C)(C)O2]

The enantiomers of the compound of Example 83 were separated by prep chiral column chromatography using the following conditions: Column: phenomenex Lux Cellulose C-2, 5 μm, 21, 2×250 mm; Mobile phase: 60% EtOH/Hexanes, gradient condition: isocratic at 18 mL/min, Loading: 9.0 mg in 900 μL, run time: 11 min; peak retention times: 6.4 and 8.5 min.

Example 83A, Peak 1 (6.4 min) LCMS calculated for $C_{21}H_{24}N_3O_4$ $(M+H)^+$: m/z=382.1; found: 382.1. $^1H$ NMR (300 MHz, DMSO-$d_6$) δ 11.99 (s, 1H), 7.22 (t, J=2.7 Hz, 1H), 7.12 (s, 1H), 7.04 (s, 2H), 6.08 (t, J=2.3 Hz, 1H), 5.14 (d, J=4.3 Hz, 1H), 4.77-4.60 (m, 1H), 3.50 (s, 3H), 3.27 (s, 3H), 1.30 (d, J=6.4 Hz, 3H), 1.27 (s, 6H).

Example 83B, Peak 2 (8.5 min) LCMS calculated for $C_{21}H_{24}N_3O_4$ $(M+H)^+$: m/z=382.1; found: 382.1. $^1H$ NMR (300 MHz, DMSO-$d_6$) δ 11.99 (s, 1H), 7.22 (t, J=2.7 Hz, 1H), 7.12 (s, 1H), 7.04 (s, 2H), 6.08 (t, J=2.3 Hz, 1H), 5.14 (d, J=4.3 Hz, 1H), 4.77-4.60 (m, 1H), 3.50 (s, 3H), 3.27 (s, 3H), 1.30 (d, J=6.4 Hz, 3H), 1.27 (s, 6H).

Example 84. 2-isopropyl-8-(6-methyl-7-oxo-6,7-dihydro-1H-pyrazolo[3,4-c]pyridin-4-yl)-6-(methylsulfonyl)-2H-1,4-benzoxazin-3(4H)-one

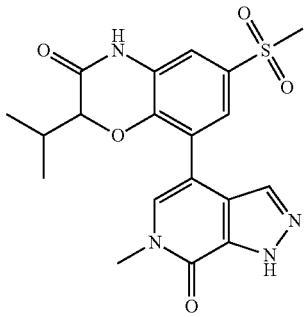 [SMILES: CC(C)C1Oc2c(cc(S(C)(=O)=O)cc2-c2cn(C)c(=O)c3[nH]ncc23)NC1=O]

The compound of Example 84 was synthesized according to an experimental procedure analogous to that used for the synthesis of the compounds of Examples 44 and 26 to afford the title compound as a white amorphous solid (12 mg, 20%). LCMS found $(M+H)^+$=417.1. $^1H$ NMR (300 MHz, DMSO-$d_6$) δ 11.06 (s, 1H), 7.86 (bs, 1H), 7.55 (d, J=2.0 Hz, 1H), 7.44 (bs, 1H), 7.41 (d, J=2.0 Hz, 1H), 4.71 (d, J=3.7 Hz, 1H), 3.58 (s, 3H), 3.22 (s, 3H), 2.33-2.17 (m, 1H), 0.78 (d, J=6.7 Hz, 3H), 0.72 (d, J=6.9 Hz, 3H).

Analytical Data $^1H$ NMR data (Varian Inova 500 spectrometer, a Mercury 400 spectrometer, or a Varian (or Mercury) 300 spectrometer) and LCMS mass spectral data (MS) for the compounds of Examples 2-4, 13-16, 23-24, 33-34, 40-41, 45-49, 52-56, 59-62, 65-66, and 68-83 are provided below in Table 12.

TABLE 12

| Ex. No. | MS [M + H]+ | $^1H$ NMR Spectra |
|---|---|---|
| 2 | 338.1 | $^1H$ NMR (300 MHz, DMSO-$d_6$) δ 12.01 (s, 1H), 10.69 (s, 1H), 7.26 (s, 2H), 7.08-6.92 (m, 2H), 6.91-6.81 (m, 1H), 6.17 (bs, 1H), 4.39 (d, J = 4.1 Hz, 1H), 3.53 (s, 3H), 2.21 (dd, J = 11.3, 6.4 Hz, 1H), 0.81 (dd, J = 7.7 Hz, 6H). |
| 3 | 310.0 | $^1H$ NMR (500 MHz, DMSO-$d_6$) δ 11.98 (s, 1H), 10.67 (s, 1H), 7.26 (s, 1H), 7.21 (s, 1H), 7.06-6.95 (m, 2H), 6.94-6.86 (m, 1H), 6.17 (s, 1H), 4.68 (q, J = 6.6 Hz, 1H), 3.54 (s, 3H), 1.31 (d, J = 6.7 Hz, 3H). |
| 4 | 324.1 | $^1H$ NMR (500 MHz, DMSO-$d_6$) δ 11.98 (s, 1H), 10.68 (s, 1H), 7.26 (t, J = 2.6 Hz, 1H), 7.23 (s, 1H), 7.06-6.96 (m, 2H), 6.90 (q, J = 4.7, 4.1 Hz, 1H), 6.20-6.11 (m, 1H), 4.50 (dd, J = 8.0, 4.2 Hz, 1H), 3.54 (s, 3H), 1.88-1.75 (m, 1H), 1.72-1.60 (m, 1H), 0.79 (t, J = 7.4 Hz, 3H). |
| 13 | 425.2 | $^1H$ NMR (300 MHz, DMSO-$d_6$) δ 12.03 (s, 1H), 7.62 (s, 1H), 7.37-7.13 (m, 3H), 6.65 (d, J = 2.7 Hz, 1H), 6.45 (d, J = 2.7 Hz, 1H), 6.26-6.12 (m, 1H), 4.61-4.37 (m, 2H), 4.35 (d, J = 5.0 Hz, 1H), 3.73 (s, 3H), 3.54 (s, 3H), 2.16 (dd, J = 12.0, 6.7 Hz, 1H), 0.81 (d, J = 6.9 Hz, 3H), 0.75 (d, J = 6.7 Hz, 3H). |
| 14 | 508.2 | $^1H$ NMR (300 MHz, DMSO-$d_6$) δ 12.04 (s, 1H), 7.28 (dd, J = 6.1, 3.3 Hz, 2H), 6.66 (d, J = 2.7 Hz, 1H), 6.52 (d, J = 2.7 Hz, 1H), 6.20 (s, 1H), 5.08-4.90 (m, 1H), 4.86-4.67 (m, 1H), 4.46-4.35 (m, 1H), 4.32 (d, J = 5.5 Hz, 1H), 4.27-4.12 (m, 1H), 3.73 (s, 3H), 3.54 (s, 3H), 3.51-3.38 (m, 4H), 3.21-3.06 (m, 1H), 3.06-2.91 (m, 1H), 2.85 (s, 3H), 2.20-2.04 (m, 1H), 0.81 (d, J = 6.9 Hz, 3H), 0.74 (d, J = 6.6 Hz, 3H). |
| 15 | 459.2 | $^1H$ NMR (300 MHz, DMSO-$d_6$) δ 12.05 (s, 1H), 8.71 (d, J = 6.2 Hz, 2H), 7.60 (d, J = 5.9 Hz, 2H), 7.29 (d, J = 4.3 Hz, 2H), 6.67 (d, J = 2.7 Hz, 1H), 6.52 (d, J = 2.7 Hz, 1H), 6.23 (s, 1H), 5.49-5.22 (m, 2H), 4.58 (d, J = 4.6 Hz, 1H), 3.66 (s, 3H), 3.55 (s, 3H), 2.35-2.15 (m, 1H), 0.82 (dd, J = 6.9 Hz, 6H). |

TABLE 12-continued

| Ex. No. | MS [M + H]+ | ¹H NMR Spectra |
|---|---|---|
| 16 | 410.2 | ¹H NMR (300 MHz, DMSO-$d_6$) δ 12.02 (s, 1H), 7.32-7.21 (m, 2H), 6.76 (d, J = 2.7 Hz, 1H), 6.66 (d, J = 2.7 Hz, 1H), 6.19 (d, J = 2.2 Hz, 1H), 4.64-4.49 (m, 1H), 4.15 (d, J = 5.0 Hz, 1H), 3.76 (s, 3H), 3.53 (s, 3H), 2.15-2.02 (m, 1H), 1.47 (d, J = 6.8 Hz, 6H), 0.78 (d, J = 6.9 Hz, 3H), 0.71 (d, J = 6.7 Hz, 3H). |
| 23 | 366.1 | ¹H NMR (300 MHz, DMSO-$d_6$) δ 11.69 (s, 1H), 10.28 (s, 1H), 6.93 (d, J = 4.3 Hz, 2H), 6.21 (d, J = 2.8 Hz, 1H), 6.12 (d, J = 2.9 Hz, 1H), 5.86 (s, 1H), 3.64 (d, J = 8.2 Hz, 1H), 3.36 (s, 3H), 3.20 (s, 3H), 0.88-0.73 (m, 1H), 0.28-0.14 (m, 1H), 0.12-0.03 (m, 1H), 0.03--0.06 (m, 2H). |
| 24 | 402.1 | ¹H NMR (300 MHz, DMSO-$d_6$) δ 11.93 (s, 1H), 10.90 (s, 1H), 7.28-7.17 (m, 4H), 7.13 (t, J = 2.7 Hz, 1H), 7.02 (s, 1H), 6.49 (d, J = 2.9 Hz, 1H), 6.46 (d, J = 2.9 Hz, 1H), 5.99 (s, 1H), 5.61 (s, 1H), 3.65 (s, 3H), 3.42 (s, 3H). |
| 33 | 451.2 | ¹H NMR (300 MHz, DMSO-$d_6$) δ 12.04 (s, 1H), 10.83 (s, 1H), 7.34-7.23 (m, 2H), 7.04 (d, J = 1.9 Hz, 1H), 6.92 (d, J = 1.9 Hz, 1H), 6.23-6.12 (m, 1H), 4.49 (d, J = 4.0 Hz, 1H), 3.63-3.55 (m, 4H), 3.54 (s, 3H), 3.54-3.45 (m, 4H) 2.29-2.17 (m, 1H), 0.81 (dd, 6H). |
| 34 | 409.2 | ¹H NMR (300 MHz, DMSO-$d_6$) δ 12.04 (s, 1H), 10.81 (s, 1H), 7.30 (s, 1H), 7.27 (t, J = 2.7 Hz, 1H), 7.03 (d, J = 1.9 Hz, 1H), 6.91 (d, J = 1.9 Hz, 1H), 6.17 (t, J = 2.2 Hz, 1H), 4.49 (d, J = 3.9 Hz, 1H), 3.54 (s, 3H), 2.96 (s, 6H), 2.29-2.17 (m, 1H), 0.87-0.75 (m, 6H). |
| 40 | 409.2 | ¹H NMR (300 MHz, DMSO-$d_6$) δ 12.02 (s, 1H), 10.68 (s, 1H), 8.33 (t, J = 5.8 Hz, 1H), 7.27 (t, J = 2.5 Hz, 1H), 7.25 (s, 1H), 6.93 (s, 1H), 6.75 (d, J = 1.6 Hz, 1H), 6.20 (s, 1H), 4.35 (d, J = 4.3 Hz, 1H), 4.16 (d, J = 5.9 Hz, 2H), 3.53 (s, 3H), 2.19 (dd, J = 11.1, 6.8 Hz, 1H), 1.83 (s, 3H), 0.81 (dd, J = 13.7, 6.8 Hz, 6H). |
| 41 | 381.1 | ¹H NMR (300 MHz, DMSO-$d_6$) δ 12.02 (s, 1H), 10.84 (s, 1H), 7.87 (s, 1H), 7.55 (d, J = 1.9 Hz, 1H), 7.39 (d, J = 1.9 Hz, 1H), 7.29 (s, 1H), 7.26-7.21 (m, 2H), 6.18 (t, J = 2.2 Hz, 1H), 4.48 (d, J = 4.0 Hz, 1H), 3.55 (s, 3H), 2.28-2.13 (m, 1H), 0.79 (d, J = 6.8 Hz, 6H). |
| 45 | 402.1 | ¹H NMR (300 MHz, DMSO-$d_6$) δ 12.10 (s, 1H), 10.97 (bs, 1H), 7.55 (d, J = 2.2 Hz, 1H), 7.40 (d, J = 2.2 Hz, 1H), 7.30 (s, 2H), 6.17 (d, J = 2.4 Hz, 1H), 3.56 (s, 3H), 3.21 (s, 3H), 1.38 (s, 6H). |
| 46 | 450.1 | ¹H NMR (300 MHz, DMSO-$d_6$) δ 11.99 (s, 1H), 11.29 (bs, 1H), 7.49 (d, J = 2.2 Hz, 1H), 7.41 (d, J = 2.1 Hz, 1H), 7.32-7.21 (m, 5H), 7.20-7.10 (m, 2H), 6.00 (s, 1H), 5.87 (s, 1H), 3.44 (s, 3H), 3.17 (s, 3H). |
| 47 | 430.1 | ¹H NMR (300 MHz, DMSO-$d_6$) δ 12.06 (s, 1H), 7.58 (d, J = 2.1 Hz, 1H), 7.52 (d, J = 2.1 Hz, 1H), 7.34 (s, 1H), 7.25 (d, J = 2.8 Hz, 1H), 6.15 (d, J = 2.8 Hz, 1H), 4.59 (d, J = 4.2 Hz, 1H), 3.51 (s, 3H), 3.34 (s, 3H), 2.25-2.13 (m, 1H), 0.73 (dd, J = 6.7, 4.8 Hz, 6H). |
| 48 | 418.1 | ¹H NMR (300 MHz, DMSO-$d_6$) δ 12.11 (s, 1H), 11.03 (s, 1H), 7.55 (d, J = 2.1 Hz, 1H), 7.44-7.35 (m, 2H), 7.30 (t, J = 2.7 Hz, 1H), 6.20 (d, J = 2.0 Hz, 1H), 4.82 (dd, J = 9.3, 3.4 Hz, 1H), 4.51 (t, J = 5.3 Hz, 1H), 3.56 (s, 3H), 3.36-3.28 (m, 2H), 3.21 (s, 3H), 2.12-1.95 (m, 1H), 1.87-1.70 (m, 1H). |
| 49 | 380.1 | ¹H NMR (300 MHz, DMSO-$d_6$) δ 12.01 (s, 1H), 10.84 (s, 1H), 7.61 (d, J = 2.1 Hz, 1H), 7.39 (d, J = 2.1 Hz, 1H), 7.28 (s, 1H), 7.23 (t, J = 2.6 Hz, 1H), 6.15 (s, 0H), 4.51 (d, J = 4.0 Hz, 1H), 3.50 (s, 3H), 2.47 (s, 3H), 2.24-2.09 (m, 1H), 0.75 (dd, J = 6.8, 3.1 Hz, 6H). |
| 52 | 444.1 | ¹H NMR (300 MHz, DMSO-$d_6$) δ 12.05 (s, 1H), 10.92 (s, 1H), 7.36 (d, J = 2.2 Hz, 1H), 7.33 (s, 1H), 7.24 (dd, J = 5.0, 2.5 Hz, 2H), 6.12 (d, J = 2.8 Hz, 1H), 4.54 (d, J = 3.8 Hz, 1H), 3.50 (s, 3H), 3.39-3.29 (m, 1H), 2.27-2.14 (m, 1H), 1.12 (d, J = 6.7 Hz, 6H), 0.76 (dd, J = 6.8, 4.4 Hz, 6H). |
| 53 | 470.2 | |
| 54 | 444.2 | ¹H NMR (300 MHz, DMSO-$d_6$) δ 12.06 (s, 1H), 7.58 (d, J = 1.8 Hz, 1H), 7.53 (d, J = 1.9 Hz, 1H), 7.33 (s, 1H), 7.24 (d, J = 2.7 Hz, 1H), 6.14 (d, J = 2.7 Hz, 1H), 4.56 (d, J = 4.5 Hz, 1H), 4.08-3.90 (m, 2H), 3.50 (s, 3H), 3.24 (s, 3H), 2.24-2.08 (m, 1H), 1.15 (t, J = 6.9 Hz, 3H), 0.72 (dd, J = 6.8 Hz, 6H). |
| 55 | 444.2 | ¹H NMR (300 MHz, DMSO-$d_6$) δ 12.11 (s, 1H), 7.58 (d, J = 1.8 Hz, 1H), 7.51 (d, J = 1.9 Hz, 1H), 7.39 (s, 1H), 7.30 (s, 1H), 6.17 (s, 1H), 4.65 (d, J = 4.1 Hz, 1H), 3.55 (s, 3H), 3.38 (s, 3H), 3.36-3.31 (m, 1H), 2.34-2.17 (m, 1H), 1.14 (t, J = 7.3 Hz, 3H), 0.79 (dd, J = 6.5 Hz, 6H). |
| 56 | 458.2 | ¹H NMR (300 MHz, DMSO-$d_6$) δ 12.07 (s, 1H), 7.50 (d, J = 2.0 Hz, 1H), 7.41 (d, J = 2.0 Hz, 1H), 7.34 (s, 1H), 7.25 (d, J = 2.8 Hz, 1H), 6.10 (d, J = 2.7 Hz, 1H), 4.60 (d, J = 4.1 Hz, 1H), 3.50 (s, 3H), 3.49-3.43 (m, 1H), 3.33 (s, 3H), 2.28-2.17 (m, 1H), 1.15 (d, J = 6.8 Hz, 6H), 0.75 (dd, J = 7.3 Hz, 6H). |
| 59 | 427.1 | ¹H NMR (300 MHz, DMSO-$d_6$) δ 12.07 (s, 1H), 10.59 (s, 1H), 7.26-7.18 (m, 3H), 7.14 (s, 1H), 5.95 (s, 1H), 5.64 (s, 1H), 3.48 (s, 3H), 3.06 (s, 3H), 2.02-1.88 (m, 2H), 1.65-1.44 (m, 6H). |
| 60 | 415.1 | |
| 61 | 415.1 | |
| 62 | 413.1 | ¹H NMR (500 MHz, DMSO-$d_6$) δ 12.10 (s, 1H), 10.59 (s, 1H), 7.29 (d, J = 2.7 Hz, 1H), 7.25 (s, 2H), 7.24 (s, 1H), 6.30 (s, 1H), 6.02 (d, J = 2.7 Hz, 1H), 3.56 (s, 3H), 3.10 (s, 3H), 2.43 (t, J = 9.4 Hz, 2H), 2.15 (q, J = 9.9 Hz, 2H), 1.81-1.69 (m, 1H), 1.66-1.54 (m, 1H). |

TABLE 12-continued

| Ex. No. | MS [M + H]⁺ | ¹H NMR Spectra |
|---|---|---|
| 65 | 401.1 | ¹H NMR (300 MHz, DMSO-$d_6$) δ 7.78 (s, 1H), 7.49 (d, J = 2.2 Hz, 1H), 7.39 (d, J = 2.2 Hz, 1H), 7.30 (s, 1H), 5.69 (s, 1H), 3.50 (s, 3H), 3.18 (s, 3H), 1.26-1.18 (m, 2H), 1.06-0.97 (m, 2H). |
| 66 | 415.1 | ¹H NMR (300 MHz, DMSO-$d_6$) δ 7.77 (s, 1H), 7.58 (s, 1H), 7.57 (s, 1H), 7.30 (s, 1H), 3.51 (s, 3H), 3.36 (s, 3H), 3.25 (s, 3H), 1.27-1.19 (m, 2H), 1.08-0.99 (m, 2H). |
| 68 | 431.2 | ¹H NMR (300 MHz, DMSO-$d_6$) δ 7.29 (s, 2H), 7.25 (d, J = 2.6 Hz, 1H), 7.15 (s, 1H), 6.18-6.08 (m, 1H), 4.4-4.3(m, 1H), 3.50 (s, 3H), 2.37 (s, 3H), 2.22-2.09 (m, 1H), 0.76 (dd, J = 9.1, 7.0 Hz, 6H). |
| 69 | 445.2 | ¹H NMR (300 MHz, DMSO-$d_6$) δ 12.13 (s, 1H), 7.43 (d, J = 2.0 Hz, 1H), 7.34 (d, J = 2.0 Hz, 1H), 7.30 (t, J = 2.7 Hz, 1H), 7.29 (s, 1H), 6.11 (d, J = 2.2 Hz, 1H), 3.56 (s, 3H), 3.38 (s, 3H), 2.66 (s, 6H), 1.39 (s, 6H). |
| 70 | 431.1 | ¹H NMR (300 MHz, DMSO-$d_6$) δ 12.11 (s, 1H), 10.93 (s, 1H), 7.33-7.29 (m, 2H), 7.29 (s, 1H), 7.26 (s, 1H), 6.13 (s, 1H), 3.56 (s, 3H), 2.63 (s, 6H), 1.39 (s, 6H). |
| 71 | 459.1 | |
| 72 | 471.1 | ¹H NMR (300 MHz, DMSO-$d_6$) δ 12.05 (s, 1H), 7.24 (d, J = 2.7 Hz, 1H), 7.21 (s, 1H), 7.11 (s, 1H), 7.04 (s, 1H), 6.07 (d, J = 2.7 Hz, 1H), 3.50 (s, 3H), 2.84 (bs, 4H), 1.54-1.30 (m, 6H), 1.27 (s, 6H). |
| 73 | 485.2 | ¹H NMR (300 MHz, DMSO-$d_6$) δ 12.10 (s, 1H), 7.37 (d, J = 2.0 Hz, 1H), 7.26 (d, J = 2.8 Hz, 2H), 7.24 (s, 1H), 6.05 (d, J = 2.8 Hz, 1H), 3.51 (s, 3H), 3.33 (s, 3H), 2.89 (bs, 4H), 1.55-1.36 (m, 6H), 1.34 (s, 6H). |
| 74 | 445.2 | ¹H NMR (300 MHz, DMSO-$d_6$) δ 7.30 (s, 1H), 7.25 (d, J = 2.8 Hz, 1H), 7.19 (s, 2H), 6.08 (d, J = 2.8 Hz, 1H), 3.50 (s, 3H), 3.22-3.14 (m, 1H), 1.28 (s, 6H), 0.90 (d, J = 6.5 Hz, 6H). |
| 75 | 416.1 | ¹H NMR (300 MHz, DMSO-$d_6$) δ 12.11 (s, 1H), 7.63 (d, J = 1.7 Hz, 1H), 7.59 (d, J = 1.9 Hz, 1H), 7.30 (d, J = 2.7 Hz, 2H), 6.15 (d, J = 2.1 Hz, 1H), 3.56 (s, 3H), 3.40 (s, 3H), 3.28 (s, 3H), 1.38 (s, 6H). |
| 76 | 430.1 | ¹H NMR (300 MHz, DMSO-$d_6$) δ 12.12 (s, 1H), 7.58 (d, J = 1.9 Hz, 1H), 7.52 (d, J = 2.0 Hz, 1H), 7.30 (d, J = 2.6 Hz, 2H), 6.13 (d, J = 2.1 Hz, 1H), 3.56 (s, 3H), 3.39 (s, 3H), 3.34 (q, J = 7.4 Hz, 2H), 1.38 (s, 6H), 1.14 (t, J = 7.3 Hz, 3H). |
| 77 | 444.2 | ¹H NMR (500 MHz, DMSO-$d_6$) δ 12.11 (s, 1H), 7.55 (d, J = 2.0 Hz, 1H), 7.48 (d, J = 2.0 Hz, 1H), 7.33-7.26 (m, 2H), 6.11 (d, J = 2.8 Hz, 1H), 3.57 (s, 3H), 3.55-3.49 (m, 1H), 3.39 (s, 3H), 1.40 (s, 6H), 1.21 (d, J = 6.8 Hz, 6H). |
| 78 | 416.1 | ¹H NMR (300 MHz, DMSO-$d_6$) δ 12.13 (s, 1H), 11.01 (s, 1H), 7.48 (d, J = 2.2 Hz, 1H), 7.36 (d, J = 2.2 Hz, 1H), 7.30 (s, 2H), 6.15 (s, 1H), 3.56 (s, 3H), 3.27 (q, J = 7.3 Hz, 1H), 1.39 (s, 6H), 1.13 (t, J = 7.3 Hz, 3H). |
| 79 | 430.1 | ¹H NMR (300 MHz, DMSO-$d_6$) δ 12.10 (s, 1H), 8.53 (s, 1H), 7.38 (s, 1H), 7.32-7.23 (m, 3H), 6.13 (d, J = 2.7 Hz, 1H), 3.56 (s, 3H), 3.41-3.34 (m, 1H), 3.31 (s, 3H), 1.37 (s, 6H), 1.17 (d, J = 6.8 Hz, 6H). |
| 80 | 366.2 | |
| 81 | 368.2 | ¹H NMR (300 MHz, DMSO-$d_6$) δ 12.02 (s, 1H), 10.63 (s, 1H), 7.27 (t, J = 2.7 Hz, 1H), 7.17 (s, 1H), 6.97 (d, J = 1.9 Hz, 1H), 6.89 (d, J = 1.9 Hz, 1H), 6.20-6.09 (m, 1H), 5.14 (d, J = 4.0 Hz, 1H), 4.73-4.56 (m, 1H), 3.54 (s, 3H), 1.38-1.25 (m, 9H). |
| 82 | 380.2 | ¹H NMR (300 MHz, DMSO-$d_6$) δ 12.08 (s, 1H), 7.75 (d, J = 1.8 Hz, 1H), 7.62 (d, J = 1.8 Hz, 1H), 7.28 (s, 1H), 7.26 (s, 1H), 6.14 (d, J = 2.6 Hz, 1H), 3.56 (s, 3H), 3.39 (s, 3H), 2.59 (s, 3H), 1.36 (s, 6H). |
| 83 | 382.2 | ¹H NMR (300 MHz, DMSO-$d_6$) δ 11.99 (s, 1H), 7.22 (t, J = 2.7 Hz, 1H), 7.12 (s, 1H), 7.04 (s, 2H), 6.08 (t, J = 2.3 Hz, 1H), 5.14 (d, J = 4.3 Hz, 1H), 4.77-4.60 (m, 1H), 3.50 (s, 3H), 3.27 (s, 3H), 1.30 (d, J = 6.4 Hz, 3H), 1.27 (s, 6H). |

Example A1: BRD4 AlphaScreen™ Assay

BRD4 AlphaScreen™ Assay

BRD4-BD1 and BRD4-BD2 assays were conducted in white 384-well polystyrene plate in a final volume of 40 µL for BD1 and 60 µL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature in the assay buffer (50 mM Tris-HCl, pH 7.5, 0.01% Tween-20, 0.01% BSA, 5 mM DTT), containing 50 nM Biotin-labeled tetra-acetylated histone H4 peptide (H4Ac4) and BRD4-BD1 or BRD4-BD2 protein at concentration less than 1 nM. The incubation for 75 min. was followed by the addition of 20 µL of assay buffer supplemented with Streptavidin donor beads (PerkinElmer 6760002) and GSH Acceptor beads (PerkinElmer-AL109C) at final concentration 2-4 µg/mL under reduced light. After plate sealing, the plate was incubated in the dark at room temperature for 75 min. before reading on a PHERAstar FS plate reader (BMG Labtech). $IC_{50}$ determination was performed by fitting the curve of percent control activity versus the log of the inhibitor concentration using the GraphPad Prism 5.0 software.

$IC_{50}$ data for the Examples is presented in Table 13 as determined by Assay A1 (column symbols: + refers to ≤100 nM; ++ refers to >100 nM and ≤1000 nM; +++ refers to >1000 nM and ≤10,000 nM).

TABLE 13

| Ex. No. | BRD4-BD1 IC$_{50}$ (nM) | BRD4-BD2 IC$_{50}$ (nM) |
| --- | --- | --- |
| 1 | + | + |
| 2 | + | + |
| 3 | ++ | + |
| 4 | ++ | + |
| 5 | ++ | + |
| 6 | + | + |
| 7 | + | + |
| 8 | ++ | + |
| 9 | + | + |
| 9A | + | + |
| 9B | + | + |
| 10 | + | + |
| 11 | ++ | ++ |
| 12 | ++ | + |
| 13 | ++ | + |
| 14 | ++ | + |
| 15 | + | + |
| 16 | ++ | + |
| 17 | ++ | + |
| 18 | ++ | + |
| 19 | ++ | + |
| 20 | + | + |
| 21 | ++ | + |
| 22 | ++ | + |
| 23 | + | + |
| 24 | + | + |
| 24A | + | + |
| 24B | + | + |
| 25 | + | + |
| 26 | + | + |
| 27 | + | + |
| 28 | ++ | + |
| 29 | + | + |
| 30 | + | + |
| 31 | + | + |
| 32 | ++ | + |
| 33 | + | + |
| 34 | + | + |
| 35 | + | + |
| 35A | + | + |
| 35B | + | + |
| 36 | + | + |
| 37 | + | + |
| 38 | ++ | + |
| 39 | + | + |
| 40 | + | + |
| 41 | + | + |
| 42 | + | + |
| 42A | + | + |
| 42B | + | + |
| 43 | ++ | + |
| 44 | + | + |
| 44A | + | + |
| 44B | + | + |
| 45 | + | + |
| 46 | + | + |
| 47 | + | + |
| 47A | + | + |
| 47B | + | + |
| 48 | + | + |
| 49 | + | + |
| 50 | + | + |
| 51 | + | + |
| 52 | + | + |
| 53 | + | + |
| 54 | + | + |
| 55 | + | + |
| 56 | + | + |
| 57 | + | + |
| 58 | + | + |
| 59 | + | + |
| 60 | + | + |
| 61 | + | + |
| 62 | + | + |
| 63 | + | + |
| 64 | + | + |
| 65 | + | + |
| 66 | + | + |
| 67 | + | + |
| 68 | + | + |
| 69 | + | + |
| 70 | + | + |
| 71 | + | + |
| 72 | + | + |
| 73 | + | + |
| 74 | + | + |
| 75 | + | + |
| 76 | + | + |
| 77 | + | + |
| 78 | + | + |
| 79 | + | + |
| 80 | + | + |
| 81 | + | + |
| 82 | + | + |
| 83 | + | + |
| 83A | + | + |
| 83B | + | + |
| 84 | + | + |

Example B1: KMS.12.BM Cell Viability Assay

KMS. 12.BM cell line (human myeloma) was purchased from JCRB (Osaka, Japan) and maintained in RPMI with 10% FBS culture medium. To measure the cytotoxic activity of the compounds through ATP quantitation, the KMS. 12.BM cells are plated in the RPMI culture medium at 5000 cells/well/per 100 µL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 minutes at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the IC$_{50}$ is reported as the compound concentration required for 50% cell death. IC$_{50}$ data for the Examples is presented in Table 14 as determined by Assay B1 (column symbols: + refers to ≤1000 nM; ++ refers to >1000 nM and ≤10,000 nM; NA indicates that data was not available).

TABLE 14

| Ex. No. | KMS.12.BM IC$_{50}$ (nM) |
| --- | --- |
| 1 | + |
| 2 | + |
| 3 | + |
| 4 | + |
| 5 | + |
| 6 | + |
| 7 | + |
| 8 | + |
| 9 | + |
| 9A | + |
| 9B | + |
| 10 | + |
| 11 | NA |
| 12 | + |
| 13 | + |

TABLE 14-continued

| Ex. No. | KMS.12.BM IC$_{50}$ (nM) |
|---|---|
| 14 | + |
| 15 | + |
| 16 | + |
| 17 | + |
| 18 | + |
| 19 | + |
| 20 | + |
| 21 | + |
| 22 | ++ |
| 23 | ++ |
| 24 | + |
| 24A | + |
| 24B | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 35A | + |
| 35B | + |
| 36 | + |
| 37 | + |
| 38 | NA |
| 39 | NA |
| 40 | + |
| 41 | + |
| 42 | + |
| 42A | + |
| 42B | + |
| 43 | NA |
| 44 | + |
| 44A | + |
| 44B | + |
| 45 | + |
| 46 | + |
| 47 | + |
| 47A | + |
| 47B | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 83A | + |
| 83B | + |
| 84 | + |

Example C1: KMS.12.BM C-myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells/well/per 200 μL into a 96-well flat bottom polystyrene tissue culture plate (Corning through VWR, NJ), in the presence or absence of a concentration range of test compounds. After 2 hours, cell are pelleted and lysed with Cell Extraction Buffer (BioSource, Carlsbad, Calif.) in the presence of protease inhibitors (Life Technologies, Grand Island, N.Y. and Sigma, St Louis, Mo.). Clarified lyses are tested in a C-myc commercial ELISA (Life Technologies, Grand Island, N.Y.). Compound inhibition is determined relative to cells cultured with no drug and the IC$_{50}$ is reported as the compound concentration required for 50% C-myc inhibition.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula IIIa:

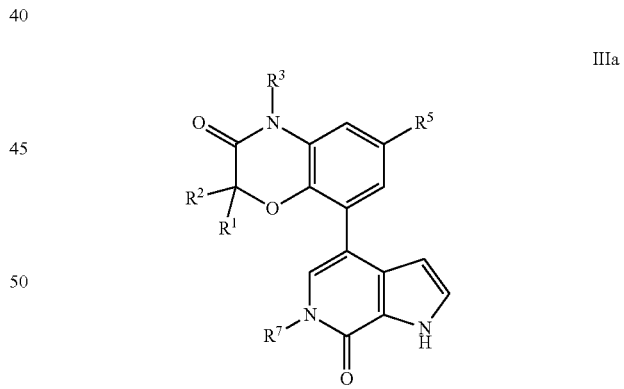

or a pharmaceutically acceptable salt thereof, wherein:
$R^1$ and $R^2$ are each independently selected from H, methyl, ethyl, propyl, cyclopropyl, cyclopentyl, pyran-4-yl, phenyl, pyridin-2-yl, 2-chloro-4-phenyl, 2-chloro-4-fluorophenyl, and 2-hydroxyethyl;
or $R^1$ and $R^2$ together with the carbon atom to which they are attached form cyclopropyl;
$R^3$ is H, methyl, ethyl, or propyl, wherein said methyl is optionally substituted with cyclopropyl, pyridinyl, —C(=O)NH$_2$, —C(=O)NHCH$_3$, —C(=O)(4-methylpiperazin-1-yl), —C(=O)NH(4-methylpiperazin-1-yl), or —C(=O)OH;

R⁵ is H, 1-methyl-1H-pyrazol-4-yl, 2-furyl, CN, NO$_2$, methoxy, —C(=O)NH$_2$, —C(=O)NH(CH$_3$), —C(=O)N(CH$_3$)$_2$, —C(=O)-(morpholin-4-yl), —C(=O)CH$_3$, —CH$_2$OH, —CH$_2$OCH$_3$, —CH$_2$NH$_2$, —CH$_2$NHSO$_2$(CH$_2$CH$_3$), —CH$_2$NHC(=O)CH$_3$, —CH(OH)CH$_3$, —SO$_2$CH$_3$, —SO$_2$CH$_2$CH$_3$, —SO$_2$-(isopropyl), —SO$_2$N(CH$_3$)$_2$, —SO$_2$NH(CH$_3$), —SO$_2$—NH(isopropyl), or —SO$_2$-(piperidin-1-yl); and;

R⁷ is methyl.

2. The compound of claim 1, or a pharmaceutically acceptable salt thereof, wherein R¹ and R² are each independently selected from H, methyl, ethyl, propyl, cyclopropyl, cyclopentyl, pyran-4-yl, phenyl, pyridin-2-yl, 2-chloro-4-phenyl, and 2-hydroxyethyl.

3. The compound of claim 1, or a pharmaceutically acceptable salt thereof, wherein one of R¹ and R² is H and the other is not H.

4. The compound of claim 1, or a pharmaceutically acceptable salt thereof, wherein R¹ and R² are each methyl, ethyl, or propyl.

5. The compound of claim 1, or a pharmaceutically acceptable salt thereof, wherein R¹ and R² are each methyl.

6. The compound of claim 1, or a pharmaceutically acceptable salt thereof, wherein R³ is H, methyl, ethyl, or propyl, wherein said methyl is optionally substituted with cyclopropyl, pyridinyl, —C(=O)NHCH$_3$, —C(=O)NH(4-methylpiperazin-1-yl), or —C(=O)OH.

7. The compound of claim 1, or a pharmaceutically acceptable salt thereof, wherein R³ is methyl.

8. The compound of claim 1, or a pharmaceutically acceptable salt thereof, wherein R⁵ is SO$_2$CH$_3$, SO$_2$CH$_2$CH$_3$, SO$_2$-(isopropyl), SO$_2$N(CH$_3$)$_2$, SO$_2$NH(CH$_3$), SO$_2$NH(isopropyl), or SO$_2$-(piperidin-1-yl).

9. The compound of claim 1, or a pharmaceutically acceptable salt thereof, wherein R⁵ is S(O)$_2$CH$_3$.

10. The compound of claim 1, or a pharmaceutically acceptable salt thereof, wherein R⁵ is S(O)$_2$CH$_2$CH$_3$.

11. The compound of claim 1, selected from:
- 8-(6-methyl-7-oxo-6,7-dihydro-1H-pyrrolo[2,3-c]pyridin-4-yl)-2-phenyl-2H-1,4-benzoxazin-3(4H)-one;
- 2-isopropyl-8-(6-methyl-7-oxo-6,7-dihydro-1H-pyrrolo[2,3-c]pyridin-4-yl)-2H-1,4-benzoxazin-3(4H)-one;
- 2-methyl-8-(6-methyl-7-oxo-6,7-dihydro-1H-pyrrolo[2,3-c]pyridin-4-yl)-2H-1,4-benzoxazin-3(4H)-one;
- 2-ethyl-8-(6-methyl-7-oxo-6,7-dihydro-1H-pyrrolo[2,3-c]pyridin-4-yl)-2H-1,4-benzoxazin-3(4H)-one;
- 8-(6-methyl-7-oxo-6,7-dihydro-1H-pyrrolo[2,3-c]pyridin-4-yl)-2-pyridin-2-yl-2H-1,4-benzoxazin-3(4H)-one 2,2,2-trifluoroacetate;
- 2-cyclopropyl-8-(6-methyl-7-oxo-6,7-dihydro-1H-pyrrolo[2,3-c]pyridin-4-yl)-2H-1,4-benzoxazin-3(4H)-one;
- 8-(6-methyl-7-oxo-6,7-dihydro-1H-pyrrolo[2,3-c]pyridin-4-yl)-2-(tetrahydro-2H-pyran-4-yl)-2H-1,4-benzoxazin-3(4H)-one;
- 2-ethyl-4-methyl-8-(6-methyl-7-oxo-6,7-dihydro-1H-pyrrolo[2,3-c]pyridin-4-yl)-2H-1,4-benzoxazin-3(4H)-one;
- 2-isopropyl-6-methoxy-8-(6-methyl-7-oxo-6,7-dihydro-1H-pyrrolo[2,3-c]pyridin-4-yl)-2H-1,4-benzoxazin-3(4H)-one;
- 2-isopropyl-6-methoxy-4-methyl-8-(6-methyl-7-oxo-6,7-dihydro-1H-pyrrolo[2,3-c]pyridin-4-yl)-2H-1,4-benzoxazin-3(4H)-one;
- [2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]acetic acid;
- 2-[2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]-N-methylacetamide;
- 2-[2-isopropyl-6-methoxy-8-(6-methyl-7-oxo-6,7-dihydro-1H-pyrrolo[2,3-c]pyridin-4-yl)-3-oxo-2,3-dihydro-4H-1,4-benzoxazin-4-yl]acetamide;
- 2-isopropyl-6-methoxy-8-(6-methyl-7-oxo-6,7-dihydro-1H-pyrrolo[2,3-c]pyridin-4-yl)-4-[2-(4-methylpiperazin-1-yl)-2-oxoethyl]-2H-1,4-benzoxazin-3(4H)-one;
- 2-isopropyl-6-methoxy-8-(6-methyl-7-oxo-6,7-dihydro-1H-pyrrolo[2,3-c]pyridin-4-yl)-4-(pyridin-4-ylmethyl)-2H-1,4-benzoxazin-3(4H)-one;
- 2,4-diisopropyl-6-methoxy-8-(6-methyl-7-oxo-6,7-dihydro-1H-pyrrolo[2,3-c]pyridin-4-yl)-2H-1,4-benzoxazin-3(4H)-one;
- 2-isopropyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile;
- 2-isopropyl-4-methyl-8-(6-methyl-7-oxo-6,7-dihydro-1H-pyrrolo[2,3-c]pyridin-4-yl)-3-oxo-3,4-dihydro-2H-1,4-benzoxazine-6-carbonitrile;
- 2-isopropyl-4-methyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide;
- 2-isopropyl-N-methyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide;
- 2-isopropyl-8-(6-methyl-7-oxo-6,7-dihydro-1H-pyrrolo[2,3-c]pyridin-4-yl)-6-nitro-2H-1,4-benzoxazin-3(4H)-one;
- 2-cyclopropyl-6-methoxy-8-(6-methyl-7-oxo-6,7-dihydro-1H-pyrrolo[2,3-c]pyridin-4-yl)-2H-1,4-benzoxazin-3(4H)-one;
- 6-methoxy-8-(6-methyl-7-oxo-6,7-dihydro-1H-pyrrolo[2,3-c]pyridin-4-yl)-2-phenyl-2H-1,4-benzoxazin-3(4H)-one;
- 2-(2-chloro-4-fluorophenyl)-6-methoxy-8-(6-methyl-7-oxo-6,7-dihydro-1H-pyrrolo[2,3-c]pyridin-4-yl)-2H-1,4-benzoxazin-3(4H)-one;
- 6-methoxy-2,2-dimethyl-8-(6-methyl-7-oxo-6,7-dihydro-1H-pyrrolo[2,3-c]pyridin-4-yl)-2H-1,4-benzoxazin-3(4H)-one;
- 2-isopropyl-8-(6-methyl-7-oxo-6,7-dihydro-1H-pyrrolo[2,3-c]pyridin-4-yl)-6-(1-methyl-1H-pyrazol-4-yl)-2H-1,4-benzoxazin-3(4H)-one;
- 8-(6-methyl-7-oxo-6,7-dihydro-1H-pyrrolo[2,3-c]pyridin-4-yl)spiro[1,4-benzoxazine-2,1'-cyclopropan]-3(4H)-one;
- 2,2-dimethyl-8-(6-methyl-7-oxo-6,7-dihydro-1H-pyrrolo[2,3-c]pyridin-4-yl)-2H-1,4-benzoxazin-3(4H)-one;
- 2-isopropyl-8-(6-methyl-7-oxo-6,7-dihydro-1H-pyrrolo[2,3-c]pyridin-4-yl)-6-(morpholin-4-ylcarbonyl)-2H-1,4-benzoxazin-3(4H)-one;
- 2-isopropyl-N,N-dimethyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide;
- 2-cyclopentyl-6-methoxy-8-(6-methyl-7-oxo-6,7-dihydro-1H-pyrrolo[2,3-c]pyridin-4-yl)-2H-1,4-benzoxazin-3(4H)-one;
- 6-(hydroxymethyl)-2-isopropyl-8-(6-methyl-7-oxo-6,7-dihydro-1H-pyrrolo[2,3-c]pyridin-4-yl)-2H-1,4-benzoxazin-3(4H)-one;

2-isopropyl-6-(methoxymethyl)-8-(6-methyl-7-oxo-6,7-dihydro-1H-pyrrolo[2,3-c]pyridin-4-yl)-2H-1,4-benzoxazin-3(4H)-one;

6-(Aminomethyl)-2-isopropyl-8-(6-methyl-7-oxo-6,7-dihydro-1H-pyrrolo[2,3-c]pyridin-4-yl)-2H-1,4-benzoxazin-3(4H)-one;

N-{[2-isopropyl-8-(6-methyl-7-oxo-6, 7-dihydro-1H-pyrrolo[2,3-c]pyridin-4-yl)-3-oxo-3,4-dihydro-2H-1,4-benzoxazin-6-yl]methyl}ethanesulfonamide;

N-{[2-isopropyl-8-(6-methyl-7-oxo-6, 7-dihydro-1H-pyrrolo[2,3-c]pyridin-4-yl)-3-oxo-3,4-dihydro-2H-1,4-benzoxazin-6-yl]methyl}acetamide;

2-isopropyl-8-(6-methyl-7-oxo-6,7-dihydro-1H-pyrrolo[2,3-c]pyridin-4-yl)-3-oxo-3,4-dihydro-2H-1,4-benzoxazine-6-carboxamide;

6-(2-furyl)-2-isopropyl-8-(6-methyl-7-oxo-6,7-dihydro-1H-pyrrolo[2,3-c]pyridin-4-yl)-2H-1,4-benzoxazin-3(4H)-one;

2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one;

2,2-dimethyl-8-(6-methyl-7-oxo-6,7-dihydro-1H-pyrrolo[2,3-c]pyridin-4-yl)-6-(methylsulfonyl)-2H-1,4-benzoxazin-3(4H)-one;

8-(6-methyl-7-oxo-6,7-dihydro-1H-pyrrolo[2,3-c]pyridin-4-yl)-6-(methylsulfonyl)-2-phenyl-2H-1,4-benzoxazin-3(4H)-one;

2-isopropyl-4-methyl-8-(6-methyl-7-oxo-6,7-dihydro-1H-pyrrolo[2,3-c]pyridin-4-yl)-6-(methylsulfonyl)-2H-1,4-benzoxazin-3(4H)-one;

2-(2-hydroxyethyl)-8-(6-methyl-7-oxo-6,7-dihydro-1H-pyrrolo[2,3-c]pyridin-4-yl)-6-(methylsulfonyl)-2H-1,4-benzoxazin-3(4H)-one;

6-acetyl-2-isopropyl-8-(6-methyl-7-oxo-6,7-dihydro-1H-pyrrolo[2,3-c]pyridin-4-yl)-2H-1,4-benzoxazin-3(4H)-one;

6-(1-hydroxyethyl)-2-isopropyl-8-(6-methyl-7-oxo-6,7-dihydro-1H-pyrrolo[2,3-c]pyridin-4-yl)-2H-1,4-benzoxazin-3(4H)-one;

6-(ethylsulfonyl)-2-isopropyl-8-(6-methyl-7-oxo-6,7-dihydro-1H-pyrrolo[2,3-c]pyridin-4-yl)-2H-1,4-benzoxazin-3(4H)-one;

2-isopropyl-6-(isopropylsulfonyl)-8-(6-methyl-7-oxo-6,7-dihydro-1H-pyrrolo[2,3-c]pyridin-4-yl)-2H-1,4-benzoxazin-3(4H)-one;

4-(cyclopropylmethyl)-2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one;

4-ethyl-2-isopropyl-8-(6-methyl-7-oxo-6,7-dihydro-1H-pyrrolo[2,3-c]pyridin-4-yl)-6-(methylsulfonyl)-2H-1,4-benzoxazin-3(4H)-one;

6-(ethylsulfonyl)-2-isopropyl-4-methyl-8-(6-methyl-7-oxo-6,7-dihydro-1H-pyrrolo[2,3-c]pyridin-4-yl)-2H-1,4-benzoxazin-3(4H)-one;

2-isopropyl-6-(isopropylsulfonyl)-4-methyl-8-(6-methyl-7-oxo-6,7-dihydro-1H-pyrrolo[2,3-c]pyridin-4-yl)-2H-1,4-benzoxazin-3(4H)-one;

8-(6-methyl-7-oxo-6,7-dihydro-1H-pyrrolo[2,3-c]pyridin-4-yl)-6-(methylsulfonyl)spiro[1,4-benzoxazine-2,1'-cyclopropan]-3(4H)-one;

4-methyl-8-(6-methyl-7-oxo-6,7-dihydro-1H-pyrrolo[2,3-c]pyridin-4-yl)-6-(methylsulfonyl)spiro[1,4-benzoxazine-2,1'-cyclopropan]-3(4H)-one;

2-isopropyl-N,N-dimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide;

2-isopropyl-N-methyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide;

N,N,2,2,4-pentamethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide;

N,N,2,2-tetramethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide;

2-isopropyl-N,N,4-trimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide;

2,2-dimethyl-8-(6-methyl-7-oxo-6,7-dihydro-1H-pyrrolo[2,3-c]pyridin-4-yl)-6-(piperidin-1-ylsulfonyl)-2H-1,4-benzoxazin-3(4H)-one;

2,2,4-trimethyl-8-(6-methyl-7-oxo-6,7-dihydro-1H-pyrrolo[2,3-c]pyridin-4-yl)-6-(piperidin-1-ylsulfonyl)-2H-1,4-benzoxazin-3(4H)-one;

N-isopropyl-2,2-dimethyl-8-(6-methyl-7-oxo-6,7-dihydro-1H-pyrrolo[2,3-c]pyridin-4-yl)-3-oxo-3,4-dihydro-2H-1,4-benzoxazine-6-sulfonamide;

2,2,4-trimethyl-8-(6-methyl-7-oxo-6,7-dihydro-1H-pyrrolo[2,3-c]pyridin-4-yl)-6-(methylsulfonyl)-2H-1,4-benzoxazin-3(4H)-one;

6-(ethylsulfonyl)-2,2,4-trimethyl-8-(6-methyl-7-oxo-6,7-dihydro-1H-pyrrolo[2,3-c]pyridin-4-yl)-2H-1,4-benzoxazin-3(4H)-one;

6-(isopropylsulfonyl)-2,2,4-trimethyl-8-(6-methyl-7-oxo-6,7-dihydro-1H-pyrrolo[2,3-c]pyridin-4-yl)-2H-1,4-benzoxazin-3(4H)-one;

6-(ethylsulfonyl)-2,2-dimethyl-8-(6-methyl-7-oxo-6,7-dihydro-1H-pyrrolo[2,3-c]pyridin-4-yl)-2H-1,4-benzoxazin-3(4H)-one;

6-(isopropylsulfonyl)-2,2-dimethyl-8-(6-methyl-7-oxo-6,7-dihydro-1H-pyrrolo[2,3-c]pyridin-4-yl)-2H-1,4-benzoxazin-3(4H)-one;

6-acetyl-2,2-dimethyl-8-(6-methyl-7-oxo-6,7-dihydro-1H-pyrrolo[2,3-c]pyridin-4-yl)-2H-1,4-benzoxazin-3(4H)-one;

6-(1-hydroxyethyl)-2,2-dimethyl-8-(6-methyl-7-oxo-6,7-dihydro-1H-pyrrolo[2,3-c]pyridin-4-yl)-2H-1,4-benzoxazin-3(4H)-one;

6-acetyl-2,2,4-trimethyl-8-(6-methyl-7-oxo-6,7-dihydro-1H-pyrrolo[2,3-c]pyridin-4-yl)-2H-1,4-benzoxazin-3(4H)-one; and 6-(1-hydroxyethyl)-2,2,4-trimethyl-8-(6-methyl-7-oxo-6,7-dihydro-1H-pyrrolo[2,3-c]pyridin-4-yl)-2H-1,4-benzoxazin-3(4H)-one;

or a pharmaceutically acceptable salt of any of the aforementioned.

12. A pharmaceutical composition comprising a compound of claim 1, or a pharmaceutically acceptable salt thereof, and at least one pharmaceutically acceptable carrier.

\* \* \* \* \*

UNITED STATES PATENT AND TRADEMARK OFFICE
CERTIFICATE OF CORRECTION

PATENT NO. : 9,957,268 B2
APPLICATION NO. : 15/354223
DATED : May 1, 2018
INVENTOR(S) : Andrew P. Combs, Thomas P. Maduskuie, Jr. and Nikoo Falahatpisheh Page 1 of 1

It is certified that error appears in the above-identified patent and that said Letters Patent is hereby corrected as shown below:

On the Title Page

Column 1 Item (54) (Title), Line 1, delete "[2,3,C]" and insert -- [2,3-C] --;

Column 1 (Notice), Line 3, after "0 days." delete "days.";

In the Specification

Column 1, Line 1, delete "[2,3,C]" and insert -- [2,3-C] --;

In the Claims

Column 127, Line 7, Claim 11, delete "-6, 7-dihydro-" and insert -- -6,7-dihydro- --;

Column 127, Lines 8-9, Claim 11, delete "-1, 4-" and insert -- -1,4- --;

Column 127, Line 10, Claim 11, delete "-6, 7-dihydro-" and insert -- -6,7-dihydro- --;

Column 127, Lines 11-12, Claim 11, delete "-1, 4-" and insert -- -1,4- --.

Signed and Sealed this
Twenty-fourth Day of March, 2020

Andrei Iancu
*Director of the United States Patent and Trademark Office*